US012686709B2

(12) United States Patent
Zion et al.

(10) Patent No.: US 12,686,709 B2
(45) Date of Patent: Jul. 21, 2026

(54) PD-L1 ANALOG FUSION PROTEINS FOR ANTIGEN SPECIFIC IMMUNOTHERAPY AND METHODS OF USE

(71) Applicant: AKSTON BIOSCIENCES CORPORATION, Beverly, MA (US)

(72) Inventors: Todd C. Zion, Salem, MA (US); Thomas M. Lancaster, Wenham, MA (US)

(73) Assignee: AKSTON BIOSCIENCES CORPORATION, Beverly, MA (US)

( * ) Notice: Subject to any disclaimer, the term of this patent is extended or adjusted under 35 U.S.C. 154(b) by 0 days.

(21) Appl. No.: 19/352,098

(22) Filed: Oct. 7, 2025

(65) Prior Publication Data

US 2026/0035433 A1     Feb. 5, 2026

Related U.S. Application Data

(63) Continuation of application No. 19/071,424, filed on Mar. 5, 2025, now Pat. No. 12,454,565.

(60) Provisional application No. 63/568,130, filed on Mar. 21, 2024, provisional application No. 63/568,146, filed on Mar. 21, 2024, provisional application No. 63/568,097, filed on Mar. 21, 2024, provisional application No. 63/568,173, filed on Mar. 21, 2024, provisional application No. 63/568,116, filed on Mar. 21, 2024.

(51) Int. Cl.
    *C07K 14/705*     (2006.01)
    *A61K 39/00*      (2006.01)

(52) U.S. Cl.
    CPC ........ *C07K 14/70532* (2013.01); *A61K 39/00* (2013.01); *C07K 2319/30* (2013.01)

(58) Field of Classification Search
    None
    See application file for complete search history.

(56) References Cited

U.S. PATENT DOCUMENTS

| | | | |
|---|---|---|---|
| 10,851,147 B2 | 12/2020 | Lancaster et al. | |
| 10,870,686 B2 | 12/2020 | Lancaster et al. | |
| 10,947,292 B2 | 3/2021 | Lancaster et al. | |
| 10,961,294 B2 * | 3/2021 | Lancaster | A61K 9/0019 |
| 11,186,623 B2 | 11/2021 | Lancaster et al. | |
| 11,261,229 B2 | 3/2022 | Lancaster et al. | |
| 11,267,862 B2 | 3/2022 | Lancaster et al. | |
| 11,498,953 B2 | 11/2022 | Brondyk et al. | |
| 11,673,934 B2 | 6/2023 | Lancaster et al. | |
| 11,773,151 B2 | 10/2023 | Lancaster et al. | |
| 11,919,935 B2 | 3/2024 | Lancaster et al. | |
| 12,454,565 B2 * | 10/2025 | Zion | C07K 14/70532 |
| 2010/0125127 A1 | 5/2010 | Mikesell et al. | |
| 2016/0311902 A1 | 10/2016 | Morsey et al. | |
| 2016/0319018 A1 * | 11/2016 | Morsey | C07K 16/2896 |
| 2016/0324932 A1 | 11/2016 | Baldwin et al. | |
| 2016/0333096 A1 | 11/2016 | Morsey et al. | |
| 2018/0237535 A1 | 8/2018 | Morsey et al. | |
| 2020/0231646 A1 | 7/2020 | Lancaster et al. | |
| 2020/0407414 A1 | 12/2020 | Lancaster et al. | |
| 2022/0088182 A1 | 3/2022 | Zion et al. | |
| 2022/0213167 A1 * | 7/2022 | Spindler | C07K 14/7051 |
| 2024/0101635 A1 | 3/2024 | Lancaster et al. | |
| 2024/0182539 A1 | 6/2024 | Lancaster et al. | |
| 2025/0011431 A1 | 1/2025 | Baer et al. | |
| 2025/0289863 A1 | 9/2025 | Lancaster et al. | |
| 2026/0015423 A1 | 1/2026 | Liu et al. | |

FOREIGN PATENT DOCUMENTS

| | | |
|---|---|---|
| WO | 2022/192898 | 9/2022 |
| WO | 2026008017 | 1/2026 |
| WO | 2026008026 | 1/2026 |

OTHER PUBLICATIONS

International Search Report and Written Opinion in corresponding PCT Application Serial No. PCT/US2025/018549, dated May 8, 2025.
Barroso-Gomila, et al., "Identification of proximal SUMO-dependent interactors using SUMO-ID", Nature Communication, 2021, 12(1), 6671.
Office Action in corresponding U.S. Appl. No. 19/071,424, dated Apr. 24, 2025.

* cited by examiner

*Primary Examiner* — Ilia I Ouspenski
(74) *Attorney, Agent, or Firm* — Hovey Williams LLP; Crissa A. Cook

(57)     ABSTRACT

The present disclosure provides recombinantly manufactured fusion proteins comprising a Programmed Death-Ligand 1 (PD-L1) protein fragment or an analog thereof linked to a canine Fc fragment. Embodiments include the administration of the fusion proteins to patients as a treatment for cancers, tumors or other diseases associated with expression of the PD-L1 protein in dogs. Exemplary Fc fusion proteins and pharmaceutical formulations of exemplary Fc fusion proteins are provided, in addition to methods of use and preparation.

18 Claims, 38 Drawing Sheets

Specification includes a Sequence Listing.

```
SEQ ID NO: 2    MRIFAVFIEMTYWHLLNAFTVTVPKDLYVVEYGSNMTIECKFPVEKQLDLAALIVYWEME    60
SEQ ID NO: 3    MRMFSVFTFMAYCHLLKAFTITVSKDLYVVEYGGNVTMECKFPVEKQLNLFALIVYWEME    60
                **:.:** **:* ****:.***.*.:.**********:.* **********:* ******

SEQ ID NO: 2    DKNIIQFVHGEEDLKVQHSSYRQRARLLKDQLSLGNAALQITDVKLQDAGVYRCMISYGG   120
SEQ ID NO: 3    DKKIIQFVNGKEDLKVQHSSYSQRAQLLKDQLFLGKAALQITDVRLQDAGVYCCLIGYGG   120
                **::****::*:*********.***:*******.**:*******:******* *:.***

SEQ ID NO: 2    ADYKRITVKVNAPYNKINQRILVVDPVTSEHELTCQAEGYPKAEVIWTSSDHQVLSGKTT   180
SEQ ID NO: 3    ADYKRITLKVHAPYRNISQRI-SVDPVTSEHELMCQAEGYPEAEVIWTSSDHRVLSGKTT   179
                *******:**:***:*:.****  *.********:******:********* ********

SEQ ID NO: 2    TTNSKREEKLFNVTSTLRINTTTNEIFYCTFRRLDPEENHTAELVIPELPLAHPPNERTH   240
SEQ ID NO: 3    ITNSNREEKLFNVTSTLNINATANEIFYCTFQRSGPEENNTAELVIPER-LPVPASERTH   238
                .***.***********.:*.*.*********:*..****:.*******:* . ****

SEQ ID NO: 2    LVILGAILLCLGVALTFIFRLR-KGRMMDVKKCGIQDTNSKKQSDTHLEET   290
SEQ ID NO: 3    FMILGPFLLLLGVVLAVTFCLKKHGRMMDVEKCCTRDRNSKKRNDIQFEET   289
                ::*** :** **:.*:.*: :*******:** *:*:**:*::* *:.***
```

FIG. 2

```
SEQ ID NO: 4  MQIPQAPWPVVWAVLQLGWRPGWFLDSPDRPWNPPTFSPALLVVTEGDNATFTCSFSNTS   60
SEQ ID NO: 5  MGSRRGPWPLVWAVLQLGWWPGWLLDSPDRPWSPLIFSPAQLTVQEGENATFTCSLLADIP  60
              *  :.*:********** ***;:******** *    * :* **:*********;::

SEQ ID NO: 4  ESFVLNWYRMSPSNQTDKLAAFPEDRSQPGQDCRFRVTQLPNGRDFHMSVVRARRNDSGT  120
SEQ ID NO: 5  DSFVLNWYRLSPRNQTDKLAAFQEDRIEPGRDRRFRVTRLPNGRDFHMSIVAARLNDSGI  120
              :*******;:** *********:**  .** .***:*;*:******:* ** ****

SEQ ID NO: 4  YLCGAISLAPKAQIKESLRAELRVTERRAEVPTAHPSPSPRPAGQFQTLVVGVVGGLLGS  180
SEQ ID NO: 5  YLCGAIYLPPNTQINESPRAELSVTERTLEPPTQSPSPPPRLSGQLQGLIGVTSVLVGV   180
              ****** * *:.*:*** ****.*** : * **  .****.  . :*.:**.. *:*

SEQ ID NO: 4  LV--LLVWVLAVICSRAARGTIGARRTGQPLKEDPSAVPVFSVDYGELDFQWREKTPEPP  238
SEQ ID NO: 5  LILLLITWVLAAVFPRATRGACVCGSEDEPLKEGPDAAPVFTLDYGELDFQWREKTPEPP  240
              *:  .: **.** :.: .  .   .:.****.:.****:.:.*************

SEQ ID NO: 4  VPCVPEQTEYATIVFPSGMGTSSPARRGSADGPRSAQPLRPEDGHCSWPL  288
SEQ ID NO: 5  APCAPEQTEYATIVFPGRP--ASPGRRASASSLQGAQPPSPEDGPGLWPL  288
              .**.**********:  :: .:..*** .:.:.*** ****  ***
```

FIG. 3

```
SEQ ID NO: 8    --------------------TIECKFPVEKQLDLAALIVYWEMEDKNIIQFVHGEEDLKVQH   42
SEQ ID NO: 9    ------------------------------------------------------------    0
SEQ ID NO: 10   FTVTVPKDLYVVEYGSNMTIECKFPVEKQLDLAALIVYWEMEDKNIIQFVHGEEDLKVQH   60
SEQ ID NO: 11   ------------------------------------------------------------    0

SEQ ID NO: 8    SSYRQRARLLKDQLSLGNAALQITDVKLQDAGVYRCMISYGGADYKRITVKVNAPYNKIN  102
SEQ ID NO: 9    ----------------------------MISYGGADYKRITVKVNAPYNKIN          24
SEQ ID NO: 10   SSYRQRARLLKDQLSLGNAALQITDVKLQDAGVYRCMISYGGADYKRITVKVNAPYNKIN  120
SEQ ID NO: 11   ----------------------------MISYGGADYKRITVKVNAPYNKIN          24
                                            ********************

SEQ ID NO: 8    QRILVVDPVTSEHELTCQAEGYPKAEVIWTSSDHQVLSGKTTTNSKREEKLFNVTSTLR  162
SEQ ID NO: 9    QRILVVDPVTSEHELTCQAEGYPKAEVIWTSSDHQVLSGKTTTNSKREEKLFNVTSTLR   84
SEQ ID NO: 10   QRILVVDPVTS-----------------------------------------------  131
SEQ ID NO: 11   QRILVVDPVTS-----------------------------------------------   35
                ***********

SEQ ID NO: 8    INTTTNEIFYCTFRRLDPEENHTAELVIPELPLAHPPNERTHLVILGAI  211
SEQ ID NO: 9    INTTTNEIFYCTFRRLDPEENHTAELVIPELPLAHPPNERTHLVILGAI  133
SEQ ID NO: 10   ------------------------------------------------  131
SEQ ID NO: 11   ------------------------------------------------   35
```

FIG. 4

```
SEQ ID NO: 15    ----------------------------------------TIECKFPVEKQLDLAALIVYWEMEDKNIIQFVHGEEDLKVQH    42
SEQ ID NO: 16    ----------------------------------------------------------------------------------     0
SEQ ID NO: 17    FTVTVPKDLYVVEYGSNMTIECKFPVEKQLDLAALIVYWEMEDKNIIQFVHGEEDLKVQH                              60
SEQ ID NO: 18    ----------------------------------------------------------------------------------     0

SEQ ID NO: 15    SSYRQRARLLKDQLSLGNAALQITDVKLQDAGVYRCMISYGGADYKRITVKVNAPYNKIN                             102
SEQ ID NO: 16    ----------------------------------------MISYGGADYKRITVKVNAPYNKIN                          24
SEQ ID NO: 17    SSYRQRARLLKDQLSLGNAALQITDVKLQDAGVYRCMISYGGADYKRITVKVNAPYNKIN                             120
SEQ ID NO: 18    ----------------------------------------MISYGGADYKRITVKVNAPYNKIN                          24
                                                         ********************

SEQ ID NO: 15    QRILVVDPVTSEHELTCQAEGYPKAEVIWTSSDHQVLSGKTTTTNSKREEKLFNVTSTLR                             162
SEQ ID NO: 16    QRILVVDPVTSEHELTCQAEGYPKAEVIWTSSDHQVLSGKTTTTNSKREEKLFNVTSTLR                              84
SEQ ID NO: 17    QRILVVDPVT--------------------------------------------------                             130
SEQ ID NO: 18    QRILVVDPVT--------------------------------------------------                              34
                 **********
```

FIG. 5A

SEQ ID NO: 15  INTTTNEIFYCTFRRLDPEENHTAELVIPELPLAHPPNERTHLVILGAIGGGGQGGGGSGG  222
SEQ ID NO: 16  INTTTNEIFYCTFRRLDPEENHTAELVIPELPLAHPPNERTHLVILGAIGGGGQGGGGSGG  144
SEQ ID NO: 17  --------------------------------------------------SGGGGQGGGGSGG  142
SEQ ID NO: 18  --------------------------------------------------SGGGGQGGGGSGG  46
                                                                 **************

SEQ ID NO: 15  QGGGGGDCPKCPAPEMLGGPSVFIFPPKPKDTLLIARTPEVTCVVVDLDPEDPEVQISWF  282
SEQ ID NO: 16  QGGGGGDCPKCPAPEMLGGPSVFIFPPKPKDTLLIARTPEVTCVVVDLDPEDPEVQISWF  204
SEQ ID NO: 17  QGGGGGDCPKCPAPEMLGGPSVFIFPPKPKDTLLIARTPEVTCVVVDLDPEDPEVQISWF  202
SEQ ID NO: 18  QGGGGGDCPKCPAPEMLGGPSVFIFPPKPKDTLLIARTPEVTCVVVDLDPEDPEVQISWF  106
               *************************************************************

SEQ ID NO: 15  VDGKQMQTAKTQPREEQFNGTYRVVSVLPIGHQDWLKGKQFTCKVNNKALPSPIERTISK  342
SEQ ID NO: 16  VDGKQMQTAKTQPREEQFNGTYRVVSVLPIGHQDWLKGKQFTCKVNNKALPSPIERTISK  264
SEQ ID NO: 17  VDGKQMQTAKTQPREEQFNGTYRVVSVLPIGHQDWLKGKQFTCKVNNKALPSPIERTISK  262
SEQ ID NO: 18  VDGKQMQTAKTQPREEQFNGTYRVVSVLPIGHQDWLKGKQFTCKVNNKALPSPIERTISK  166
               *************************************************************

FIG. 5B

```
SEQ ID NO: 15    ARGQAHQPSVYVLPPSREELSKNTVSLTCLIKDFFPPDIDVEWQSNGQQEPESKYRTTPP    402
SEQ ID NO: 16    ARGQAHQPSVYVLPPSREELSKNTVSLTCLIKDFFPPDIDVEWQSNGQQEPESKYRTTPP    324
SEQ ID NO: 17    ARGQAHQPSVYVLPPSREELSKNTVSLTCLIKDFFPPDIDVEWQSNGQQEPESKYRTTPP    322
SEQ ID NO: 18    ARGQAHQPSVYVLPPSREELSKNTVSLTCLIKDFFPPDIDVEWQSNGQQEPESKYRTTPP    226
                 ************************************************************

SEQ ID NO: 15    QLDEDGSYFLYSKLSVDKSRWQRGDTFICAVMHEALHNHYTQESLSHSPG    452
SEQ ID NO: 16    QLDEDGSYFLYSKLSVDKSRWQRGDTFICAVMHEALHNHYTQESLSHSPG    374
SEQ ID NO: 17    QLDEDGSYFLYSKLSVDKSRWQRGDTFICAVMHEALHNHYTQESLSHSPG    372
SEQ ID NO: 18    QLDEDGSYFLYSKLSVDKSRWQRGDTFICAVMHEALHNHYTQESLSHSPG    276
                 **************************************************
```

FIG. 5C

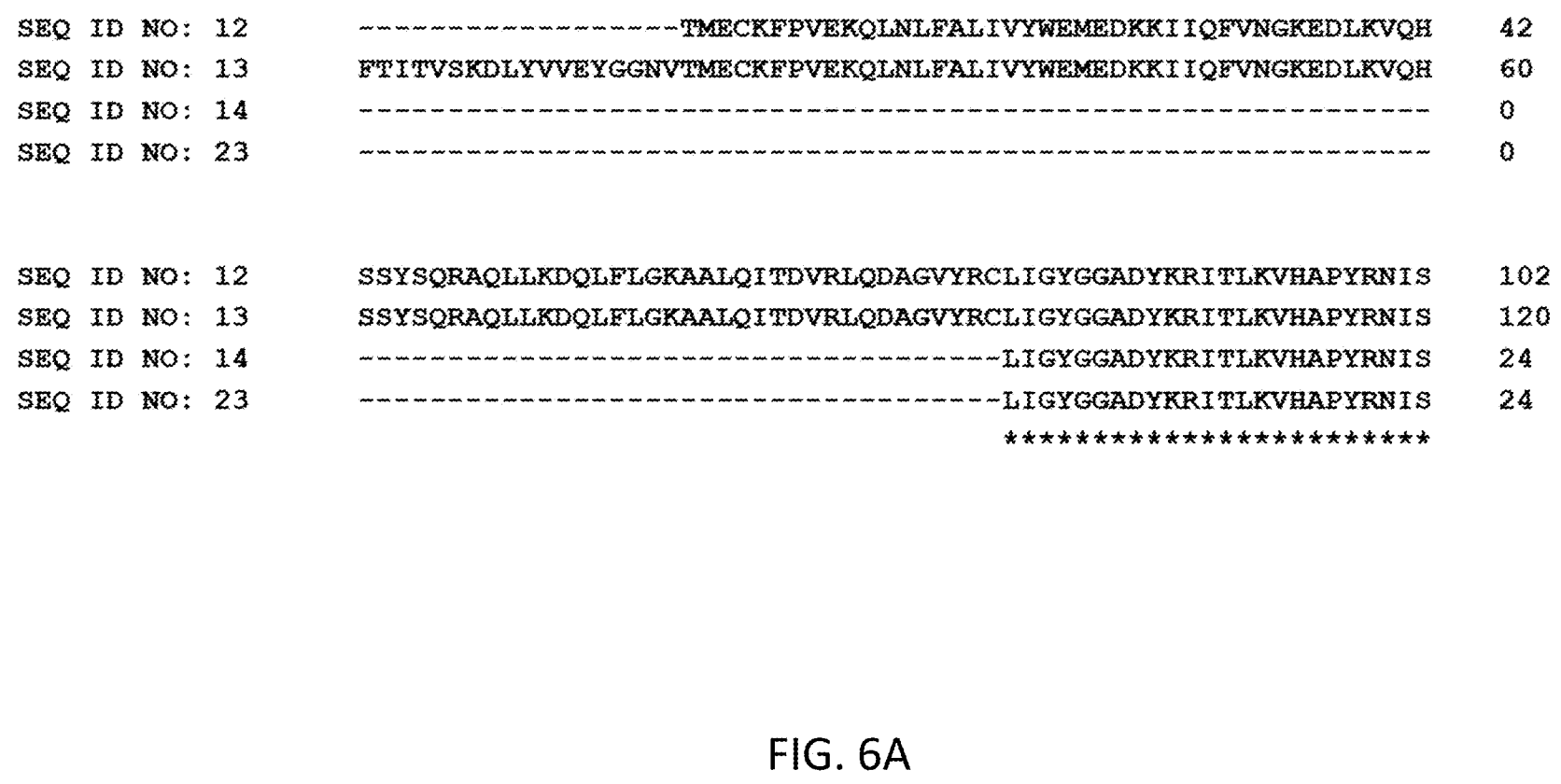

```
SEQ ID NO: 12  --------------------------TMECKFPVEKQLNLFALIVYWEMEDKKIIQFVNGKEDLKVQH   42
SEQ ID NO: 13  FTITVSKDLYVVEYGGNVTMECKFPVEKQLNLFALIVYWEMEDKKIIQFVNGKEDLKVQH   60
SEQ ID NO: 14  ------------------------------------------------------------    0
SEQ ID NO: 23  ------------------------------------------------------------    0

SEQ ID NO: 12  SSYSQRAQLLKDQLFLGKAALQITDVRLQDAGVYRCLIGYGGADYKRITLKVHAPYRNIS  102
SEQ ID NO: 13  SSYSQRAQLLKDQLFLGKAALQITDVRLQDAGVYRCLIGYGGADYKRITLKVHAPYRNIS  120
SEQ ID NO: 14  -------------------------------------LIGYGGADYKRITLKVHAPYRNIS   24
SEQ ID NO: 23  -------------------------------------LIGYGGADYKRITLKVHAPYRNIS   24
                                                    ************************
```

FIG. 6A

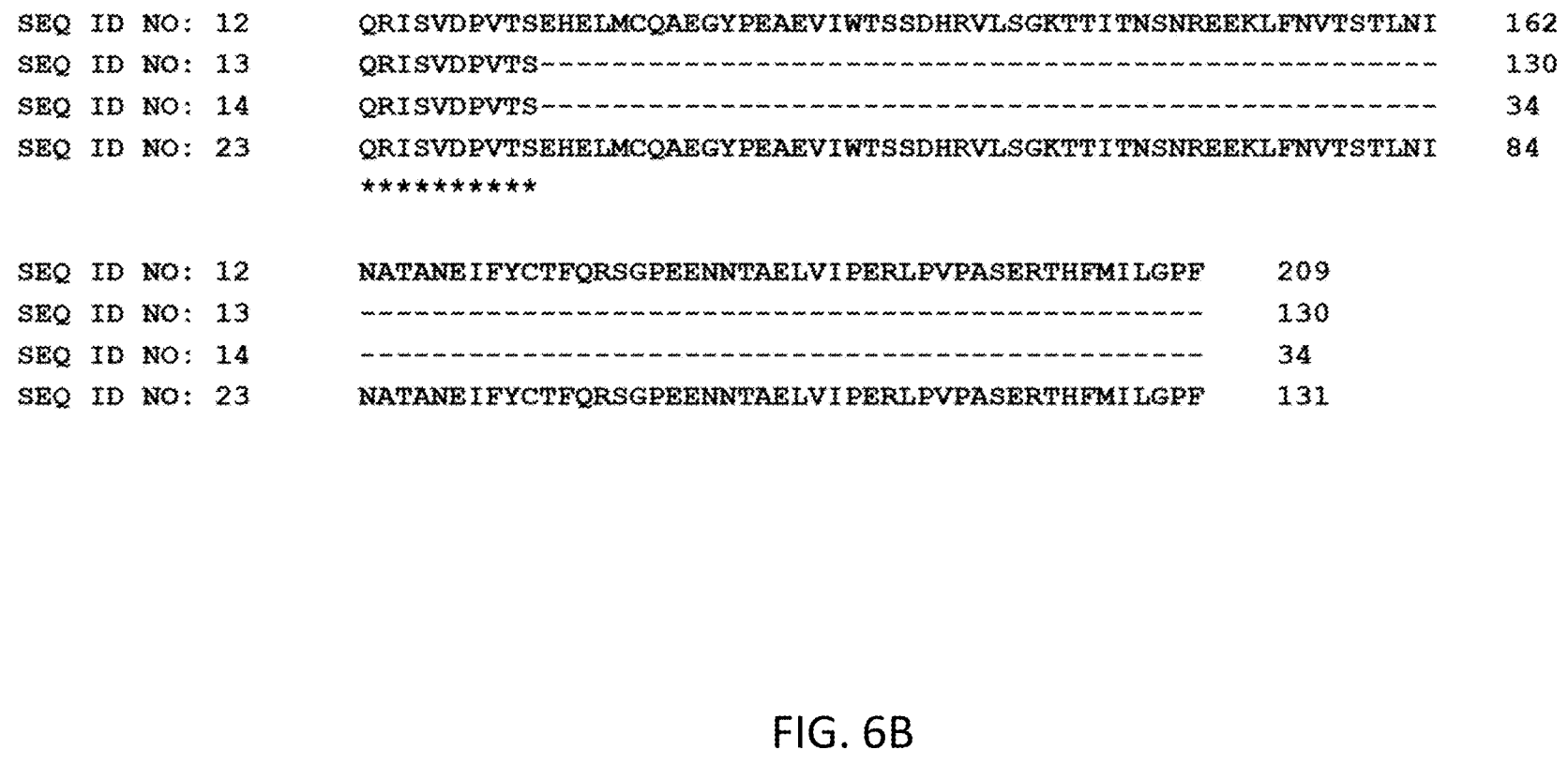

SEQ ID NO: 12    QRISVDPVTSEHELMCQAEGYPEAEVIWTSSDHRVLSGKTTITNSNREEKLFNVTSTLNI    162
SEQ ID NO: 13    QRISVDPVTS-------------------------------------------------    130
SEQ ID NO: 14    QRISVDPVTS-------------------------------------------------    34
SEQ ID NO: 23    QRISVDPVTSEHELMCQAEGYPEAEVIWTSSDHRVLSGKTTITNSNREEKLFNVTSTLNI    84
                 **********

SEQ ID NO: 12    NATANEIFYCTFQRSGPEENNTAELVIPERLPVPASERTHFMILGPF    209
SEQ ID NO: 13    -----------------------------------------------    130
SEQ ID NO: 14    -----------------------------------------------    34
SEQ ID NO: 23    NATANEIFYCTFQRSGPEENNTAELVIPERLPVPASERTHFMILGPF    131

FIG. 6B

```
SEQ ID NO: 19  --------------------------------TMECKFPVEKQLNLFALIVYWEMEDKKIIQFVNGKEDLKVQH   42
SEQ ID NO: 20  FTITVSKDLYVVEYGGNVTMECKFPVEKQLNLFALIVYWEMEDKKIIQFVNGKEDLKVQH   60
SEQ ID NO: 21  ------------------------------------------------------------    0
SEQ ID NO: 22  FTITVSKDLYVVEYGGNVTMECKFPVEKQLNLFALIVYWEMEDKKIIQFVNGKEDLKVQH   60
SEQ ID NO: 24  ------------------------------------------------------------    0

SEQ ID NO: 19  SSYSQRAQLLKDQLFLGKAALQITDVRLQDAGVYRCLIGYGGADYKRITLKVHAPYRNIS  102
SEQ ID NO: 20  SSYSQRAQLLKDQLFLGKAALQITDVRLQDAGVYRCLIGYGGADYKRITLKVHAPYRNIS  120
SEQ ID NO: 21  ------------------------------------LIGYGGADYKRITLKVHAPYRNIS   24
SEQ ID NO: 22  SSYSQRAQLLKDQLFLGKAALQITDVRLQDAGVYRCLIGYGGADYKRITLKVHAPYRNIS  120
SEQ ID NO: 24  ------------------------------------LIGYGGADYKRITLKVHAPYRNIS   24
                                                   ************************

SEQ ID NO: 19  QRISVDPVTSEHELMCQAEGYPEAEVIWTSSDHRVLSGKTTITNSNREEKLFNVTSTLNI  162
SEQ ID NO: 20  QRISVDPVT---------------------------------------------------  129
SEQ ID NO: 21  QRISVDPVT---------------------------------------------------   33
SEQ ID NO: 22  QRISVDPVTSQ-------------------------------------------------  131
SEQ ID NO: 24  QRISVDPVTSEHELMCQAEGYPEAEVIWTSSDHRVLSGKTTITNSNREEKLFNVTSTLNI   84
               *********
```

FIG. 7A

```
SEQ ID NO: 19   NATANEIFYCTFQRSGPEENNTAELVIPERLPVPASERTHFMILGPFGGGQGGGSGGQG   222
SEQ ID NO: 20   ------------------------------------------SGGGQGGGSGGQG   143
SEQ ID NO: 21   ----------------------------------------SGGGQGGGSGGQG    47
SEQ ID NO: 22   -----------------------------------------------------GGG   134
SEQ ID NO: 24   NATANEIFYCTFQRSGPEENNTAELVIPERLPVPASERTHFMILGPFGGGQGGGSGGQG   144
                                                                  *   *

SEQ ID NO: 19   GGGGDCPKCPAPEMLGGPSVFIFPPKPKDTLLIARTPEVTCVVVDLDPEDPEVQISWFVD   282
SEQ ID NO: 20   GGGGDCPKCPAPEMLGGPSVFIFPPKPKDTLLIARTPEVTCVVVDLDPEDPEVQISWFVD   203
SEQ ID NO: 21   GGGGDCPKCPAPEMLGGPSVFIFPPKPKDTLLIARTPEVTCVVVDLDPEDPEVQISWFVD   107
SEQ ID NO: 22   SGGQDCPKCPAPEMLGGPSVFIFPPKPKDTLLIARTPEVTCVVVDLDPEDPEVQISWFVD   194
SEQ ID NO: 24   GGGGDCPKCPAPEMLGGPSVFIFPPKPKDTLLIARTPEVTCVVVDLDPEDPEVQISWFVD   204
                .**  *********************************************************

SEQ ID NO: 19   GKQMQTAKTQPREEQFNGTYRVVSVLPIGHQDWLKGKQFTCKVNNKALPSPIERTISKAR   342
SEQ ID NO: 20   GKQMQTAKTQPREEQFNGTYRVVSVLPIGHQDWLKGKQFTCKVNNKALPSPIERTISKAR   263
SEQ ID NO: 21   GKQMQTAKTQPREEQFNGTYRVVSVLPIGHQDWLKGKQFTCKVNNKALPSPIERTISKAR   167
SEQ ID NO: 22   GKQMQTAKTQPREEQFNGTYRVVSVLPIGHQDWLKGKQFTCKVNNKALPSPIERTISKAR   254
SEQ ID NO: 24   GKQMQTAKTQPREEQFNGTYRVVSVLPIGHQDWLKGKQFTCKVNNKALPSPIERTISKAR   264
                ************************************************************
```

FIG. 7B

```
SEQ ID NO: 19  GQAHQPSVYVLPPSREELSKNTVSLTCLIKDFFPPDIDVEWQSNGQQEPESKYRTTPPQL  402
SEQ ID NO: 20  GQAHQPSVYVLPPSREELSKNTVSLTCLIKDFFPPDIDVEWQSNGQQEPESKYRTTPPQL  323
SEQ ID NO: 21  GQAHQPSVYVLPPSREELSKNTVSLTCLIKDFFPPDIDVEWQSNGQQEPESKYRTTPPQL  227
SEQ ID NO: 22  GQAHQPSVYVLPPSREELSKNTVSLTCLIKDFFPPDIDVEWQSNGQQEPESKYRTTPPQL  314
SEQ ID NO: 24  GQAHQPSVYVLPPSREELSKNTVSLTCLIKDFFPPDIDVEWQSNGQQEPESKYRTTPPQL  324
               ************************************************************

SEQ ID NO: 19  DEDGSYFLYSKLSVDKSRWQRGDTFICAVMHEALHNHYTQESLSHSPG  450
SEQ ID NO: 20  DEDGSYFLYSKLSVDKSRWQRGDTFICAVMHEALHNHYTQESLSHSPG  371
SEQ ID NO: 21  DEDGSYFLYSKLSVDKSRWQRGDTFICAVMHEALHNHYTQESLSHSPG  275
SEQ ID NO: 22  DEDGSYFLYSKLSVDKSRWQRGDTFICAVMHEALHNHYTQESLSHSPG  362
SEQ ID NO: 24  DEDGSYFLYSKLSVDKSRWQRGDTFICAVMHEALHNHYTQESLSHSPG  372
               ***********************************************
```

FIG. 7C

```
SEQ ID NO: 12   ----------------------------------------TMECKFPVEKQLNLFALIVYWEMEDKKIIQFVNGKEDLKVQH   42
SEQ ID NO: 13   FTITVSKDLYVVEYGGNVTMECKFPVEKQLNLFALIVYWEMEDKKIIQFVNGKEDLKVQH   60
SEQ ID NO: 14   ------------------------------------------------------------   0
SEQ ID NO: 25   FTITVSKDLYVVEYGGNVTMECKFPVEKQLNLFALIVYWEMEDKKIIQFVNGKEDLKVQH   60

SEQ ID NO: 12   SSYSQRAQLLKDQLFLGKAALQITDVRLQDAGVYRCLIGYGGADYKRITLKVHAPYRNIS   102
SEQ ID NO: 13   SSYSQRAQLLKDQLFLGKAALQITDVRLQDAGVYRCLIGYGGADYKRITLKVHAPYRNIS   120
SEQ ID NO: 14   ------LIGYGGADYKRITLKVHAPYRNIS   24
SEQ ID NO: 25   SSYSQRAQLLKDQLFLGKAALQITDVRLQDAGVYRCLIGYGGADYKRITLKVHAPYRNIS   120
                                  ***************************
```

FIG. 8A

```
SEQ ID NO: 12    QRISVDPVTSEHELMCQAEGYPEAEVIWTSSDHRVLSGKTTTTNSNREEKLFNVTSTLNI    162
SEQ ID NO: 13    QRISVDPVTS--------------------------------------------------    130
SEQ ID NO: 14    QRISVDPVTS--------------------------------------------------    34
SEQ ID NO: 25    QRISVDPVTSEHELMCQAEGYPEAEVIWTSSDHRVLSGKTTTTNSNREEKLFNVTSTLNI    180
                 **********

SEQ ID NO: 12    NATANEIFYCTFQRSGPEENNTAELVIPERLPVPASERTHFMILGPF    209
SEQ ID NO: 13    -----------------------------------------------    130
SEQ ID NO: 14    -----------------------------------------------    34
SEQ ID NO: 25    NATANEIFYCTFQRSGPEENNTAELVIPERLPVPASERTHFMILGPF    227
```

FIG. 8B

```
SEQ ID NO: 19   ------------------------TMECKFPVEKQINLFALIVYWEMEDKKIIQFVNGKEDLKVQH   42
SEQ ID NO: 20   FTITVSKDLYVVEYGGNVTMECKFPVEKQINLFALIVYWEMEDKKIIQFVNGKEDLKVQH          60
SEQ ID NO: 21   -------------------------------                                       0
SEQ ID NO: 22   FTITVSKDLYVVEYGGNVTMECKFPVEKQINLFALIVYWEMEDKKIIQFVNGKEDLKVQH          60
SEQ ID NO: 26   FTITVSKDLYVVEYGGNVTMECKFPVEKQINLFALIVYWEMEDKKIIQFVNGKEDLKVQH          60

SEQ ID NO: 19   SSYSQRAQLLKDQLFLGKAALQITDVRLQDAGVYRCLIGYGGADYKRITLKVHAPYRNIS        102
SEQ ID NO: 20   SSYSQRAQLLKDQLFLGKAALQITDVRLQDAGVYRCLIGYGGADYKRITLKVHAPYRNIS        120
SEQ ID NO: 21   -------------------------------LIGYGGADYKRITLKVHAPYRNIS              24
SEQ ID NO: 22   SSYSQRAQLLKDQLFLGKAALQITDVRLQDAGVYRCLIGYGGADYKRITLKVHAPYRNIS        120
SEQ ID NO: 26   SSYSQRAQLLKDQLFLGKAALQITDVRLQDAGVYRCLIGYGGADYKRITLKVHAPYRNIS        120
                                                       *********************

SEQ ID NO: 19   QRISVDPVTSEHELMCQAEGYPEAEVIWTSSDHRVLSGKTITITNSNREEKLFNVTSTLNI       162
SEQ ID NO: 20   QRISVDPVT-------------------------------------                       129
SEQ ID NO: 21   QRISVDPVT-                                                            33
SEQ ID NO: 22   QRISVDPVTS------------------------------------                        130
SEQ ID NO: 26   QRISVDPVTSEHELMCQAEGYPEAEVIWTSSDHRVLSGKTITITNSNREEKLFNVTSTLNI       180
                *********
```

FIG. 9A

```
SEQ ID NO: 19   NATANEIFYCTFQRSGPEENNTAELVIPERLPVPASERTHFMILGPFGGGQGGGSSGGQG   222
SEQ ID NO: 20   ----------------------------------------------SGGGGQGGGSSGGQG   143
SEQ ID NO: 21   ----------------------------------------------SGGGGQGGGSSGGQG    47
SEQ ID NO: 22   --------------------------------------------------QGGGS------   135
SEQ ID NO: 26   NATANEIFYCTFQRSGPEENNTAELVIPERLPVPASERTHFMILGPFQGGGS--------   232
                                                                   ***.

SEQ ID NO: 19   GGGGDCPKCPAPEMLGGPSVFIFPPKPKDTLLIARTPEVTCVVVDLDPEDPEVQISWFVD   282
SEQ ID NO: 20   GGGGDCPKCPAPEMLGGPSVFIFPPKPKDTLLIARTPEVTCVVVDLDPEDPEVQISWFVD   203
SEQ ID NO: 21   GGGGDCPKCPAPEMLGGPSVFIFPPKPKDTLLIARTPEVTCVVVDLDPEDPEVQISWFVD   107
SEQ ID NO: 22   -GGQDCPKCPAPEMLGGPSVFIFPPKPKDTLLIARTPEVTCVVVDLDPEDPEVQISWFVD   194
SEQ ID NO: 26   -GGQDCPKCPAPEMLGGPSVFIFPPKPKDTLLIARTPEVTCVVVDLDPEDPEVQISWFVD   291
                ** ************************************************

SEQ ID NO: 19   GKQMQTAKTQPREEQFNGTYRVVSVLPIGHQDWLKGKQFTCKVNNKALPSPIERTISKAR   342
SEQ ID NO: 20   GKQMQTAKTQPREEQFNGTYRVVSVLPIGHQDWLKGKQFTCKVNNKALPSPIERTISKAR   263
SEQ ID NO: 21   GKQMQTAKTQPREEQFNGTYRVVSVLPIGHQDWLKGKQFTCKVNNKALPSPIERTISKAR   167
SEQ ID NO: 22   GKQMQTAKTQPREEQFNGTYRVVSVLPIGHQDWLKGKQFTCKVNNKALPSPIERTISKAR   254
SEQ ID NO: 26   GKQMQTAKTQPREEQFNGTYRVVSVLPIGHQDWLKGKQFTCKVNNKALPSPIERTISKAR   351
                ************************************************
```

FIG. 9B

SEQ ID NO: 19   GQAHQPSVYVLPPSREELSKNTVSLTCLIKDFFPPDIDVEWQSNGQQEPESKYRTTPPQL   402
SEQ ID NO: 20   GQAHQPSVYVLPPSREELSKNTVSLTCLIKDFFPPDIDVEWQSNGQQEPESKYRTTPPQL   323
SEQ ID NO: 21   GQAHQPSVYVLPPSREELSKNTVSLTCLIKDFFPPDIDVEWQSNGQQEPESKYRTTPPQL   227
SEQ ID NO: 22   GQAHQPSVYVLPPSREELSKNTVSLTCLIKDFFPPDIDVEWQSNGQQEPESKYRTTPPQL   314
SEQ ID NO: 26   GQAHQPSVYVLPPSREELSKNTVSLTCLIKDFFPPDIDVEWQSNGQQEPESKYRTTPPQL   411
            ************************************************************

SEQ ID NO: 19   DEDGSYFLYSKLSVDKSRWQRGDTFICAVMHEALHNHYTQESLSHSPG   450
SEQ ID NO: 20   DEDGSYFLYSKLSVDKSRWQRGDTFICAVMHEALHNHYTQESLSHSPG   371
SEQ ID NO: 21   DEDGSYFLYSKLSVDKSRWQRGDTFICAVMHEALHNHYTQESLSHSPG   275
SEQ ID NO: 22   DEDGSYFLYSKLSVDKSRWQRGDTFICAVMHEALHNHYTQESLSHSPG   362
SEQ ID NO: 26   DEDGSYFLYSKLSVDKSRWQRGDTFICAVMHEALHNHYTQESLSHSPG   459
            ************************************************

FIG. 9C

```
SEQ ID NO: 19   ------------------TMECKFPVEKQLNLFALIVYWEMEDKKIIQFVNGKEDLKVQH   42
SEQ ID NO: 20   FTITVSKDLYVVEYGGNVTMECKFPVEKQLNLFALIVYWEMEDKKIIQFVNGKEDLKVQH   60
SEQ ID NO: 21   ------------------------------------------------------------    0
SEQ ID NO: 22   FTITVSKDLYVVEYGGNVTMECKFPVEKQLNLFALIVYWEMEDKKIIQFVNGKEDLKVQH   60
SEQ ID NO: 27   FTITVSKDLYVVEYGGNVTMECKFPVEKQLNLFALIVYWEMEDKKIIQFVNGKEDLKVQH   60

SEQ ID NO: 19   SSYSQRAQLLKDQLFLGKAALQITDVRLQDAGVYRCLIGYGGADYKRITLKVHAPYRNIS   102
SEQ ID NO: 20   SSYSQRAQLLKDQLFLGKAALQITDVRLQDAGVYRCLIGYGGADYKRITLKVHAPYRNIS   120
SEQ ID NO: 21   ---------------------------LIGYGGADYKRITLKVHAPYRNIS    24
SEQ ID NO: 22   SSYSQRAQLLKDQLFLGKAALQITDVRLQDAGVYRCLIGYGGADYKRITLKVHAPYRNIS   120
SEQ ID NO: 27   SSYSQRAQLLKDQLFLGKAALQITDVRLQDAGVYRCLIGYGGADYKRITLKVHAPYRNIS   120
                                          ****************************

SEQ ID NO: 19   QRISVDPVTSEHELMCQAEGYPEAEVIWTSSDHRVLSGKTTITNSNREEKLFNVTSTLNI   162
SEQ ID NO: 20   QRISVDPVT---------------------------------------------------   129
SEQ ID NO: 21   QRISVDPVT---------------------------------------------------    33
SEQ ID NO: 22   QRISVDPVTSQ-------------------------------------------------   131
SEQ ID NO: 27   QRISVDPVTSEHELMCQAEGYPEAEVIWTSSDHRVLSGKTTITNSNREEKLFNVTSTLNI   180
                *********
```

FIG. 10A

```
SEQ ID NO: 19  NATANEIFYCTFQRSGPEENNTAELVIPERLPVPASERTHFMILGPFGGGGQGGQGGSGGGQG  222
SEQ ID NO: 20  ------------------------------------------------------SGGGGQGGGQGGSGGGQG  143
SEQ ID NO: 21  ---------------------------------------------------------SGGGGQGGGSGGGQG  47
SEQ ID NO: 22  ----------------------------------------------------------------GGG  134
SEQ ID NO: 27  NATANEIFYCTFQRSGPEENNTAELVIPERLPVPASERTHFMILGPFGGGGQGGQGGSGGGQG  240
                                                                        *  *

SEQ ID NO: 19  GGGGDCPKCPAPEMLGGPSVFIFPPKPKDTLLIARTPEVTCVVVDLDPEDPEVQISWFVD  282
SEQ ID NO: 20  GGGGDCPKCPAPEMLGGPSVFIFPPKPKDTLLIARTPEVTCVVVDLDPEDPEVQISWFVD  203
SEQ ID NO: 21  GGGGDCPKCPAPEMLGGPSVFIFPPKPKDTLLIARTPEVTCVVVDLDPEDPEVQISWFVD  107
SEQ ID NO: 22  SGGQDCPKCPAPEMLGGPSVFIFPPKPKDTLLIARTPEVTCVVVDLDPEDPEVQISWFVD  194
SEQ ID NO: 27  GGGGDCPKCPAPEMLGGPSVFIFPPKPKDTLLIARTPEVTCVVVDLDPEDPEVQISWFVD  300
               .** *****************************************************

SEQ ID NO: 19  GKQMQTAKTQPREEQFNGTYRVVSVLPIGHQDWLKGKQFTCKVNNKALPSPIERTISKAR  342
SEQ ID NO: 20  GKQMQTAKTQPREEQFNGTYRVVSVLPIGHQDWLKGKQFTCKVNNKALPSPIERTISKAR  263
SEQ ID NO: 21  GKQMQTAKTQPREEQFNGTYRVVSVLPIGHQDWLKGKQFTCKVNNKALPSPIERTISKAR  167
SEQ ID NO: 22  GKQMQTAKTQPREEQFNGTYRVVSVLPIGHQDWLKGKQFTCKVNNKALPSPIERTISKAR  254
SEQ ID NO: 27  GKQMQTAKTQPREEQFNGTYRVVSVLPIGHQDWLKGKQFTCKVNNKALPSPIERTISKAR  360
               ***********************************************************
```

FIG. 10B

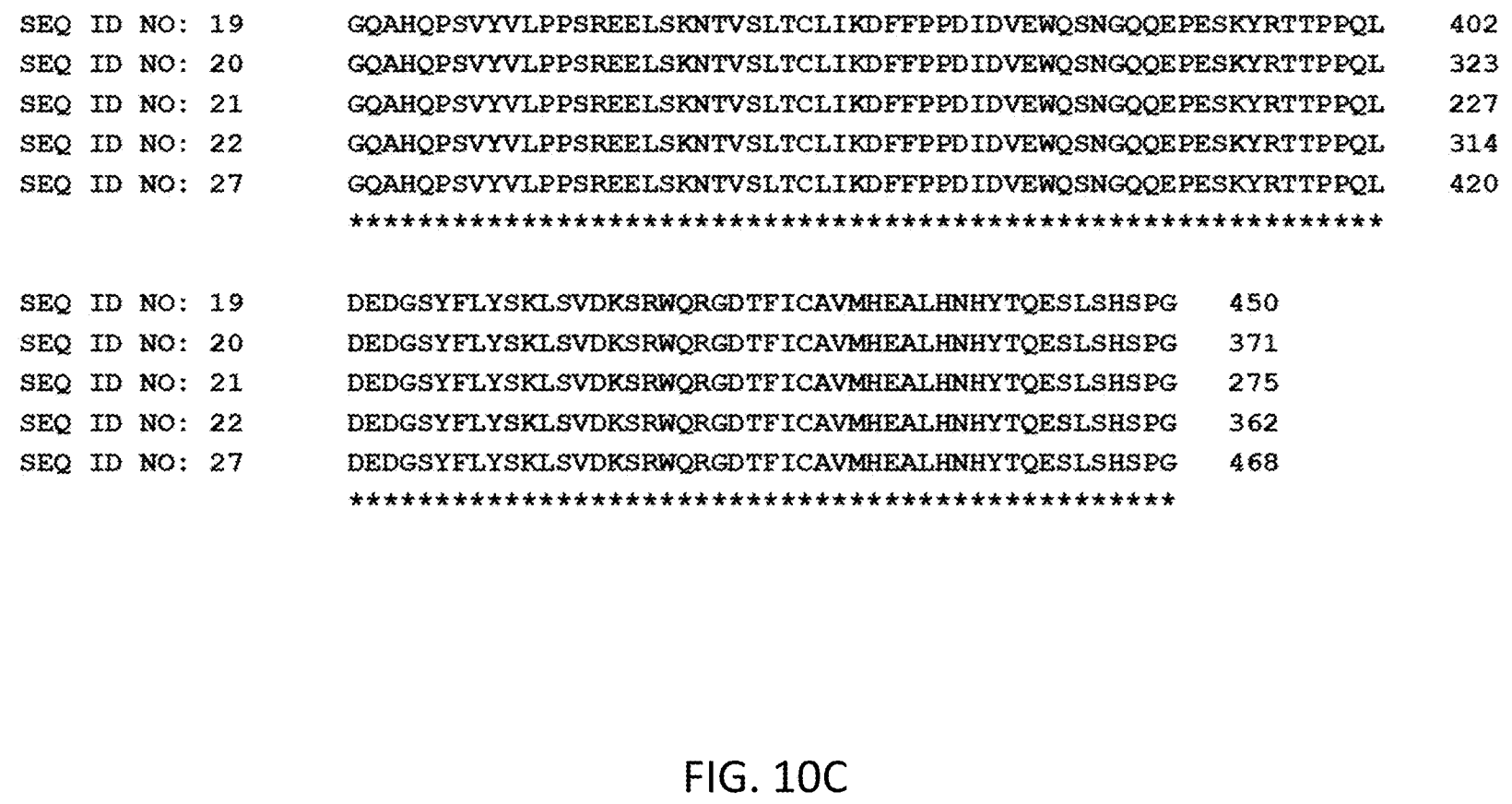

```
SEQ ID NO: 19    GQAHQPSVYVLPPSREELSKNTVSLTCLIKDFFPPDIDVEWQSNGQQEPESKYRTTPPQL    402
SEQ ID NO: 20    GQAHQPSVYVLPPSREELSKNTVSLTCLIKDFFPPDIDVEWQSNGQQEPESKYRTTPPQL    323
SEQ ID NO: 21    GQAHQPSVYVLPPSREELSKNTVSLTCLIKDFFPPDIDVEWQSNGQQEPESKYRTTPPQL    227
SEQ ID NO: 22    GQAHQPSVYVLPPSREELSKNTVSLTCLIKDFFPPDIDVEWQSNGQQEPESKYRTTPPQL    314
SEQ ID NO: 27    GQAHQPSVYVLPPSREELSKNTVSLTCLIKDFFPPDIDVEWQSNGQQEPESKYRTTPPQL    420
                 ************************************************************

SEQ ID NO: 19    DEDGSYFLYSKLSVDKSRWQRGDTFICAVMHEALHNHYTQESLSHSPG    450
SEQ ID NO: 20    DEDGSYFLYSKLSVDKSRWQRGDTFICAVMHEALHNHYTQESLSHSPG    371
SEQ ID NO: 21    DEDGSYFLYSKLSVDKSRWQRGDTFICAVMHEALHNHYTQESLSHSPG    275
SEQ ID NO: 22    DEDGSYFLYSKLSVDKSRWQRGDTFICAVMHEALHNHYTQESLSHSPG    362
SEQ ID NO: 27    DEDGSYFLYSKLSVDKSRWQRGDTFICAVMHEALHNHYTQESLSHSPG    468
                 ************************************************
```

FIG. 10C

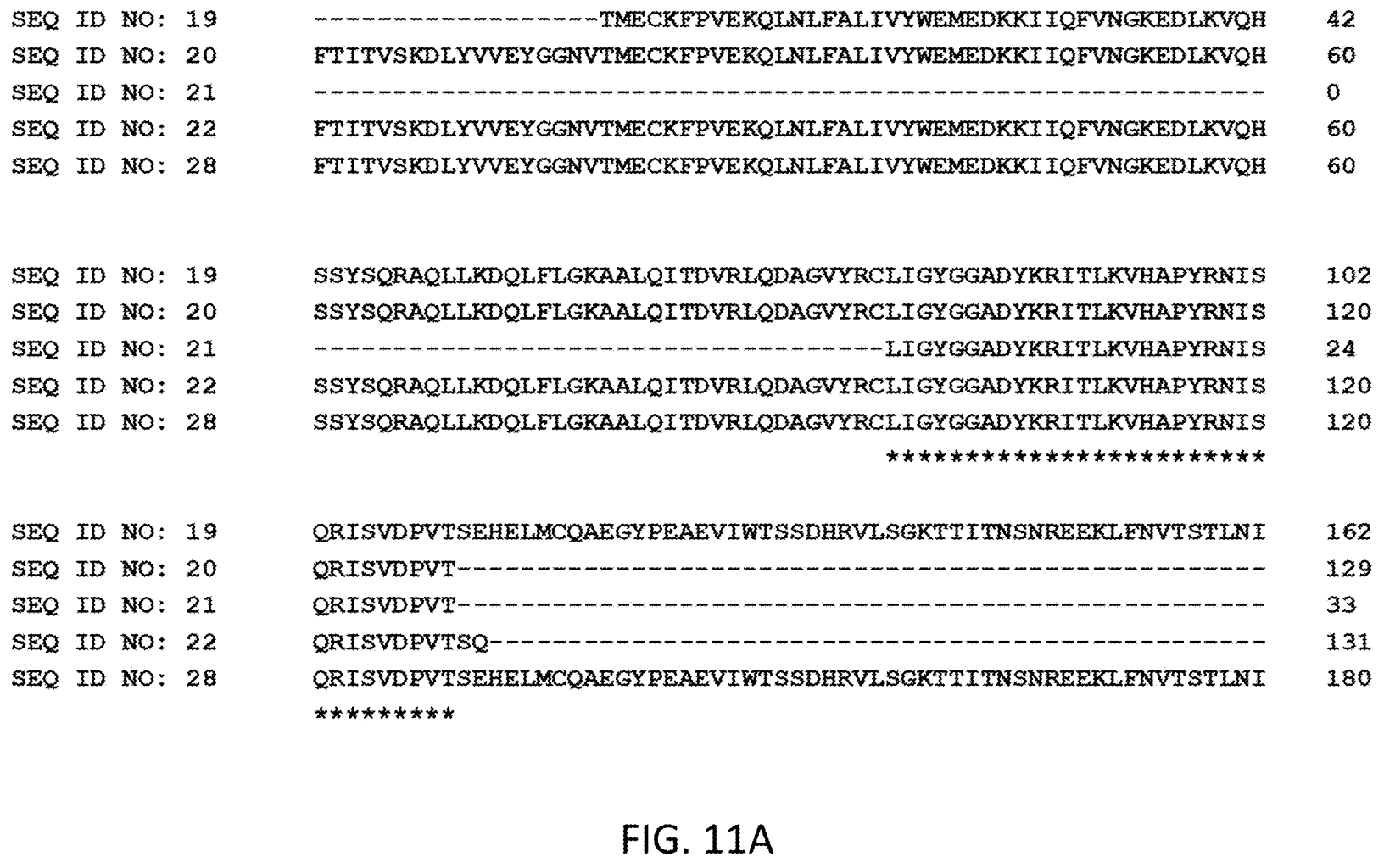

```
SEQ ID NO: 19  ------------------------TMECKFPVEKQLNLFALIVYWEMEDKKIIQFVNGKEDLKVQH   42
SEQ ID NO: 20  FTITVSKDLYVVEYGGNVTMECKFPVEKQLNLFALIVYWEMEDKKIIQFVNGKEDLKVQH         60
SEQ ID NO: 21  ------------------------------------------------------------         0
SEQ ID NO: 22  FTITVSKDLYVVEYGGNVTMECKFPVEKQLNLFALIVYWEMEDKKIIQFVNGKEDLKVQH         60
SEQ ID NO: 28  FTITVSKDLYVVEYGGNVTMECKFPVEKQLNLFALIVYWEMEDKKIIQFVNGKEDLKVQH         60

SEQ ID NO: 19  SSYSQRAQLLKDQLFLGKAALQITDVRLQDAGVYRCLIGYGGADYKRITLKVHAPYRNIS        102
SEQ ID NO: 20  SSYSQRAQLLKDQLFLGKAALQITDVRLQDAGVYRCLIGYGGADYKRITLKVHAPYRNIS        120
SEQ ID NO: 21  ---------------------------------LIGYGGADYKRITLKVHAPYRNIS           24
SEQ ID NO: 22  SSYSQRAQLLKDQLFLGKAALQITDVRLQDAGVYRCLIGYGGADYKRITLKVHAPYRNIS        120
SEQ ID NO: 28  SSYSQRAQLLKDQLFLGKAALQITDVRLQDAGVYRCLIGYGGADYKRITLKVHAPYRNIS        120
                                                    ***************************

SEQ ID NO: 19  QRISVDPVTSEHELMCQAEGYPEAEVIWTSSDHRVLSGKTTITNSNREEKLFNVTSTLNI        162
SEQ ID NO: 20  QRISVDPVT---------------------------------------------------        129
SEQ ID NO: 21  QRISVDPVT---------------------------------------------------         33
SEQ ID NO: 22  QRISVDPVTSQ-------------------------------------------------        131
SEQ ID NO: 28  QRISVDPVTSEHELMCQAEGYPEAEVIWTSSDHRVLSGKTTITNSNREEKLFNVTSTLNI        180
               *********
```

FIG. 11A

```
SEQ ID NO: 19    NATANEIFYCTFQRSGPEENNTAELVIPERLPVPASERTHFMILGPFGGGQGGGS--GG    220
SEQ ID NO: 20    -----------------------------------------------SGGGGQGGGGS--GG    141
SEQ ID NO: 21    -----------------------------------------------SGGGGQGGGGS--GG     45
SEQ ID NO: 22    -----------------------------------------------------------G    132
SEQ ID NO: 28    NATANEIFYCTFQRSGPEENNTAELVIPERLPVPASERTHFMILGPFGGGQGGGGSGGQGGG    240
                                                                           *

SEQ ID NO: 19    QGGGGGDCPKCPAPEMLGGPSVFIFPPKPKDTLLIARTPEVTCVVVDLDPEDPEVQISWF    280
SEQ ID NO: 20    QGGGGGDCPKCPAPEMLGGPSVFIFPPKPKDTLLIARTPEVTCVVVDLDPEDPEVQISWF    201
SEQ ID NO: 21    QGGGGGDCPKCPAPEMLGGPSVFIFPPKPKDTLLIARTPEVTCVVVDLDPEDPEVQISWF    105
SEQ ID NO: 22    GGSGGQDCPKCPAPEMLGGPSVFIFPPKPKDTLLIARTPEVTCVVVDLDPEDPEVQISWF    192
SEQ ID NO: 28    GGDKTHTCPPCPAPELLGGPSVFLFPPKPKDTLMISRTPEVTCVVVDVSHEDPEVKFNWY    300
                 *  ** ***** :  :******:*:*********** :********** :. ****:: **

SEQ ID NO: 19    VDGKQMQTAKTQPREEQFNGTYRVVSVLPIGHQDWLKGKQFTCKVNNKALPSPIERTISK    340
SEQ ID NO: 20    VDGKQMQTAKTQPREEQFNGTYRVVSVLPIGHQDWLKGKQFTCKVNNKALPSPIERTISK    261
SEQ ID NO: 21    VDGKQMQTAKTQPREEQFNGTYRVVSVLPIGHQDWLKGKQFTCKVNNKALPSPIERTISK    165
SEQ ID NO: 22    VDGKQMQTAKTQPREEQFNGTYRVVSVLPIGHQDWLKGKQFTCKVNNKALPSPIERTISK    252
SEQ ID NO: 28    VDGVEVHNAKTKPREEQYNSTYRVVSVLTVLHQDWLNGKEYKCKVSNKALPAPIEKTISK    360
                 *** :: :.:***:*:***.* .:***  : **** ** .:*** ..***.*:*****:*
```

FIG. 11B

```
SEQ ID NO: 19    ARGQAHQPSVYVLPPSREELSKNTVSLTCLIKDFFPPDIDVEWQSNGQQEPESKYRTTPP    400
SEQ ID NO: 20    ARGQAHQPSVYVLPPSREELSKNTVSLTCLIKDFFPPDIDVEWQSNGQQEPESKYRTTPP    321
SEQ ID NO: 21    ARGQAHQPSVYVLPPSREELSKNTVSLTCLIKDFFPPDIDVEWQSNGQQEPESKYRTTPP    225
SEQ ID NO: 22    ARGQAHQPSVYVLPPSREELSKNTVSLTCLIKDFFPPDIDVEWQSNGQQEPESKYRTTPP    312
SEQ ID NO: 28    AKGQPREPQVYTLPPSRDELITKNQVSLTCLVKGFYPSDIAVEWESNGQ--PENNYKTTPP   418
                 *:** ::*:*,**,******:**:**  * ** *****:* .* *** **:** *:*:***

SEQ ID NO: 19    QLDEDGSYFLYSKLSVDKSRWQRGDTFICAVMHEALHNHYTQESLSHSPG             450
SEQ ID NO: 20    QLDEDGSYFLYSKLSVDKSRWQRGDTFICAVMHEALHNHYTQESLSHSPG             371
SEQ ID NO: 21    QLDEDGSYFLYSKLSVDKSRWQRGDTFICAVMHEALHNHYTQESLSHSPG             275
SEQ ID NO: 22    QLDEDGSYFLYSKLSVDKSRWQRGDTFICAVMHEALHNHYTQESLSHSPG             362
SEQ ID NO: 28    VLDSDGSFFLYSKLTVDKSRWQQGNVFSCSVMHEALHNHYTQKSLSLSPG             468
                 **.***:******:******;:***:* .* *:*********:.**:*** *** ***
```

FIG. 11C

```
SEQ ID NO: 12   --------------------------------------TMECKFPVEKQLNLFALIVYWEMEDKKIIQFVNGKEDLKVQH   42
SEQ ID NO: 13   FTITVSKDLYVVEYGGNVTMECKFPVEKQLNLFALIVYWEMEDKKIIQFVNGKEDLKVQH   60
SEQ ID NO: 14   ------------------------------------------------------------   0
SEQ ID NO: 31   FTITVSKDLYVVEYGGNVTMECKFPVEKQLNLFALIVYWEMEDKKIIQFVNGKEDLKVQH   60

SEQ ID NO: 12   SSYSQRAQLLKDQLFLGKAALQITDVRLQDAGVYRCLIGYGGADYKRITLKVHAPYRNIS   102
SEQ ID NO: 13   SSYSQRAQLLKDQLFLGKAALQITDVRLQDAGVYRCLIGYGGADYKRITLKVHAPYRNIS   120
SEQ ID NO: 14   -------LIGYGGADYKRITLKVHAPYRNIS   24
SEQ ID NO: 31   SSYSQRAQLLKDQLFLGKAALQITDVRLQDAGVYCCLIGYGGADYKRITLKVHAPYRNIS   120
                       ******************************
```

FIG. 12A

```
SEQ ID NO: 12  QRISVDPVTSEHELMCQAEGYPEAEVIWTSSDHRVLSGKTTITNSNREEKLFNVTSTLNI  162
SEQ ID NO: 13  QRISVDPVTS--------------------------------------------------  130
SEQ ID NO: 14  QRISVDPVTS--------------------------------------------------  34
SEQ ID NO: 31  QRISVDPVTSEHELMCQAEGYPEAEVIWTSSDHRVLSGKTTITNSNREEKLFNVTSTLNI  180
               **********

SEQ ID NO: 12  NATANEIFYCTFQRSGPEENNTAELVIPERLPVPASERTHFMILGPF  209
SEQ ID NO: 13  -----------------------------------------------  130
SEQ ID NO: 14  -----------------------------------------------  34
SEQ ID NO: 31  NATANEIFYCTFQRSGPEENNTAELVIPERLPVPASERTHFMILGPF  227
```

FIG. 12B

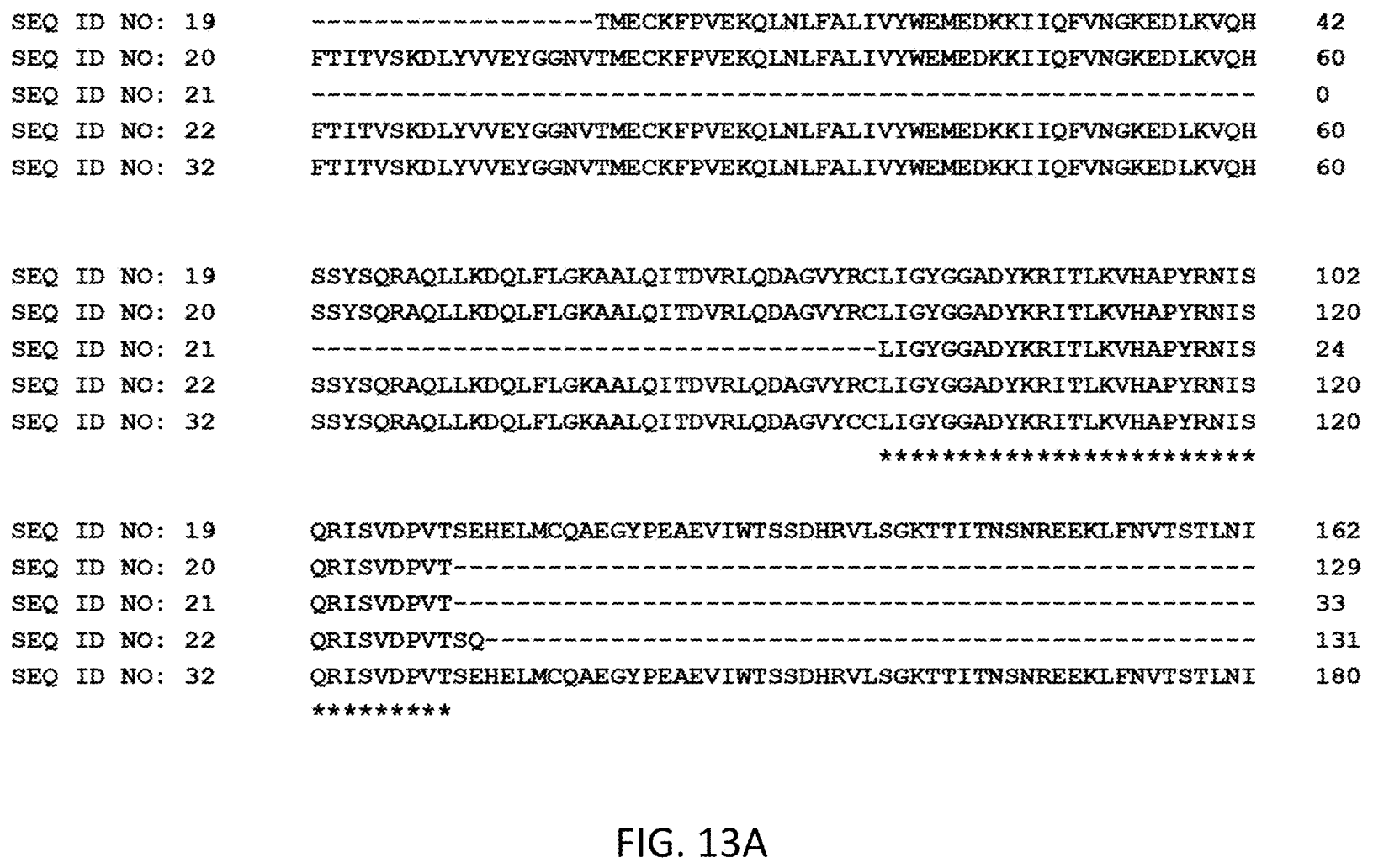

```
SEQ ID NO: 19   ----------TMECKFPVEKQLNLFALIVYWEMEDKKIIQFVNGKEDLKVQH        42
SEQ ID NO: 20   FTITVSKDLYVVEYGGNVTMECKFPVEKQLNLFALIVYWEMEDKKIIQFVNGKEDLKVQH   60
SEQ ID NO: 21   ----------                                                    0
SEQ ID NO: 22   FTITVSKDLYVVEYGGNVTMECKFPVEKQLNLFALIVYWEMEDKKIIQFVNGKEDLKVQH   60
SEQ ID NO: 32   FTITVSKDLYVVEYGGNVTMECKFPVEKQLNLFALIVYWEMEDKKIIQFVNGKEDLKVQH   60

SEQ ID NO: 19   SSYSQRAQLLKDQLFLGKAALQITDVRLQDAGVYRCLIGYGGADYKRITLKVHAPYRNIS  102
SEQ ID NO: 20   SSYSQRAQLLKDQLFLGKAALQITDVRLQDAGVYRCLIGYGGADYKRITLKVHAPYRNIS  120
SEQ ID NO: 21   ----------LIGYGGADYKRITLKVHAPYRNIS                            24
SEQ ID NO: 22   SSYSQRAQLLKDQLFLGKAALQITDVRLQDAGVYRCLIGYGGADYKRITLKVHAPYRNIS  120
SEQ ID NO: 32   SSYSQRAQLLKDQLFLGKAALQITDVRLQDAGVYCCLIGYGGADYKRITLKVHAPYRNIS  120
                                                  *************************

SEQ ID NO: 19   QRISVDPVTSEHELMCQAEGYPEAEVIWTSSDHRVLSGKTTITNSNREEKLFNVTSTLNI  162
SEQ ID NO: 20   QRISVDPVT----------                                          129
SEQ ID NO: 21   QRISVDPVT----------                                          33
SEQ ID NO: 22   QRISVDPVTSQ----------                                        131
SEQ ID NO: 32   QRISVDPVTSEHELMCQAEGYPEAEVIWTSSDHRVLSGKTTITNSNREEKLFNVTSTLNI  180
                *********
```

FIG. 13A

```
SEQ ID NO: 19    NATANEIFYCTFQRSGPEENNTAELVIPERLPVPASERTHFMILGPFGGGQGGGGSGGQG    222
SEQ ID NO: 20    -------------------------------------------------SGGGGQGGGGSGGQG    143
SEQ ID NO: 21    -------------------------------------------------SGGGGQGGGGSGGQG    47
SEQ ID NO: 22    --------------------------------------------------------GGG    134
SEQ ID NO: 32    NATANEIFYCTFQRSGPEENNTAELVIPERLPVPASERTHFMILGPFGGGQGGGGSGGQG    240
                                                                         *  *

SEQ ID NO: 19    GGGGDCPKCPAPEMLGGPSVFIFPPKPKDTLLIARTPEVTCVVVDLDPEDPEVQISWFVD    282
SEQ ID NO: 20    GGGGDCPKCPAPEMLGGPSVFIFPPKPKDTLLIARTPEVTCVVVDLDPEDPEVQISWFVD    203
SEQ ID NO: 21    GGGGDCPKCPAPEMLGGPSVFIFPPKPKDTLLIARTPEVTCVVVDLDPEDPEVQISWFVD    107
SEQ ID NO: 22    SGGQDCPKCPAPEMLGGPSVFIFPPKPKDTLLIARTPEVTCVVVDLDPEDPEVQISWFVD    194
SEQ ID NO: 32    GGGGDCPKCPAPEMLGGPSVFIFPPKPKDTLLIARTPEVTCVVVDLDPEDPEVQISWFVD    300
                 .**.************************************************************

SEQ ID NO: 19    GKQMQTAKTQPREEQFNGTYRVVSVLPIGHQDWLKGKQFTCKVNNKALPSPIERTISKAR    342
SEQ ID NO: 20    GKQMQTAKTQPREEQFNGTYRVVSVLPIGHQDWLKGKQFTCKVNNKALPSPIERTISKAR    263
SEQ ID NO: 21    GKQMQTAKTQPREEQFNGTYRVVSVLPIGHQDWLKGKQFTCKVNNKALPSPIERTISKAR    167
SEQ ID NO: 22    GKQMQTAKTQPREEQFNGTYRVVSVLPIGHQDWLKGKQFTCKVNNKALPSPIERTISKAR    254
SEQ ID NO: 32    GKQMQTAKTQPREEQFNGTYRVVSVLPIGHQDWLKGKQFTCKVNNKALPSPIERTISKAR    360
                 ************************************************************
```

FIG. 13B

```
SEQ ID NO: 19   GQAHQPSVYVLPPSREELSKNTVSLTCLIKDFFPPDIDVEWQSNGQQEPESKYRTTPPQL   402
SEQ ID NO: 20   GQAHQPSVYVLPPSREELSKNTVSLTCLIKDFFPPDIDVEWQSNGQQEPESKYRTTPPQL   323
SEQ ID NO: 21   GQAHQPSVYVLPPSREELSKNTVSLTCLIKDFFPPDIDVEWQSNGQQEPESKYRTTPPQL   227
SEQ ID NO: 22   GQAHQPSVYVLPPSREELSKNTVSLTCLIKDFFPPDIDVEWQSNGQQEPESKYRTTPPQL   314
SEQ ID NO: 32   GQAHQPSVYVLPPSREELSKNTVSLTCLIKDFFPPDIDVEWQSNGQQEPESKYRTTPPQL   420
                ************************************************************

SEQ ID NO: 19   DEDGSYFLYSKLSVDKSRWQRGDTFICAVMHEALHNHYTQESLSHSPG   450
SEQ ID NO: 20   DEDGSYFLYSKLSVDKSRWQRGDTFICAVMHEALHNHYTQESLSHSPG   371
SEQ ID NO: 21   DEDGSYFLYSKLSVDKSRWQRGDTFICAVMHEALHNHYTQESLSHSPG   275
SEQ ID NO: 22   DEDGSYFLYSKLSVDKSRWQRGDTFICAVMHEALHNHYTQESLSHSPG   362
SEQ ID NO: 32   DEDGSYFLYSKLSVDKSRWQRGDTFICAVMHEALHNHYTQESLSHSPG   468
                ***********************************************
```

FIG. 13C

PD-L1 ANALOG FUSION PROTEINS FOR ANTIGEN SPECIFIC IMMUNOTHERAPY AND METHODS OF USE

CROSS-REFERENCE TO RELATED APPLICATIONS

The present application is a continuation of U.S. patent application Ser. No. 19/071,424, filed Mar. 5, 2025, which claims the priority benefit of U.S. Provisional Patent Application Ser. No. 63/568,097, filed Mar. 21, 2024, U.S. Provisional Patent Application Ser. No. 63/568,116, filed Mar. 21, 2024, U.S. Provisional Patent Application Ser. No. 63/568,130, filed Mar. 21, 2024, U.S. Provisional Patent Application Ser. No. 63/568,146, filed Mar. 21, 2024, and U.S. Provisional Patent Application Ser. No. 63/568,173, filed Mar. 21, 2024, each entitled PD-L1 ANALOG FUSION PROTEINS FOR ANTIGEN SPECIFIC IMMUNOTHERAPY AND METHODS OF USE, and each of which is incorporated by reference herein in its entirety.

SEQUENCE LISTING

The following application contains a sequence listing filed electronically as a Standard ST.26 compliant XML file entitled "ABC-062USCNT.xml," created on Oct. 6, 2025, as 36,758 bytes in size, the entire contents of which are incorporated by reference herein.

TECHNICAL FIELD

The present technology relates to fusion proteins comprising a PD-L1 protein or an analog thereof linked to Fc fragments and their use as a treatment for cancers, tumors or other diseases associated with expression of the PD-L1 protein in dogs.

BACKGROUND

The following description of the background is provided simply as an aid in understanding the present technology and is not admitted to describe or constitute prior art to the present technology.

Fc Fusion Proteins

Fc fusion proteins are comprised of a species-specific immunoglobin Fc domain that is linked to another peptide such as a protein or peptide with therapeutic potential. As used herein, the terms "fusion protein" and "Fc fusion protein" refer to a protein comprising more than one part, for example from different sources (e.g., different proteins, polypeptides, cells, etc.), that are covalently linked through peptide bonds. Fc fusion proteins are preferably covalently linked by (i) connecting the genes that encode for each part into a single nucleic acid molecule and (ii) expressing in a host cell (e.g., HEK cell or CHO cell) the protein for which the nucleic acid molecule encodes. The fully recombinant synthesis approach is preferred over methods in which the therapeutic protein and Fc fragments are synthesized separately and then chemically conjugated. The chemical conjugation step and subsequent purification process increase the manufacturing complexity, reduce product yield, and increase cost.

The terms "Fc fragment," "Fc region," "Fc domain," or "Fc polypeptide," are used herein to define a C-terminal region of an immunoglobulin heavy chain. The Fc fragment, region, domain, or polypeptide may be a native sequence Fc region or a variant/mutant Fc region. Although the boundaries of the Fc region of an immunoglobulin heavy chain may vary, they generally comprise some or all of the hinge region of the heavy chain, the CH2 region of the heavy chain, and the CH3 region of the heavy chain. The hinge region of an Fc fragment comprises amino acid sequences that connect the CH1 domain of the heavy chain to the CH2 region of the heavy chain and contains one or more cysteines that form one or more interheavy chain disulfide bridges to form a homodimer of an Fc fusion protein from two identical but separate monomers of the Fc fusion protein. The hinge region may comprise all or part of a naturally occurring amino acid sequence or a non-naturally occurring amino acid sequence.

The presence of the Fc domain increases the plasma half-life due to its interaction with the neonatal Fc-receptor (FcRn) in addition to slower renal clearance of the Fc fusion protein due to the large molecule size, resulting in in vivo recycling of the molecule achieving prolonged activity of the linked peptide and improved solubility and stability of the Fc fusion protein molecule. The Fc domain also enables Fc fusion proteins to interact with Fc receptors on immune cells. In some examples, the therapeutic protein or peptide is linked to the immunoglobin Fc domain via a linker. The therapeutic protein or peptide and linker replace the variable region of an antibody while keeping the Fc region intact.

An Fc receptor (FcR) refers to a receptor that binds to an Fc fragment or to the Fc region of an antibody. In examples, the FcR is a native sequence of a mammalian FcR, and the FcR is one which binds an Fc fragment or the Fc region of an IgG antibody (a gamma receptor) and includes without limitation, receptors of the Fc(gamma) receptor I, Fc(gamma) receptor Ia, Fc(gamma) receptor IIb, and Fc(gamma) receptor III subclasses (and their species-specific equivalents, e.g., canine-specific equivalents), including allelic variants and alternatively spliced forms of these receptors. "FcR" also includes the neonatal receptor, FcRn, which is responsible for the transfer of maternal IgG molecules to the fetus and is also responsible for the prolonged in vivo elimination half-lives of antibodies and Fc-fusion proteins in vivo. In examples, FcR of human origin are used in vitro (e.g., in an assay) to measure the binding of Fc fusion proteins comprising Fc fragments of any mammalian origin so as to assess their FcR binding properties. Those skilled in the art will understand that mammalian FcR from one species (e.g., FcR of human origin) are sometimes capable of in vitro binding of Fc fragments from a second species (e.g., FcR of canine origin).

Programmed Death-Ligand 1 (PD-L1)

Due to increased lifespan in dogs, cancer has recently surpassed infectious disease as the leading cause of death in dogs over the age of two years. According to a report, 27% of overall dog deaths are due to cancer (Adams et al., (2010). *Methods and mortality results of a health survey of purebred dogs in the UK. J small Anim Pract* 51:512-524). Current clinical treatments for cancer in dogs include surgical, chemotherapeutic and radiation therapies as is the case in humans. However, in the case of some dog cancers it can be difficult to treat them conventional therapeutic methods because of the severe stress, adverse effects and/or difficulties in approaching the tumor sites. In addition, the sensitivities to chemo/radiotherapies can differ depending on the tumor types. Therefore, it is worth investigating the efficacy of novel approaches against canine cancer, including immunotherapy, as this may lead to the development of more effective therapies that can induce tumor remission.

Programmed Cell Death Receptor 1, also referred to as Programmed Death Receptor 1 (PD-1) is an immunoinhibitory receptor that is expressed on the surface of immune cells, such as activated T cells and B cells. The PD-1 receptor interacts with Programmed Death-Ligand 1 (PD-L1) which is a protein that is expressed on the surface of certain cells, including some normal cells and cancer cells. PD-L1 guards against autoimmunity. In examples, PD-L1 binding with the PD-1 receptor promotes apoptosis (programmed cell death) of antigen-specific T-cells in lymph nodes (Han. Y., Liu. D., and Li. L., (2020). *PD-1/PD-L1 pathway: current researches in cancer. Am J Cancer Res.* 10(3): 727-742). In examples, PD-L1 binding with the PD-1 receptor on antigen specific T-cells may cause the T cells to become quiescent, lowering the extent of the immune response. The interaction between PD-1 and PD-L1 may serve as an immune checkpoint mechanism that helps prevent the immune system from attacking normal, healthy cells.

SUMMARY OF THE PRESENT TECHNOLOGY

Described herein are fusion proteins, each comprising a respective Programmed Death-Ligand 1 (PD-L1) protein fragment and an Fc fragment, wherein the PD-L1 fragment and the Fc fragment are connected by a peptide linker. In one or more embodiments, the PD-L1 fragment comprises a PD-L1 analog comprising a functional fragment, analog, or variant/mutant thereof. In one or more embodiments, the Fc fragment comprises a sequence or functional fragment of SEQ ID NO: 1.

```
                                    (SEQ ID NO: 1)
DCPKCPAPEMLGGPSVFIFPPKPKDTLLIARTPEVTCVVVDLDPEDPEVQ

ISWFVDGKQMQTAKTQPREEQFNGTYRVVSVLPIGHQDWLKGKQFTCKVN

NKALPSPIERTISKARGQAHQPSVYVLPPSREELSKNTVSLTCLIKDFFP

PDIDVEWQSNGQQEPESKYRTTPPQLDEDGSYFLYSKLSVDKSRWQRGDT

FICAVMHEALHNHYTQESLSHSPG.
```

In one or more embodiments, the peptide linker comprises the sequence

```
                                    (SEQ ID NO: 6)
GGGGQGGGSGGQGGGG.
```

In one or more embodiments, the fusion protein comprises a PD-L1 analog and an Fc fragment, wherein the PD-L1 analog and the Fc fragment are connected by a peptide linker, wherein the PD-L1 analog comprises a PD-L1 fragment of SEQ ID NO: 23, or a functional fragment, analog, or variant/mutant thereof.

```
                                    (SEQ ID NO: 23)
LIGYGGADYKRITLKVHAPYRNISQRISVDPVTSEHELMCQAEGYPEAEV

IWTSSDHRVLSGKTTITNSNREEKLFNVTSTLNINATANEIFYCTFQRSG

PEENNTAELVIPERLPVPASERTHFMILGPF.
```

In one or more embodiments, the fusion protein comprises, consists essentially or even consists of a sequence of SEQ ID NO: 24.

```
                                    (SEQ ID NO: 24)
LIGYGGADYKRITLKVHAPYRNISQRISVDPVTSEHELMCQAEGYPEAEV

IWTSSDHRVLSGKTTITNSNREEKLFNVTSTLNINATANEIFYCTFQRSG

PEENNTAELVIPERLPVPASERTHFMILGPFGGGGQGGGSGGQGGGGDC

PKCPAPEMLGGPSVFIFPPKPKDTLLIARTPEVTCVVVDLDPEDPEVQIS

WFVDGKQMQTAKTQPREEQFNGTYRVVSVLPIGHQDWLKGKQFTCKVNNK

ALPSPIERTISKARGQAHQPSVYVLPPSREELSKNTVSLTCLIKDFFPPD

IDVEWQSNGQQEPESKYRTTPPQLDEDGSYFLYSKLSVDKSRWQRGDTFI

CAVMHEALHNHYTQESLSHSPG.
```

In embodiments, a fusion protein of the present disclosure comprises a dimer, wherein the dimer comprises two identical monomers bound together via disulfide bonds; e.g., the fusion protein is a homodimer.

In one or more embodiments, the Fc fragment is glycosylated.

Also described herein are immunogenic compositions which comprise or consist essentially of a fusion protein(s) according to any embodiments or combinations of embodiments described herein and a pharmaceutically acceptable carrier. In one or more embodiments, the fusion protein is dispersed in the carrier. In one or more embodiments, the immunogenic composition further comprises an adjuvant.

As described herein, the fusion protein(s) or immunogenic composition(s) according to any embodiments or combinations of embodiments described herein can be used in treatment for cancers, tumors or other diseases associated with the expression of the PD-L1 protein in dogs.

In some embodiments the duration of response to dose levels varying from 1 μg to 100 μg of the fusion protein(s) or immunogenic composition(s) is expected to demonstrate increasing anti-PD-L1 protein antibody titers at all dose levels after 1, 2, and 3 doses up to at least 56 days post vaccination.

BRIEF DESCRIPTION OF THE DRAWINGS

FIG. 2 illustrates a side-by-side sequence comparison of the human PD-L1 of SEQ ID NO: 2 and the canine PD-L1 of SEQ ID NO: 3.

FIG. 3 illustrates a side-by-side sequence comparison of the human PD-1 of SEQ ID NO: 4 and the canine PD-1 of SEQ ID NO: 5.

FIG. 4 illustrates a side-by-side sequence comparison of the truncated human PD-L1 analogs of SEQ ID NO: 8, SEQ ID NO: 9, SEQ ID NO: 10 and SEQ ID NO: 11.

FIG. 5A, FIG. 5B and FIG. 5C illustrate a side-by-side sequence comparison of the PD-L1 fusion proteins of SEQ ID NO: 15, SEQ ID NO: 16, SEQ ID NO: 17, and SEQ ID NO: 18.

FIG. 6A and FIG. 6B, illustrate a side-by-side sequence comparison of the canine PD-L1 analogs of SEQ ID NO: 12, SEQ ID NO: 13, SEQ ID NO: 14 and SEQ ID NO: 23.

FIG. 7A, FIG. 7B and FIG. 7C illustrate a side-by-side sequence comparison of the PD-L1 fusion proteins of SEQ ID NO: 19, SEQ ID NO: 20, SEQ ID NO: 21, SEQ ID NO: 22, and SEQ ID NO: 24.

FIG. 8A and FIG. 8B, illustrate a side-by-side sequence comparison of the canine PD-L1 analogs of SEQ ID NO: 12, SEQ ID NO: 13, SEQ ID NO: 14 and SEQ ID NO: 25.

FIG. 9A, FIG. 9B and FIG. 9C illustrate a side-by-side sequence comparison of the PD-L1 fusion proteins of SEQ ID NO: 19, SEQ ID NO: 20, SEQ ID NO: 21, SEQ ID NO: 22, and SEQ ID NO: 26.

FIG. 10A, FIG. 10B and FIG. 10C illustrate a side-by-side sequence comparison of the PD-L1 fusion proteins of SEQ ID NO: 19, SEQ ID NO: 20, SEQ ID NO: 21, SEQ ID NO: 22, and SEQ ID NO: 27.

FIG. 11A, FIG. 11B and FIG. 11C illustrate a side-by-side sequence comparison of the PD-L1 fusion proteins of SEQ ID NO: 19, SEQ ID NO: 20, SEQ ID NO: 21, SEQ ID NO: 22, and SEQ ID NO: 28.

FIG. 12A and FIG. 12B, illustrate a side-by-side sequence comparison of the canine PD-L1 analogs of SEQ ID NO: 12, SEQ ID NO: 13, SEQ ID NO: 14 and SEQ ID NO: 31.

FIG. 13A, FIG. 13B and FIG. 13C illustrate a side-by-side sequence comparison of the PD-L1 fusion proteins of SEQ ID NO: 19, SEQ ID NO: 20, SEQ ID NO: 21, SEQ ID NO: 22, and SEQ ID NO: 32.

DETAILED DESCRIPTION

Figure 1:
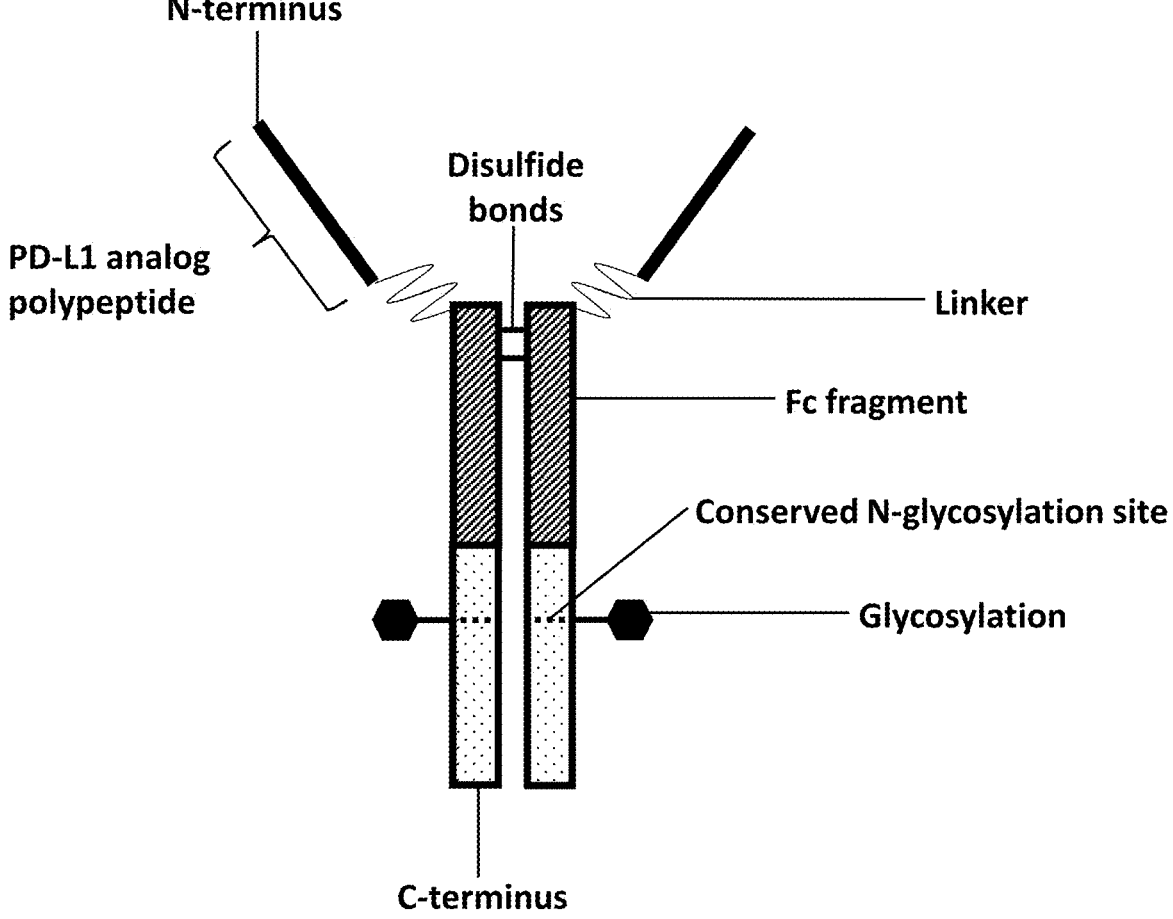
FIG. 1 shows a schematic representation of a PD-L1 analog-Fc fusion protein homodimer. The glycosylation site shown is the conserved natural glycosylation site on the Fc fragment (glycosylation that may occur on the PD-L1 analog polypeptide is not shown).

PD-1 is an immune checkpoint and guards against autoimmunity through two mechanisms. First, it promotes apoptosis (programmed cell death) of antigen-specific T-cells in lymph nodes, and/or may cause the T cells to become quiescent, lowering the extent of the immune response. Second, it reduces apoptosis in regulatory T cells (anti-inflammatory, suppressive T cells), and/or may cause the T cells to become quiescent, lowering the extent of the immune response. Programmed Death-1 Ligand-1 (PD-L1, CD274, B7-H1) has been identified as the ligand for the immunoinhibitory receptor Programmed Death-1 (PD-1/PDCD1) cell surface receptor on T cells (Maekawa et al., (2014). *Expression of PD-L1 on canine tumor cells and enhancement of IFN-γ production from tumor-infiltrating cells by PD-L1 blockade. doi.org/*10.1371/journal-.pone.0098415)

Most cells express PD-L1 on the cell surface. Some cells have been shown to express PD-L1 at concentrations at or above that expressed by normal healthy cells. In examples, some cancerous cells have been shown to express PD-L1 at concentrations at or above that expressed by normal healthy cells. Cancerous cells may be cancerous tumor cells or may be cells that are not part of a tumor, for example metastasized cancer cells which appear in different regions of the body. When cancer cells expressing PD-L1 bind to PD-1 on activated T cells and B cells, the PD-L1 may increase apoptosis of antigen specific T cells, and/or PD-L1 binding with the PD-1 receptor on antigen specific T-cells may cause the T cells to become quiescent, suppressing an immune response against the cells expressing PD-L1.

Some cells associated with cancer, for example cancer tumor cells or cancers that have metastasized, have been shown to express PD-L1. When cancer cells expressing PD-L1 bind to PD-1 on activated T cells and B cells, the PD-L1 may increase apoptosis of antigen specific T cells and/or may cause the T cells to become quiescent, lowering the extent of the immune response, suppressing an immune response against the cells expressing PD-L1.

Cancer tumors exploit the immune checkpoint mechanism to inhibit the ability of T cells to recognize and attack cancer cells. This interaction creates an immunosuppressive cancerous tumor or metastasized cancer cell microenvironment that evades the immune system. Treatments that target PD-L1 with anti-PD-L1 antibodies have been shown to be effective against cancers or other diseases associated with the over expression of the PD-L1 protein.

Some cells associated with cancer and cancer tumors exploit the immune checkpoint mechanism to inhibit the ability of T cells to recognize and attack the cancer cells. This interaction creates an immunosuppressive microenvironment that allows the cancer cells to evade the immune system. Some cancer cells may express PD-L1 at concentrations comparable to that expressed by normal healthy cells. These cancers cells may also evade the immune system exploiting the immune checkpoint mechanism. This may be to a lesser extent than cancer cells which overexpress PD-L1, however as cancer cells may replicate rapidly, cancer cells that express PD-L1 at concentrations comparable to that expressed by normal healthy cells can also be effectively treated by treatments that target PD-L1. Therapeutic antibodies targeting immune checkpoint molecules such as PD-1 and PD-L1 have been used as an effective treatment in cancer by reinvigorating immune responses against cancers by preventing or lessening the inhibitory signal response (Iwai et al., (2017). *Cancer immunotherapies targeting the PD-1 signaling pathway. J. Biomed Sci.* 24:26).

Treatments that target PD-L1 with anti-PD-L1 antibodies have been shown to be an effective treatment for some cancers or other diseases associated with the expression of the PD-L1 protein. Therapeutic antibodies targeting immune checkpoint molecules such as PD-1 and PD-L1 have been used as an effective treatment in cancer treatment by reinvigorating immune responses against cancers (Iwai et al., (2017). *Cancer immunotherapies targeting the PD-1 signaling pathway. J. Biomed Sci.* 24:26).

A recent development in immunotherapy are immune checkpoint blockers (ICB), which have shown success in oncology thanks to their broad activity on several types of cancer tumors and cancer cells, the durability of their responses and their capacity for treatment of metastatic chemotherapy resistant cancer tumors in humans. To date, four ICBs targeting the PD-1/PD-L1 checkpoint have been approved by the US Food and Drug Administration, (Abdin et al., (2018). *Tackling Cancer Resistance by Immunotherapy: Updated Clinical Impact and Safety of PD-1/PD-L1 Inhibitors. Cancers* 10 32). These consist of Pembrolizumab, Nivolumab, Atezolizumab, and Avelumab. PD-L1 has been shown to be expressed on a number of human cancerous tumors and is inducible by IFN-γ in the majority of PD-L1 negative tumor cell lines (Iwai et al., (2002). *Involvement of PD-L1 on tumor cells in the escape from host immune system and tumor immunotherapy by PD-L1 blockade. Proc. Natl. Acad. Sci. U.S.A.* 99: 12293-12297). ICBs targeting PD-L1 have been shown to be effective in melanoma, non-small cell lung cancer (NSCLC) and renal carcinoma in canines (Maekawa et al., (2014). *Expression of PD-L1 on canine tumor cells and enhancement of IFN-γ production from tumor-infiltrating cells by PD-L1 blockade.* doi.org/10.1371/journal.pone.0098415).

Cancer cells expressing PD-L1 have been identified in a number of primary human tumor biopsies. These include but are not limited to cancers of the lung, liver, ovary, cervix, skin, colon, glioma, bladder, breast, kidney, esophagus, stomach, oral squamous cell, urothelial cell, and pancreas, as well as tumors of the head and neck (Brown et al., (2003). *Blockade of programmed death-1 ligands on dendritic cells enhances T cell activation and cytokine production. J. Immunol.* 170:1257-1266.; Dong et al., (2002). *Tumor-associated B7-H1 promotes T-cell apoptosis: a potential mechanism of immune evasion. Nat. Med.* 8: 793-800; Wintterle et al., (2003). *Expression of the B7-related molecule B7-H1 by glioma cells: a potential mechanism of immune paralysis. Cancer Res.* 63: 7462-7467; Strome et al., (2003). *B7-H1 blockade augments adoptive T-cell immunotherapy for squamous cell carcinoma. Cancer Res.,* 63: 6501-6505; Thompson et al., (2006). *Tumor B7-H1 Is Associated with Poor Prognosis in Renal Cell Carcinoma Patients with Long-term Follow-up. Cancer Res.* 66: 3381-5; Thompson et al., (2007). *PD-1 is expressed by tumor-infiltrating immune cells and is associated with poor outcome for patients with renal cell carcinoma. Clin. Cancer Res.* 13: 1757-1761;Nomi et al., (2007). *Clinical signifi-*

*cance and therapeutic potential of the programmed death-1 ligand/programmed death-1 pathway in human pancreatic cancer. Clin. Cancer Res.* 13: 2151-2157).

Canines have a PD-L1 protein which is structurally similar to human PD-L1 protein. This can be seen in a sequence comparison of human PD-L1 (SEQ ID NO: 2) against a canine PD-L1 (SEQ ID NO: 3) in FIG. 2. Therefore, treatments targeting the PD-1/PD-L1 checkpoint will likely be similarly effective. However, there are sufficient structural differences between human and canine PD-L1 protein that it is unlikely that an anti-human-PD-L1 antibody will bind to canine PD-L1 protein, so new canine-centric therapies and approaches to solving the problem of cancer in canines are urgently needed. Canine cancers share many of the hallmarks of human cancers including cancerous tissue location and tumor progression and also share many of the same medical treatment regime options as surgical tumor removal, chemotherapy, and irradiation. In canine cancerous tumors, surgical removal of the cancer, or amputation of the affected body part are commonly practiced treatments due to cost. Other less invasive treatment options such as chemotherapy and radiotherapy, which may be the only options for metastasized cancer, may be prohibitively expensive and lead to euthanasia. Treatments that target the PD-1/PD-L1 checkpoint in canines will likely be an effective therapeutic approach to cancerous medical issues in dogs.

The required dosing regimen for a monoclonal antibody PD-L1 treatment incurs considerable monetary and manufacturing costs for producing the drug which get passed on to patients or pet owners, making the treatment unaffordable in many cases. Monoclonal antibodies require very large dosages (e.g., 10 mg/kg of body weight in canines), have a limited half-life, and require regular redosing (e.g., every two weeks for gilvetmab (a monoclonal PD-L1 treatment for canines)). Gilvetmab must also be administered intravenously. Exogenously administered monoclonal antibodies may also become less efficacious over time if the body becomes immune to them (e.g., through the development of anti-drug antibodies). A lower cost treatment regime with an easier administration option (e.g., treatment via a subcutaneous (s.c.) or intramuscular (i.m.) rather than intravenous (i.v.) injection) would offer a more efficacious and cost effective treatment for canines afflicted with cancers and other diseases associated with expression of PD-L1.

Production of a therapeutic vaccine in the form of a PD-L1 analog-Fc fusion protein combined optionally with an adjuvant for use as a treatment for cancer will not have these drawbacks. A vaccine approach to target PD-L1 in the body as a treatment for cancer will require minimal intervention as the objective is to stimulate the body through an initial or priming dosing regimen to manufacture its own endogenously-produced antibodies to target PD-L1 expressed on cancer cells, and to allow the body's own immune system to attack the cancer cells. After the initial priming dosing regime, each treatment will therefore be long-acting and only require small doses as a vaccine therapy spaced at greater intervals to stimulate an immune reaction. Therefore, there is a considerable cost advantage as the scale of manufacturing of a low-dose therapeutic vaccine will be greatly reduced compared to a monoclonal antibody, thereby making the treatment accessible to more patients. The vaccine approach, with an initial priming dosing regimen followed up with additional doses or booster injections spaced farther apart, may be used to stimulate further immune reaction and endogenous antibody production. In addition, a vaccine that stimulates the body to produce endogenous antibodies is likely to create polyclonal antibodies, with the potential of a more robust response targeting PD-L1 expressed on the surface of cancer cells in the body (Huang et al., (2021). *Pan-cancer analysis of CD274 (PD-L1) mutations in 314,631 patient samples and subset correlation with PD-L1 protein expression. Journal for ImmunoTherapy of Cancer.* 9: e002558. *doi:* 10.1136/*jitc*-2021-002558).

The present disclosure is directed to methods for making and using novel PD-L1 based Fc fusion proteins (PD-L1 analog-Fc fusion proteins) which allow for the cost-effective production of vaccines to induce a patient to produce antibodies against PD-L1 (e.g., a patient's endogenously produced PD-L1) with the effect of triggering the immune system to attack cancer cells or other diseases associated with the expression of the PD-L1 protein. The present disclosure is specifically directed to methods for making and using PD-L1 analog-Fc fusion proteins for use as a therapeutic vaccine which is efficacious for causing patients to create anti-PD-L1 antibodies to the PD-L1 protein, for example to target PD-L1 on the surface of cancer cells thus preventing them from binding to the PD-1 receptors on T cells (which would prevent suppression of T cells and in consequence increase the immune reaction against the cancer cells). The present disclosure is directed to the specification of canine PD-L1 analog-Fc fusion protein amino acid sequences comprising a PD-L1 analog or PD-L1 analog fragment linked via a linker to an Fc fragment. These PD-L1 analog-Fc fusion proteins are directed towards a treatment for dogs affected by cancers, tumors or other diseases associated with expression of the PD-L1 protein in dogs. In addition, the PD-L1 analog-Fc fusion protein may optionally be co-administered with an adjuvant, e.g., Montanide™ ISA 720 (Seppic Inc., New Jersey, United States), Quil-A™ (Croda, Frederikssund, Denmark), Sepivac SWE™ (Seppic Inc., New Jersey, United States)).

In an example, a pharmaceutical composition of a novel PD-L1 analog-Fc fusion protein therapeutic vaccine is administered to patients requiring treatment for cancer. In examples, the novel PD-L1 analog-Fc fusion protein has the effect of stimulating the patient to produce humoral immunity, for example generating increased levels of IgG antibodies compared to an untreated patient, where the resulting endogenously-produced antibodies bind PD-L1 on the surface of cancer cells. In examples, the endogenous antibodies will be created and build up after an initial administration of the PD-L1 analog fusion protein as a part of a priming regime (e.g., there may be a short time lag to initially establish antibodies, e.g., 7-14 days). Subsequent administrations of adjuvanted or non-adjuvanted boosters after the initial priming regime will lead to rapid onset and production of antibodies (e.g., within days). When the immune system develops a robust antibody response to PD-L1, cancer cells that express PD-L1 are no longer protected by the immune checkpoint mechanism and are targeted by T cells, thereby acting as a treatment for cancer or other diseases associated with the expression of the PD-L1 protein through the endogenous production of antibodies in the patient.

There are drawbacks with existing monoclonal antibody therapy treatments for cancer, including giving regular administrations and large doses, since antibodies are given exogenously and not produced by the patient's immune system endogenously. The necessity of frequent administration by IV injection, (which requires a patient to be still for a considerable length of time and may require sedation of the canine) is inconvenient for owners and distressing for pets and may lead to non-compliance with treatment regimes.

The large doses and frequent administration of monoclonal antibody therapy will also have significant cost implications for the pet owners.

The dose volume of a monoclonal antibody can be large and highly variable as it will be dependent on the body weight of the pet, requiring different Stock Keeping Units (SKUs) to treat a population of patients that have widely varying body weights, thereby further increasing manufacturing costs and treatment costs for owners. A therapeutic vaccine-based approach to target PD-L1 in the body to treat cancer greatly simplifies the cost and burden on pet owners, as the dose given may be roughly independent of body weight, thereby allowing for fewer SKUs to manage as a product. Additionally, the vaccine can be administered to a patient via a simple subcutaneous (s.c.) or intramuscular (i.m.) injection. Further, the treatment stimulates the body to manufacture its own antibodies against the administered PD-L1 analog-Fc fusion protein, which can then bind and neutralize the PD-L1, thereby reducing the potential for PD-L1 to bind to PD-1 in vivo. Because antibodies are produced endogenously, fewer treatments are required after the initial priming regime. The body also may create polyclonal antibodies in response to the vaccine, with the potential of providing a more robust response to treat cancers or other diseases linked to or due to the expression of the PD-L1 protein in the body.

Equivalents and Definitions

As used herein, the articles "a" and "an" refer to one or more than one, e.g., to at least one of the grammatical objects of the article. The use of the words "a" or "an" when used in conjunction with the term "comprising" herein may mean "one," but it is also consistent with the meaning of "one or more," "at least one," and "one or more than one." As used herein, the phrase "and/or," when used in a list of two or more items, means that any one of the listed items can be employed by itself or any combination of two or more of the listed items can be employed. For example, if a composition is described as containing or excluding components A, B, and/or C, the composition can contain or exclude A alone; B alone; C alone; A and B in combination; A and C in combination; B and C in combination; or A, B, and C in combination.

As used herein, "about" and "approximately" generally mean an acceptable degree of error for the quantity measured given the nature or precision of the measurements.

As used herein, an amount of a molecule, compound, conjugate, or substance effective to treat a disorder (e.g., a disorder described herein), "therapeutically effective amount," or "effective amount" refers to an amount of the molecule, compound, conjugate, or substance which is effective, upon single or multiple dose administration(s) to a patient, in treating a patient, or in curing, alleviating (e.g., alleviating associated symptoms such as pain or shrinking the size of a tumor), relieving or improving a patient with a condition or disorder (e.g., a disorder described herein) beyond that expected in the absence of such treatment.

As used herein, the term "analog" refers to a compound or conjugate (e.g., a compound or conjugate as described herein) having a chemical structure similar to that of another compound or conjugate but differing from it in at least one aspect.

As used herein, the term "antigen" (Ag) or "antigenic agent" refers to any substance that causes a patient's immune system to produce antibodies against it. An antigen may be a substance from the environment, such as chemicals, bacteria, viruses, or pollen, or an antigen may also be inside the body. In some cases, the antigen is endogenously-produced (e.g., a self-antigen). An example of a self-antigen is the PD-L1 protein. An antigen (e.g., PD-L1) or an antigen analog (e.g., PD-L1 analog) may also be covalently linked to another protein (e.g., an Fc fragment).

As used herein, the term "antibody" or "antibody molecule" refers to an immunoglobulin molecule (Ig), or immunologically active portions of an immunoglobulin (Ig) molecule, i.e., a molecule that contains an antigen binding site that specifically binds, e.g., immunoreacts with, an antigen or a self-antigen. As used herein, the term "antibody domain" refers to a variable or constant region of an immunoglobulin. It is documented in the art that antibodies comprise several classes, for example IgA, IgM, or IgG in the case of mammals (e.g., dogs). Classes of mammalian IgG immunoglobulins can be further classified into different isotypes, such as IgGA, IgGB, IgGC and IgGD for dogs. Those skilled in the art will recognize that immunoglobulin isotypes of a given immunoglobulin class will comprise different amino acid sequences, structures, and functional properties from one another (e.g., different binding affinities to Fc (gamma) receptors or PD-1 protein). "Specifically binds" or "immunoreacts with" means that the antibody reacts with one or more antigenic determinants of the desired antigen and has a lower affinity for other polypeptides, e.g., does not react with other polypeptides.

As used herein, the term "PD-L1 analog" refers to a protein comprising a peptide derived from or consisting of all or a portion of a PD-L1 protein, which may have none, one or more than one amino acid deletions, mutations, or additions. For example, a PD-L1 analog may be a native (wild-type) PD-L1 protein with no changes or mutations, a native PD-L1 protein comprising an additional peptide sequence combined with the native PD-L1 protein, or a native PD-L1 protein with none, one or more than one amino acid deletions, mutations, or additions from the native PD-L1 protein. In examples, a PD-L1 analog may comprise a portion (e.g., a fragment) or truncated section of a native PD-L1 protein, and the truncated section of the native PD-L1 protein may have none, one or more than one amino acid deletions, mutations, or additions. In examples, a PD-L1 analog may comprise a portion of an artificial sequence combined with all or a portion of a native PD-L1 protein, which may have none, one or more than one amino acid deletions, mutations, or additions. As used herein the term PD-L1 analog may comprise all or a portion of a PD-L1 precursor protein, which may have none, one or more than one amino acid deletions, mutations, or additions. In examples, a PD-L1 analog may comprise a human PD-L1 protein as given in SEQ ID NO: 2. In examples the PD-L1 analog may comprise a canine PD-L1 protein as given in SEQ ID NO: 3. As used herein, the term "PD-L1 analog" may refer to a polypeptide that contains a portion of the canine PD-L1 protein as given in SEQ ID NO: 3. In examples, the PD-L1 analog may be linked to an Fc fragment or analog thereof, as illustrated in FIG. 1. In examples, a PD-L1 analog may or may not have one or more amino acid mutations as compared to a non-mutated PD-L1 (e.g., a PD-L1 sequence that is homologous to human PD-L1 or canine PD-L1).

As used herein, the term "dimer" refers to a protein or a fusion protein comprising two polypeptides linked covalently. In embodiments, two identical polypeptides are linked covalently (e.g., via disulfide bonds) forming a "homodimer" (diagrammatically represented in FIG. 1, which is an illustration of a PD-L1 analog-Fc fusion protein homodimer). Referring to FIG. 1 in more detail, the PD-L1 analog-Fc fusion protein polypeptide is connected via a linker to an Fc fragment. Disulfide bonds (the total number of disulfide bonds in actuality may be greater or less than the number shown in FIG. 1) create a homodimer from two identical Fc fusion proteins. The novel PD-L1 analog-Fc fusion protein homodimer may be encoded by a single nucleic acid molecule, wherein the homodimer is made recombinantly inside a cell by first forming novel PD-L1 analog-Fc fusion protein monomers and by then assembling two identical novel PD-L1 analog-Fc fusion protein monomers into the homodimer upon further processing inside the cell.

As used herein, the terms "multimer," "multimeric," or "multimeric state" refer to non-covalent, associated forms of Fc fusion protein dimers that may be in equilibrium with Fc fusion protein dimers or may act as permanently aggregated versions of Fc fusion protein dimers (e.g., dimers of Fc fusion protein homodimers, trimers of Fc fusion protein homodimers, tetramers of Fc fusion protein homodimers, or higher order aggregates containing five or more Fc fusion protein homodimers). It may be expected that multimeric forms of Fc fusion proteins may have different physical, stability, or pharmacologic activities from that of fusion protein homodimers.

As used herein, a "PD-L1 analog-Fc fusion protein" and a "novel PD-L1 analog-Fc fusion protein" (which terms may be interchangeably used) refer to an immunoglobin Fc domain that is linked to a PD-L1 analog, which is useful in generating antibodies that specifically bind the PD-L1 protein. For case of reference, the term PD-L1, unless otherwise dictated by the context, encompasses protein residues consisting of fragments of the native PD-L1 protein. As used herein, the general terms "fusion protein" and "Fc fusion protein" refer to a protein comprising more than one part, for example from different sources (e.g., different proteins, polypeptides, cells, etc.), that are covalently linked through peptide bonds.

T lymphocytes expressing CD4+ are also known as helper T cells. This subset of T cells can be further subdivided into Th1 cells and Th2 cells. Th1 cells stimulate cellular immune response, participate in the inhibition of macrophage activation, and stimulate B cells to produce IgM, IgG1. Th2 stimulates humoral immune response, promotes B cell proliferation, and induces antibody production (IL-4).

As used herein, the term "activity," "biological activity," "potency," "bioactive potency," or "biological potency" refers to the extent to which an Fc fusion protein binds to or activates a cell receptor and/or exerts the production or reduction of native or foreign substances. As used herein, "in vitro activity" or "receptor activity" refers to the affinity with which an Fc fusion protein binds to a cell receptor and is typically measured by the concentration of an Fc fusion protein that causes the Fc fusion protein to reach half of its maximum binding (i.e., EC50 value).

As used herein, the term "biosynthesis," "recombinant synthesis," or "recombinantly made" refers to the process by which an Fc fusion protein is expressed within a host cell by transfecting the cell with a nucleic acid molecule (e.g., vector) encoding the Fc fusion protein (e.g., where the entire Fc fusion protein is encoded by a single nucleic acid molecule). Exemplary host cells include mammalian cells, e.g., CHO cells or HEK293 cells. The cells can be cultured using standard methods in the art and the expressed Fc fusion protein may be harvested and purified from the cell culture using standard methods in the art.

As used herein, the term "cell surface receptor" refers to a molecule such as a protein, generally found on the external surface of the membrane of a cell and which interacts with soluble molecules, e.g., molecules that circulate in the blood supply. In some embodiments, a cell surface receptor may include a cell receptor (e.g., a PD-1 receptor) or an Fc receptor which binds to an Fc fragment or the Fc region of an antibody (e.g., an Fc (gamma) receptor, for example Fc (gamma) receptor I (or the equivalent canine Fc (gamma) receptor), or an Fc neonatal receptor, for example FcRn). As used herein, "in vitro activity" or "Fc (gamma) receptor activity" or "Fc (gamma) receptor binding" or "FcRn receptor activity" or "FcRn binding" refers to the affinity with which an Fc fusion protein binds to the Fc receptor (e.g., Fc (gamma) receptor or FcRn receptor) and is typically measured by the concentration of an Fc fusion protein that causes the Fc fusion protein to reach half of its maximum binding (i.e., EC50 value) as measured on an assay (e.g., an enzyme-linked immunosorbent assay (ELISA) assay) using OD 450 nm values as measured on a microplate reader.

As used herein, the term "immunogenic" or "immunogenicity" refers to the capacity for a given molecule or antigen (e.g., an Fc fusion protein of the present invention) to provoke the immune system of a target patient such that after administration of the molecule, the patient develops antibodies capable of binding all or specific portions of the molecule (i.e., anti-drug antibodies or ADA). In patients, (e.g., a canine) the antibody development may be polyclonal (e.g., a mixture of antibodies capable of binding an Fc fusion protein). As used herein, the terms "neutralizing," "neutralizing antibodies," or "neutralizing anti-drug antibodies" refer to the capacity for antibodies developed against an Fc fusion protein (e.g., an antigen or antigen analog-Fc fusion protein) to cross-react, bind and interfere with all or a portion of the self-antigen's biological activity in the target patient. For example, in the case of a novel PD-L1 analog-Fc fusion protein molecule (or a pharmaceutical composition thereof) administered to dogs, the immunogenicity refers to antibodies that bind to the PD-L1 portion of the PD-L1 analog-Fc fusion protein but then also cross-react, bind and interfere (e.g., neutralize) with the activity of endogenously produced PD-L1 at a cell surface receptor (e.g., a PD-1 protein, e.g., a PD-1 receptor). Likewise, antibodies generated by the administration of a novel PD-L1 analog-Fc fusion protein molecule (or a pharmaceutical composition thereof) are neutralizing when those anti-PD-L1 antibodies inhibit the binding between an endogenously produced protein (e.g., native PD-L1 protein) in a patient and a patient's host cells that express native PD-1.

As used herein, the term "anti-PD-L1 antibodies" refers to anti-PD-L1 antibodies for any species. As used herein, the terms "anti-canine-PD-L1 antibodies" and "anti-cPD-L1 antibodies" refer to canine-specific anti-PD-L1 antibodies. The term "anti-PD-L1 antibodies" may also be used herein to refer to "anti-canine-PD-L1 antibodies". As used herein, the term "anti-PD-L1 antibody titer" should be understood to refer to anti-canine-PD-L1 antibody titer.

As used herein, the term "immunogenic composition" refers to a pharmaceutical composition or mixture of substances comprising an immunogenic molecule, antigen, or agent, that is suitable for administering to a patient. For example, an immunogenic composition may comprise a PD-L1 analog-Fc fusion protein and a sterile aqueous solution or adjuvant or another carrier.

As used herein, "co-administered with an adjuvant" includes situations where the corresponding fusion protein composition or immunogenic composition further comprises the adjuvant.

As used herein, the term "monomer" refers to a protein or a fusion protein comprising a single polypeptide. In embodiments, the "monomer" is a protein or a fusion protein, e.g., a single polypeptide, comprising a PD-L1 analog polypeptide and an Fc fragment polypeptide, wherein the PD-L1 fragment and Fc fragment polypeptides are joined by peptide bonds via a linker to form the single polypeptide. In embodiments, the monomer is encoded by a single nucleic acid molecule.

As used herein and as illustrated in FIG. 1, "N-terminus" refers to the start of a protein or polypeptide that is initiated by an amino acid containing a free amine group that is the alpha-amino group of the amino acid (e.g., the free amino that is covalently linked to one carbon atom that is located adjacent to a second carbon atom, wherein the second carbon atom is part of the carbonyl group of the amino acid). As used herein and as illustrated in FIG. 1, "C-terminus" refers to the end of a protein or polypeptide that is terminated by an amino acid containing a carboxylic acid group, wherein the carbon atom of the carboxylic acid group is located adjacent to the alpha-amino group of the amino acid.

As used herein, the term "carrier" is used herein to refer to diluents, excipients, vehicles, and the like, in which the Fc fusion protein(s) may be dispersed, emulsified, or encapsulated for administration. Suitable carriers will be pharmaceutically acceptable. As used herein, the term "pharmaceutically acceptable" means not biologically or otherwise undesirable, in that it can be administered to a patient without excessive toxicity, irritation, or allergic response, and does not cause unacceptable biological effects or interact in a deleterious manner with any of the other components of the composition in which it is contained. A pharmaceutically acceptable carrier would naturally be selected to minimize any degradation of the compound or other agents and to minimize any adverse side effects in the patient, as would be well known to one of skill in the art. Pharmaceutically acceptable ingredients include those acceptable for veterinary use as well as human pharmaceutical use and will depend on the route of administration. Any carrier compatible with the excipient(s) and the Fc fusion protein(s) can be used. In example, an adjuvant may be considered one type or subclass of carrier.

As used herein, "pharmacodynamics" or "PD" generally refers to the biological effects of an Fc fusion protein in a patient. As an example, herein, the PD of a novel PD-L1 analog-Fc fusion protein refers to the measure of the anti-PD-L1 antibody titers over time in a patient after the administration of the novel PD-L1 analog-Fc fusion protein.

As used herein, "pharmacokinetics" or "PK" generally refers to the characteristic interactions of an Fc fusion protein and the body of the patient in terms of its absorption, distribution, metabolism, and excretion. As an example, herein, the PK refers to the concentration of a novel PD-L1 analog-Fc fusion protein in the blood or serum of a patient at a given time after the administration of the novel PD-L1 analog-Fc fusion protein. As used herein, "half-life" refers to the time taken for the concentration of Fc fusion protein in the blood or serum of a patient to reach half of its original value as calculated from a first order exponential decay model for drug elimination. Fc fusion proteins with greater "half-life" values demonstrate greater duration of action in the target patient.

The terms "sequence identity," "sequence homology," "homology," or "identical" in amino acid or nucleotide sequences as used herein describes that the same nucleotides or amino acid residues are found within the variant and reference sequences when a specified, contiguous segment of the nucleotide sequence or amino acid sequence of the variant is aligned and compared to the nucleotide sequence or amino acid sequence of the reference sequence. Methods for sequence alignment and for determining identity between sequences are known in the art, including the use of Clustal Omega, which organizes, aligns, and compares sequences for similarity, wherein the software highlights each sequence position and compares across all sequences at that position and assigns one of the following scores: an "*" (asterisk) for sequence positions which have a single, fully conserved residue, a ":" (colon) indicates conservation between groups of strongly similar properties with scoring greater than 0.5 in the Gonnet PAM 250 matrix, and a "." (period) indicates conservation between groups of weakly similar properties with scoring less than or equal to 0.5 in the Gonnet PAM 250 matrix, a "-" (dash) indicates a sequence gap, meaning that no local homology exists within a particular set of comparisons within a certain range of the sequences, and an empty space " " indicates little or no sequence homology for that particular position across the compared sequences.

With respect to optimal alignment of two nucleotide sequences, the contiguous segment of the variant nucleotide sequence may have additional nucleotides or deleted nucleotides with respect to the reference nucleotide sequence. Likewise, for purposes of optimal alignment of two amino acid sequences, the contiguous segment of the variant amino acid sequence may have additional amino acid residues or deleted amino acid residues with respect to the reference amino acid sequence. In some embodiments, the contiguous segment used for comparison to the reference nucleotide sequence or reference amino acid sequence will comprise at least 6, 10, 15, or 20 contiguous nucleotides, or amino acid residues, and may be 30, 40, 50, 100, or more nucleotides or amino acid residues. Corrections for increased sequence identity associated with inclusion of gaps in the variant's nucleotide sequence or amino acid sequence can be made by assigning gap penalties. Methods of sequence alignment are known in the art.

In embodiments, the determination of percent identity or "homology" between two sequences is accomplished using a mathematical algorithm. For example, the percent identity of an amino acid sequence is determined using the Smith-Waterman homology search algorithm using an affine 6 gap search with a gap open penalty of 12 and a gap extension penalty of 2, BLOSUM matrix 62. In embodiments, the percent identity of a nucleotide sequence is determined using the Smith-Waterman homology search algorithm using a gap open penalty of 25 and a gap extension penalty of 5. Such a determination of sequence identity can be performed using, for example, the DeCypher Hardware Accelerator from TimeLogic.

As used herein, the term "homology" is used to compare two or more proteins by locating common structural characteristics and common spatial distribution of, for instance, beta strands, helices, and folds. Accordingly, homologous protein structures are defined by spatial analyses. Measuring structural homology involves computing the geometric-topological features of a space. One approach used to generate and analyze three-dimensional (3D) protein structures is homology modeling (also called comparative modeling or knowledge-based modeling) which works by finding similar sequences on the basis of the fact that 3D similarity reflects 2D similarity. Homologous structures do not imply sequence similarity as a necessary condition.

As used herein, the terms "subject" or "target subject" or "patient" or "patient subject" or "pets" or "companion animals" are intended to include mammals, including mice and canines. Exemplary canine subjects or patients include dogs having a disease or a disorder, e.g., cancer or other diseases associated with expression of the PD-L1 protein described herein, or normal subjects.

As used herein, the term "titer", "manufacturing titer" or "yield" refers to the amount of a fusion protein product (e.g., an Fc fusion protein described herein) resulting from the biosynthesis (e.g., in a mammalian cell, e.g., in a HEK293 cell or CHO cell) per volume of the cell culture. The amount of product may be determined at any step of the production process (e.g., before or after purification), but the yield or titer is always stated per volume of the original cell culture. As used herein, the term "product yield" or "total protein yield" refers to the total amount of Fc fusion protein expressed by cells and purified via at least one affinity chromatography step (e.g., Protein A or Protein G) and includes monomers of Fc fusion protein, homodimers of Fc fusion protein, and higher-order molecular aggregates of homodimers of Fc fusion protein. As used herein, the term "percent homodimer" or "% homodimer" refers to the proportion of a fusion protein product (e.g., an Fc fusion protein described herein) that is the desired homodimer. As used herein, the term "homodimer titer" refers to the product of the % homodimer and the total protein yield after Protein A purification step reported per volume of the cell culture.

As used herein, the terms "treat" or "treating" or "treatment" of a patient having a disease or a disorder refers to an intervention performed with the intention of mitigating or preventing the symptoms (in particular, a treatment for cancer) associated with the condition or disease, and/or reducing the duration of the symptoms associated with the condition or disease. Accordingly, "treatment" refers to both therapeutic treatment and prophylactic or preventative measures. Improvement after treatment may be manifested as a decrease or elimination of such symptoms, e.g., by a decrease in tumor size or elimination of the tumor, and/or by a decrease in the duration of such symptoms. As an example, the compositions described herein are useful in treating cancers or other diseases associated with the expression of the PD-L1 protein. Treating a patient having a condition or disease may refer to subjecting the patient with the condition or disease to a treatment regimen, for example the administration of a fusion protein such as a PD-L1 analog-Fc fusion protein described herein, or a pharmaceutical composition of a fusion protein such as a PD-L1 analog-Fc fusion protein described herein, such that the cancer or other diseases associated with the expression of the PD-L1 protein are reduced, alleviated, relieved, altered, remedied, ameliorated, or improved. Treating includes administering an amount of a fusion protein such as a PD-L1 analog-Fc fusion protein described herein, or a pharmaceutical composition of a fusion protein such as a PD-L1 analog-Fc fusion protein described herein that is effective to reduce, alleviate, relieve, alter, remedy, ameliorate, improve, the health of a patient with a cancer or other diseases associated with to the expression of the PD-L1 protein associated with the condition or disease. Treating includes administering an amount effective to generate antibodies to an antigen (in this case PD-L1) in a patient that has a condition or disease with the intention of generating antibodies targeted to PD-L1 (the antigen) that will inhibit the interaction of endogenous PD-L1 and endogenous PD-1 in a patient, thereby triggering an immune response to attack the cancer or other diseases and improving the health of a patient.

As used herein, a "therapeutic vaccine" refers to a treatment that introduces an antigen or antigen analog into a patient that has a condition or disorder associated with a self-antigen, with the goal that the patient's immune system will create antibodies for the antigen or antigen analog, enabling the patient's body to reduce the level of the self-antigen and have an ameliorating effect on symptoms of the condition or disorder that are associated with the self-antigen (for example, allowing the body to identify a cancer cell and triggering an immune response).

As used herein, a "prophylactic vaccine" or "prophylactic immunization" or "preventative vaccine" refers to the artificial establishment of specific immunity through the introduction of antigens into a patient that is not necessarily suffering with the symptoms of a condition or disorder, with the goal that the patient's immune system will create antibodies against the antigen and thereby prevent any future suffering or increase in suffering with the symptoms of the disorder. The distinction between a prophylactic vaccine and a therapeutic vaccine, is that a therapeutic vaccine is typically administered to a patient that is already suffering from the symptoms that the immunity targets, and a prophylactic vaccine is typically administered to a patient in anticipation of the patient suffering from the symptoms that the immunity targets.

As used herein, "booster vaccine" refers to an extra administration of a vaccine after the patient has previously received an initial administration of a vaccine, or after a patient has acquired antibodies (i.e., has a measurable antibody titer) through having had a previous treatment which introduced antibodies to reduce the symptoms of the condition or disease, or having had previous exposure to the antigen. In some examples, an additional dose of a vaccine is beneficial to periodically to "boost" the immunity of a patient to an antigen, by increasing the patient's antigen antibody titer, which in turn ameliorates the symptoms caused by the antigen.

As used herein, the phrase "effective amount" or "therapeutically effective amount" is meant to refer to a therapeutic or prophylactic amount of the PD-L1 analog-Fc fusion protein of the present disclosure or pharmaceutical composition thereof, that elicit the desired therapeutic or prophylactic effect or response in stimulating the immune system of the patient to generate antibodies, as evidenced by the alleviation of some or all of such symptoms of the condition or disease, when administered in accordance with the desired treatment regimen. In examples, where the desired therapeutic or prophylactic effect or response is to alleviate symptoms of a condition or disease, an amount of a PD-L1 analog-Fc fusion protein of the present disclosure or pharmaceutical composition thereof may be considered therapeutically effective if symptoms and/or effects of the condition or disease are observably reduced in the patient after the treatment regime. The therapeutically effective dosage of a PD-L1 analog-Fc fusion protein may vary depending on the size and species of the patient, and/or according to the mode of administration.

As used herein, when referring to an amino acid in some portion of an amino acid sequence, for example a PD-L1 analog amino acid sequence, a cited amino acid position is referenced as the position of the amino acid counting from the beginning of the amino acid sequence itself. For example, consider the canine PD-L1 amino acid sequence of SEQ ID NO: 3.

(SEQ ID NO: 3)
MRMFSVFTFMAYCHLLKAFTITVSKDLYVVEYGGNVTMECKFPVEKQLNL

FALIVYWEMEDKKIIQFVNGKEDLKVQHSSYSQRAQLLKDQLFLGKAALQ

ITDVRLQDAGVYCCLIGYGGADYKRITLKVHAPYRNISQRISVDPVTSEH

ELMCQAEGYPEAEVIWTSSDHRVLSGKTTITNSNREEKLFNVTSTLNINA

TANEIFYCTFQRSGPEENNTAELVIPERLPVPASERTHFMILGPFLLLLG

VVLAVTFCLKKHGRMMDVEKCCTRDRNSKKRNDIQFEET.

A mutation of the first serine amino acid (denoted by "S") of this sequence would be described as a mutation of the 5$^{th}$ amino acid of the sequence. For example, if the first serine amino acid in SEQ ID NO: 3 were mutated to asparagine, this could be referred to as an S5N mutation of SEQ ID NO: 3.

As used herein, a "PD-L1 fragment" refers to a portion of a novel PD-L1 analog-Fc fusion protein that comprises some portion of the PD-L1 protein given in SEQ ID NO: 2 or SEQ ID NO: 3. In examples, the PD-L1 fragment is linked to an Fc fragment or analog thereof, as illustrated in FIG. 1.

As used herein, a "treatment for cancers or other diseases associated with the expression of PD-L1 protein" refers to any cancer (original, part of a tumor, circulating (e.g., lymphomas) or metastasized) or disease involving cells that express a PD-L1 protein. Non-limiting examples of cancers or diseases associated with the expression of PD-L1 can include cancers of the lung, liver, ovary, cervix, skin, colon, glioma, bladder, breast, kidney, esophagus, stomach, oral squamous cell, urothelial cell, and pancreas, as well as tumors of the head and neck, melanoma, non-small cell lung cancer (NSCLC) and renal carcinoma.

Novel PD-L1 Analog-Fc Fusion Proteins

Cancer is a prevalent disease in dogs frequently resulting in mortality or in euthanasia of the patient. The present disclosure evaluates the beneficial effects of systemic active immunization against the programed death ligand (PD-L1); for example, to mitigate cancer thus delaying mortality and reducing euthanasia in domesticated dogs. Active immunization against PD-L1 may be used to complement conventional treatments currently offered to relieve cancers or other diseases associated with the expression of the PD-L1 protein, thus improving dogs' quality of life and sparing suffering dogs from euthanasia. The goal therefore is to create an Fc fusion protein comprising a PD-L1 analog and a Fc fragment (e.g., human or canine) in order to create a manufacturable conjugate that presents the antigen (PD-L1) in a novel manner to cause a patient (e.g., a canine) to produce anti-PD-L1-antibodies capable of cross-reacting and neutralizing endogenously-produced PD-L1. In neutralizing the endogenously produced PD-L1, the antibodies produced in response to the administered therapeutic vaccine are able to treat cancers or other diseases associated with the expression of the PD-L1 protein.

PD-L1 is a protein that consists of four sections: a signal peptide, an extracellular region, a transmembrane-domain, and an intracellular area. The human PD-L1 protein sequence is shown below as SEQ ID NO: 2.

(SEQ ID NO: 2)

MRIFAVFIFMTYWHLLNAFTVTVPKDLYVVEYGSNMTIECKFPVEKQLDL

AALIVYWEMEDKNIIQFVHGEEDLKVQHSSYRQRARLLKDQLSLGNAALQ

ITDVKLQDAGVYRCMISYGGADYKRITVKVNAPYNKINQRILVVDPVTSE

HELTCQAEGYPKAEVIWTSSDHQVLSGKTTTTNSKREEKLFNVTSTLRIN

TTTNEIFYCTFRRLDPEENHTAELVIPELPLAHPPNERTHLVILGAILLC

LGVALTFIFRLRKGRMMDVKKCGIQDTNSKKQSDTHLEET.

The PD-L1 protein sequence for dogs is structurally similar but has significant differences in the protein. The canine PD-L1 protein sequence is shown below as SEQ ID NO: 3.

(SEQ ID NO: 3)

MRMFSVFTFMAYCHLLKAFTITVSKDLYVVEYGGNVTMECKFPVEKQLNL

FALIVYWEMEDKKIIQFVNGKEDLKVQHSSYSQRAQLLKDQLFLGKAALQ

ITDVRLQDAGVYCCLIGYGGADYKRITLKVHAPYRNISQRISVDPVTSEH

ELMCQAEGYPEAEVIWTSSDHRVLSGKTTITNSNREEKLFNVTSTLNINA

TANEIFYCTFQRSGPEENNTAELVIPERLPVPASERTHFMILGPFLLLLG

VVLAVTFCLKKHGRMMDVEKCCTRDRNSKKRNDIQFEET.

A Clustal Omega comparison of the human and canine PD-L1 protein sequences or SEQ ID NO: 2 and SEQ ID NO: 3 respectively, which highlights the differences in the protein sequences, is shown in FIG. 2.

The PD-L1 found on the surface of some cells, and which is expressed in cancer cells interacts with the PD-1 receptor on the surface of immune T cells. The sequence for the human PD-1 sequence is shown below as SEQ ID NO: 4.

(SEQ ID NO: 4)

MQIPQAPWPVVWAVLQLGWRPGWFLDSPDRPWNPPTFSPALLVVTEGDNA

TFTCSFSNTSESFVLNWYRMSPSNQTDKLAAFPEDRSQPGQDCRFRVTQL

PNGRDFHMSVVRARRNDSGTYLCGAISLAPKAQIKESLRAELRVTERRAE

VPTAHPSPSPRPAGQFQTLVVGVVGGLLGSLVLLVWVLAVICSRAARGTI

GARRTGQPLKEDPSAVPVFSVDYGELDFQWREKTPEPPVPCVPEQTEYAT

IVFPSGMGTSSPARRGSADGPRSAQPLRPEDGHCSWPL.

The PD-1 for dogs is structurally similar to the PD-1 for humans but has significant differences in the protein sequence. The complete canine PD-1 is shown below as SEQ ID NO: 5.

(SEQ ID NO: 5)

MGSRRGPWPLVWAVLQLGWWPGWLLDSPDRPWSPLTFSPAQLTVQEGENA

TFTCSLADIPDSFVLNWYRLSPRNQTDKLAAFQEDRIEPGRDRRFRVTRL

PNGRDFHMSIVAARLNDSGIYLCGAIYLPPNTQINESPRAELSVTERTLE

PPTQSPSPPPRLSGQLQGLVIGVTSVLVGVLLLLLLTWVLAAVFPRATRG

ACVCGSEDEPLKEGPDAAPVFTLDYGELDFQWREKTPEPPAPCAPEQTEY

ATIVFPGRPASPGRRASASSLQGAQPPSPEDGPGLWPL

A Clustal Omega comparison of the human PD-1 sequence, and the canine PD-1 sequence (SEQ ID NO: 4 and SEQ ID NO: 5 respectively) which highlights the differences in the protein is shown in FIG. 3.

In choosing the PD-L1 analog for the novel PD-L1 analog-Fc fusion protein it is conceivable that one could choose a PD-L1 analog that includes some portion of a wild-type PD-L1 protein. For example, the PD-L1 analog for a novel PD-L1 analog-Fc fusion protein may comprise all or a portion of the human PD-L1 protein of SEQ ID NO: 2, or may comprise all or a portion of the canine PD-L1 protein of SEQ ID NO: 3. In examples, the PD-L1 analog may comprise additional amino acids or polypeptides, (collectively then referred to as the PD-L1 analog). In examples, one or more amino acids in the PD-L1 analog of the novel PD-L1 analog-Fc fusion protein may be deleted or mutated from their native state.

It is expected that different PD-L1 analog-Fc fusion protein designs will result in different protein yields (see for example, Beygmoradi et al., (2023). *Recombinant protein expression: Challenges in production and folding related matters, International Journal of Biological Macromolecules,* Volume 233, 123407, ISSN 0141-8130, *doi.org/*10.1016/*j.ijbiomac.*2023.123407, and Massimo Stefani, (2004). *Protein misfolding and aggregation: new examples in medicine and biology of the dark side of the protein world, Biochimica et Biophysica Acta (BBA)-Molecular Basis of Disease,* Volume 1739, Issue 1, Pages 5-25, ISSN 0925-4439).

For example, larger or shorter PD-L1 analog sequences in the PD-L1 analog, when used to produce the PD-L1 analog-Fc fusion protein, are expected to result in different protein yields. The resulting protein yield when the selected PD-L1 analog is attached to an Fc fragment can be experimentally determined. The choice of the Fc fragment and the portion of the Fc fragment hinge region that is linked to the selected PD-L1 analog impacts the manufacturability of the PD-L1 analog-Fc fusion protein.

The novel PD-L1 analog-Fc fusion protein may comprise a peptide linker. In examples, the protein comprising the PD-L1 analog is linked to the N-terminal side of the Fc fragment. In examples, the novel PD-L1 analog-Fc fusion protein comprises domains in the following orientation from N- to C-termini: (N-terminus)—antigen—peptide linker—Fc fragment—(C-terminus) (e.g., (N-terminus)—PD-L1 analog—peptide linker—Fc fragment—(C-terminus)). In examples, the length and composition of the linker connecting the PD-L1 analog to the Fc fragment may impact the protein yield.

A first design goal is to create a PD-L1 analog-Fc fusion protein with a protein yield after production in transiently transfected CHO cells and protein A purification that may be greater than 50 mg/L (e.g., greater than 60 mg/L, greater than 70 mg/L, greater than 80 mg/L, greater than 90 mg/L, preferably greater than 100 mg/L). A second design goal is to create a PD-L1 analog-Fc fusion protein capable of inducing a significant immune response in mice. A third design goal is to create a PD-L1 analog-Fc fusion protein capable of inducing a significant immune response in dogs. The goal is to create a PD-L1 analog-Fc fusion protein which combines the qualities of both an acceptable manufacturing yield and the capability to induce immunogenicity.

As a first attempt in creating a novel PD-L1 analog-Fc fusion protein for use in canines, the human native PD-L1 protein of SEQ ID NO: 2 was truncated to form a PD-L1 analog. It was expected that using a portion of the human PD-L1 protein would cause the PD-L1 analog-Fc fusion protein to potentially be more immunogenic in animals (e.g., mice or dogs) than using a portion of a canine native PD-L1 protein sequence. The human native PD-L1 protein fragment comprised a truncated section of the extracellular region of the human PD-L1 protein and included part of the transmembrane domain (TM-domain). The resulting PD-L1 analog of SEQ ID NO: 8 is shown below:

```
                                          (SEQ ID NO: 8)
TIECKFPVEKQLDLAALIVYWEMEDKNIIQFVHGEEDLKVQHSSYRQRAR

LLKDQLSLGNAALQITDVKLQDAGVYRCMISYGGADYKRITVKVNAPYNK

INQRILVVDPVTSEHELTCQAEGYPKAEVIWTSSDHQVLSGKTTTTNSKR

EEKLFNVTSTLRINTTTNEIFYCTFRRLDPEENHTAELVIPELPLAHPPN

ERTHLVILGAI
```

The PD-L1 analog of SEQ ID NO: 8 was linked to the IgGB canine Fc of SEQ ID NO: 1. Canine IgGB was chosen as it is known to have greater immunogenicity than the other IgG in canines (IgGA, IgGC and IgGD). In the canine IgGB fragment of SEQ ID NO: 1, the C-terminus lysine on the native canine IgGB fragment was eliminated. The C-terminal lysine that is found in native IgG isotype Fc fragment amino acid sequences (i.e., the lysine that represents the last amino acid of the Fc fragment sequence) is known to result in the accidental production of unwanted amino acid sequence variants during manufacturing (e.g., Fc fragments containing the C-terminal lysine becoming mixed with Fc fragments where the C-terminal lysine is omitted) which can occur during production of the desired protein within cells (Dick, L W., (2008) *Biotechnol Bioeng.* August 15;100(6) pp1,132-43). Therefore, it was expected that removing the C-terminal lysine would improve manufacturing yield and purity. The canine IgGB Fc fragment sequence lacking a C-terminal lysine is given in SEQ ID NO: 1:

```
                                          (SEQ ID NO: 1)
DCPKCPAPEMLGGPSVFIFPPKPKDTLLIARTPEVTCVVVDLDPEDPEVQ

ISWFVDGKQMQTAKTQPREEQFNGTYRVVSVLPIGHQDWLKGKQFTCKVN

NKALPSPIERTISKARGQAHQPSVYVLPPSREELSKNTVSLTCLIKDFFP

PDIDVEWQSNGQQEPESKYRTTPPQLDEDGSYFLYSKLSVDKSRWQRGDT

FICAVMHEALHNHYTQESLSHSPG
```

The human PD-L1 analog of SEQ ID NO: 8 was linked using the peptide linker GGGGQGGGSGGQGGGGG (SEQ ID NO: 6) to the canine IgGB Fc fragment.

The resultant PD-L1 analog-Fc fusion protein is given below as SEQ ID NO: 15.

```
                                          (SEQ ID NO: 15)
TIECKFPVEKQLDLAALIVYWEMEDKNIIQFVHGEEDLKVQHSSYRQRA

RLLKDQLSLGNAALQITDVKLQDAGVYRCMISYGGADYKRITVKVNAPY

NKINQRILVVDPVTSEHELTCQAEGYPKAEVIWTSSDHQVLSGKTTTTN

SKREEKLFNVTSTLRINTTTNEIFYCTFRRLDPEENHTAELVIPELPLA

HPPNERTHLVILGAIGGGGQGGGSGGQGGGGGDCPKCPAPEMLGGPSVF

IFPPKPKDTLLIARTPEVTCVVVDLDPEDPEVQISWFVDGKQMQTAKTQ

PREEQFNGTYRVVSVLPIGHQDWLKGKQFTCKVNNKALPSPIERTISKA
```

```
                           -continued
RGQAHQPSVYVLPPSREELSKNTVSLTCLIKDFFPPDIDVEWQSNGQQE

PESKYRTTPPQLDEDGSYFLYSKLSVDKSRWQRGDTFICAVMHEALHNH

YTQESLSHSPG
```

The PD-L1 analog-Fc fusion protein of SEQ ID NO: 15 was manufactured in CHO cells according to Example 1 and was purified according to Example 3. The Fc fusion protein structure of the PD-L1 analog-Fc fusion protein of SEQ ID NO: 15 was confirmed according to Example 4, and sequence identification is performed according to Example 6. The resultant yield of the fusion protein produced was 3 mg/L, which is below both the design goal of 50 mg/L and the preferred design goal of 100 mg/L.

In a second attempt to produce a PD-L1 analog-Fc fusion protein with acceptable manufacturing yield, the native human PD-L1 protein of SEQ ID NO: 2 was truncated further to shorten the length of the extracellular region of the PD-L1 protein but still include part of the TM-domain. The resulting PD-L1 analog of SEQ ID NO: 9 is shown below:

```
                                          (SEQ ID NO: 9)
MISYGGADYKRITVKVNAPYNKINQRILVVDPVTSEHELTCQAEGYPKA

EVIWTSSDHQVLSGKTTTTNSKREEKLFNVTSTLRINTTTNEIFYCTFR

RLDPEENHTAELVIPELPLAHPPNERTHLVILGAI
```

The human PD-L1 analog of SEQ ID NO: 9 was linked using the peptide linker GGGGQGGGSGGQGGGGG (SEQ ID NO: 6) to the canine IgGB Fc fragment of SEQ ID NO: 1. The resultant PD-L1 analog-Fc fusion protein is given below as SEQ ID NO: 16.

```
                                          (SEQ ID NO: 16)
MISYGGADYKRITVKVNAPYNKINQRILVVDPVTSEHELTCQAEGYPKA

EVIWTSSDHQVLSGKTTTTNSKREEKLFNVTSTLRINTTTNEIFYCTFR

RLDPEENHTAELVIPELPLAHPPNERTHLVILGAIGGGGQGGGSGGQGG

GGGDCPKCPAPEMLGGPSVFIFPPKPKDTLLIARTPEVTCVVVDLDPED

PEVQISWFVDGKQMQTAKTQPREEQFNGTYRVVSVLPIGHQDWLKGKQF

TCKVNNKALPSPIERTISKARGQAHQPSVYVLPPSREELSKNTVSLTCL

IKDFFPPDIDVEWQSNGQQEPESKYRTTPPQLDEDGSYFLYSKLSVDKS

RWQRGDTFICAVMHEALHNHYTQESLSHSPG
```

The PD-L1 analog-Fc fusion protein of SEQ ID NO: 16 was manufactured in CHO cells according to Example 1 and was purified according to Example 3. The Fc fusion protein structure of the PD-L1 analog-Fc fusion protein of SEQ ID NO: 16 was confirmed according to Example 4, and sequence identification is performed according to Example 6. The resultant yield of the fusion protein produced was 18 mg/L, which is below both the design goal of 50 mg/L and the preferred design goal of 100 mg/L.

In a third attempt to produce a PD-L1 analog-Fc fusion protein with acceptable manufacturing yield, a different portion of the human PD-L1 protein of SEQ ID NO: 2 was selected as the PD-L1 analog. This portion was taken from the extracellular region of the human PD-L1 protein and did not include any part of the TM-domain of the human PD-L1 protein. The resulting PD-L1 analog of SEQ ID NO: 10 is shown below:

(SEQ ID NO: 10)

FTVTVPKDLYVVEYGSNMTIECKFPVEKQLDLAALIVYWEMEDKNIIQF

VHGEEDLKVQHSSYRQRARLLKDQLSLGNAALQITDVKLQDAGVYRCMI

SYGGADYKRITVKVNAPYNKINQRILVVDPVTS

The human PD-L1 analog of SEQ ID NO: 10 was linked using the peptide linker GGGGQGGGSGGQGGGGG (SEQ ID NO: 6) to the canine IgGB Fc fragment of SEQ ID NO: 1. The resultant PD-L1 analog-Fc fusion protein is given below as SEQ ID NO: 17.

(SEQ ID NO: 17)

FTVTVPKDLYVVEYGSNMTIECKFPVEKQLDLAALIVYWEMEDKNIIQF

VHGEEDLKVQHSSYRQRARLLKDQLSLGNAALQITDVKLQDAGVYRCMI

SYGGADYKRITVKVNAPYNKINQRILVVDPVTSGGGGQGGGSGGQGGGG

GDCPKCPAPEMLGGPSVFIFPPKPKDTLLIARTPEVTCVVVDLDPEDPE

VQISWFVDGKQMQTAKTQPREEQFNGTYRVVSVLPIGHQDWLKGKQFTC

KVNNKALPSPIERTISKARGQAHQPSVYVLPPSREELSKNTVSLTCLIK

DFFPPDIDVEWQSNGQQEPESKYRTTPPQLDEDGSYFLYSKLSVDKSRW

QRGDTFICAVMHEALHNHYTQESLSHSPG

The PD-L1 analog-Fc fusion protein of SEQ ID NO: 17 was manufactured in CHO cells according to Example 1 and was purified according to Example 3. The Fc fusion protein structure of the PD-L1 analog-Fc fusion protein of SEQ ID NO: 17 was confirmed according to Example 4, and sequence identification is performed according to Example 6. The resultant yield of the fusion protein produced was 35 mg/L, which is below both the design goal of 50 mg/L and the preferred design goal of 100 mg/L.

In a fourth attempt to produce a PD-L1 analog-Fc fusion protein with acceptable manufacturing yield, the portion of the human PD-L1 protein sequence of SEQ ID NO: 2 selected as the PD-L1 analog was truncated further. The resulting PD-L1 analog of SEQ ID NO: 11 is shown below:

(SEQ ID NO: 11)

MISYGGADYKRITVKVNAPYNKINQRILVVDPVTS

A comparison of the PD-L1 analogs of SEQ ID NO: 8, SEQ ID NO: 9, SEQ ID NO: 10 and SEQ ID NO: 11 is shown in FIG. 4.

The human PD-L1 analog of SEQ ID NO: 11 was linked using the peptide linker GGGGQGGGSGGQGGGGG (SEQ ID NO: 6) to the canine IgGB Fc fragment of SEQ ID NO: 1. The resultant PD-L1 analog-Fc fusion protein is given below as SEQ ID NO: 18.

(SEQ ID NO: 18)

MISYGGADYKRITVKVNAPYNKINQRILVVDPVTSGGGGQGGGSGGQGG

GGGDCPKCPAPEMLGGPSVFIFPPKPKDTLLIARTPEVTCVVVDLDPED

PEVQISWFVDGKQMQTAKTQPREEQFNGTYRVVSVLPIGHQDWLKGKQF

TCKVNNKALPSPIERTISKARGQAHQPSVYVLPPSREELSKNTVSLTCL

IKDFFPPDIDVEWQSNGQQEPESKYRTTPPQLDEDGSYFLYSKLSVDKS

RWQRGDTFICAVMHEALHNHYTQESLSHSPG.

The PD-L1 analog-Fc fusion protein of SEQ ID NO: 18 was manufactured in CHO cells according to Example 1 and was purified according to Example 3. The Fc fusion protein structure of the PD-L1 analog-Fc fusion protein of SEQ ID NO: 18 was confirmed according to Example 4, and sequence identification is performed according to Example 6. The resultant yield of the fusion protein produced was 10 mg/L, which is below both the design goal of 50 mg/L and the preferred design goal of 100 mg/L.

A comparison of the PD-L1 analog-Fc fusion proteins of SEQ ID NO: 15, SEQ ID NO: 16, SEQ ID NO: 17 and SEQ ID NO: 18 is shown in FIG. 5A, FIG. 5B, and FIG. 5C.

The use of non-native (i.e., non-canine) PD-L1 in an attempt to create maximum immunogenicity against a human PD-L1 sequence that could cross react against native canine PD-L1 in a canine patient did not allow for meeting the manufacturing titer design goal. Therefore, in a fifth attempt to create a PD-L1 analog-Fc fusion protein with titers that meet the design goal, the human PD-L1 analog was replaced by an analog of the canine native PD-L1 protein (SEQ ID NO: 3). A truncated section of the extra-cellular region of the canine PD-L1 protein including part of the TM-domain was selected as the fragment for the canine PD-L1 analog. In addition, the canine PD-L1 analog was mutated at position 77 with a cysteine (C) to arginine (R) substitution (C77R) to eliminate the cysteine-cysteine (CC) motif at position 77 and 78, so as to remove a potential unpaired cysteine moiety. The resulting canine PD-L1 analog is SEQ ID NO: 12, with the C77R mutation shown in bold below:

(SEQ ID NO: 12)

TMECKFPVEKQLNLFALIVYWEMEDKKIIQFVNGKEDLKVQHSSYSQRA

QLLKDQLFLGKAALQITDVRLQDAGVYRCLIGYGGADYKRITLKVHAPY

RNISQRISVDPVTSEHELMCQAEGYPEAEVIWTSSDHRVLSGKTTITNS

NREEKLFNVTSTLNINATANEIFYCTFQRSGPEENNTAELVIPERLPVP

ASERTHFMILGPF

The canine PD-L1 analog of SEQ ID NO: 12 was linked using the peptide linker GGGGQGGGSGGQGGGGG (SEQ ID NO: 6) to the canine IgGB Fc fragment of SEQ ID NO: 1. The resultant PD-L1 analog-Fc fusion protein is given below as SEQ ID NO: 19.

(SEQ ID NO: 19)

TMECKFPVEKQLNLFALIVYWEMEDKKIIQFVNGKEDLKVQHSSYSQRA

QLLKDQLFLGKAALQITDVRLQDAGVYRCLIGYGGADYKRITLKVHAPY

RNISQRISVDPVTSEHELMCQAEGYPEAEVIWTSSDHRVLSGKTTITNS

NREEKLFNVTSTLNINATANEIFYCTFQRSGPEENNTAELVIPERLPVP

ASERTHFMILGPFGGGGQGGGSGGQGGGGGDCPKCPAPEMLGGPSVFIF

PPKPKDTLLIARTPEVTCVVVDLDPEDPEVQISWFVDGKQMQTAKTQPR

EEQFNGTYRVVSVLPIGHQDWLKGKQFTCKVNNKALPSPIERTISKARG

QAHQPSVYVLPPSREELSKNTVSLTCLIKDFFPPDIDVEWQSNGQQEPE

SKYRTTPPQLDEDGSYFLYSKLSVDKSRWQRGDTFICAVMHEALHNHYT

QESLSHSPG.

The PD-L1 analog-Fc fusion protein of SEQ ID NO: 19 was manufactured in CHO cells according to Example 1 and was purified according to Example 3. The Fc fusion protein structure of the PD-L1 analog-Fc fusion protein of SEQ ID NO: 19 was confirmed according to Example 4, and sequence identification is performed according to Example 6. The resultant yield of the fusion protein produced was 15 mg/L, which is below both the design goal of 50 mg/L and the preferred design goal of 100 mg/L.

In a sixth attempt to create a PD-L1 analog-Fc fusion protein, a different fragment of the extracellular region of the canine PD-L1 protein of SEQ ID NO: 3 was used as the canine PD-L1 analog. The fragment did not include any part of the TM-domain. In addition, the canine PD-L1 analog was mutated at position 95 with a cysteine (C) to arginine (R) substitution (C95R) to eliminate the cysteine-cysteine (CC) motif at positions 95 and 96, so as to remove a potential unpaired cysteine moiety. The resulting canine PD-L1 analog is SEQ ID NO: 13, with the C95R mutation shown in bold below:

```
                                        (SEQ ID NO: 13)
FTITVSKDLYVVEYGGNVTMECKFPVEKQLNLFALIVYWEMEDKKIIQF

VNGKEDLKVQHSSYSQRAQLLKDQLFLGKAALQITDVRLQDAGVYRCLI

GYGGADYKRITLKVHAPYRNISQRISVDPVTS
```

The canine PD-L1 analog of SEQ ID NO: 13 was linked using the peptide linker GGGGQGGGSGGQGGGGG (SEQ ID NO: 6) to the canine IgGB Fc fragment of SEQ ID NO: 1. The resultant PD-L1 analog-Fc fusion protein is given below as SEQ ID NO: 20.

```
                                        (SEQ ID NO: 20)
FTITVSKDLYVVEYGGNVTMECKFPVEKQLNLFALIVYWEMEDKKIIQF

VNGKEDLKVQHSSYSQRAQLLKDQLFLGKAALQITDVRLQDAGVYRCLI

GYGGADYKRITLKVHAPYRNISQRISVDPVTSGGGGQGGGSGGQGGGGG

DCPKCPAPEMLGGPSVFIFPPKPKDTLLIARTPEVTCVVVDLDPEDPEV

QISWFVDGKQMQTAKTQPREEQFNGTYRVVSVLPIGHQDWLKGKQFTCK

VNNKALPSPIERTISKARGQAHQPSVYVLPPSREELSKNTVSLTCLIKD

FFPPDIDVEWQSNGQQEPESKYRTTPPQLDEDGSYFLYSKLSVDKSRWQ

RGDTFICAVMHEALHNHYTQESLSHSPG.
```

Figure 15:
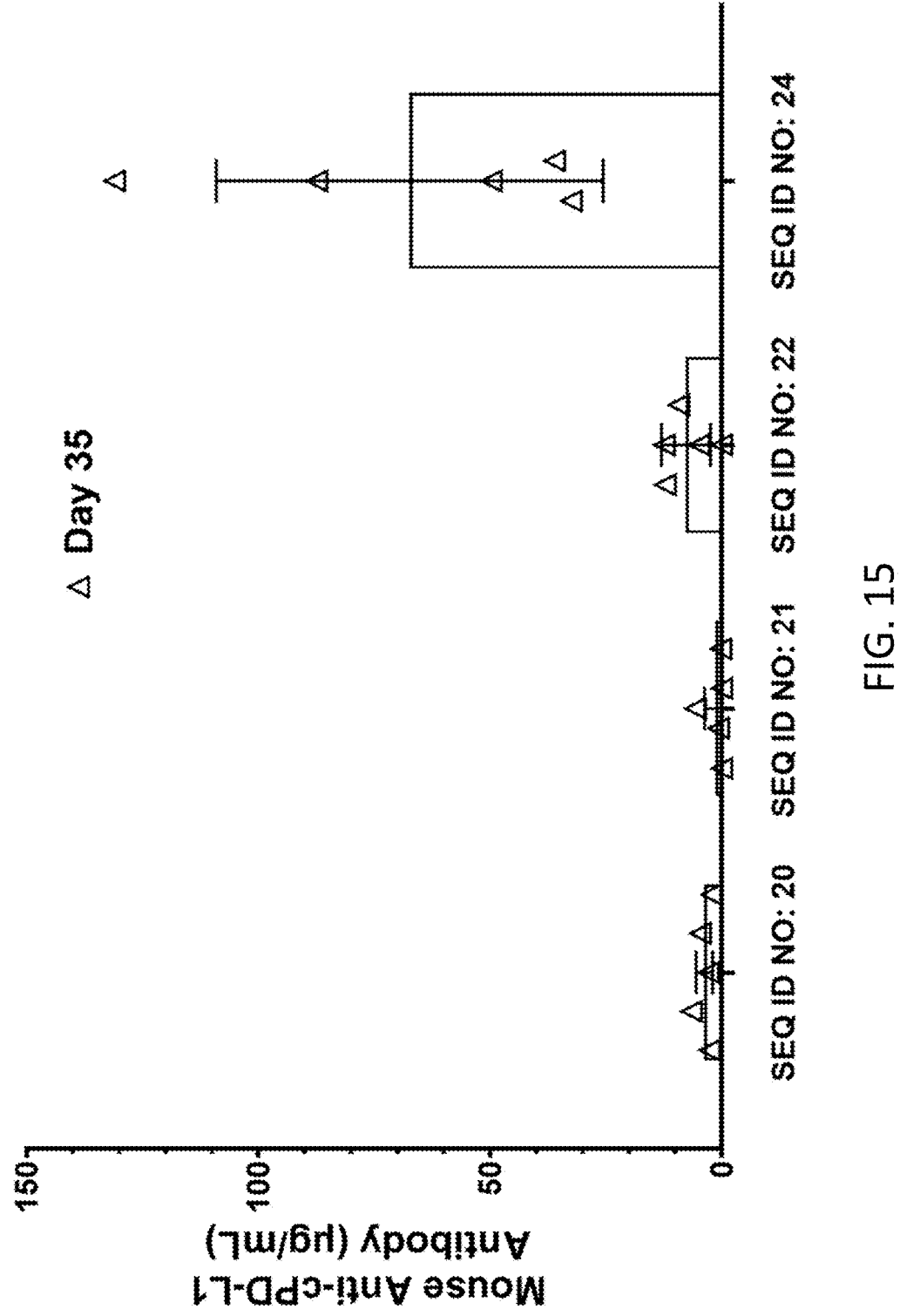
FIG. 15 is a graph showing mean mouse anti-cPD-L1 antibody titer values detected (μg/mL) on Day 35 when the PD-L1 fusion proteins of SEQ ID NO: 20, SEQ ID NO: 21, SEQ ID NO: 22 and SEQ ID NO: 24 were administered to mice on Day 0 and Day 21 according to Example 12.
Figure 20:
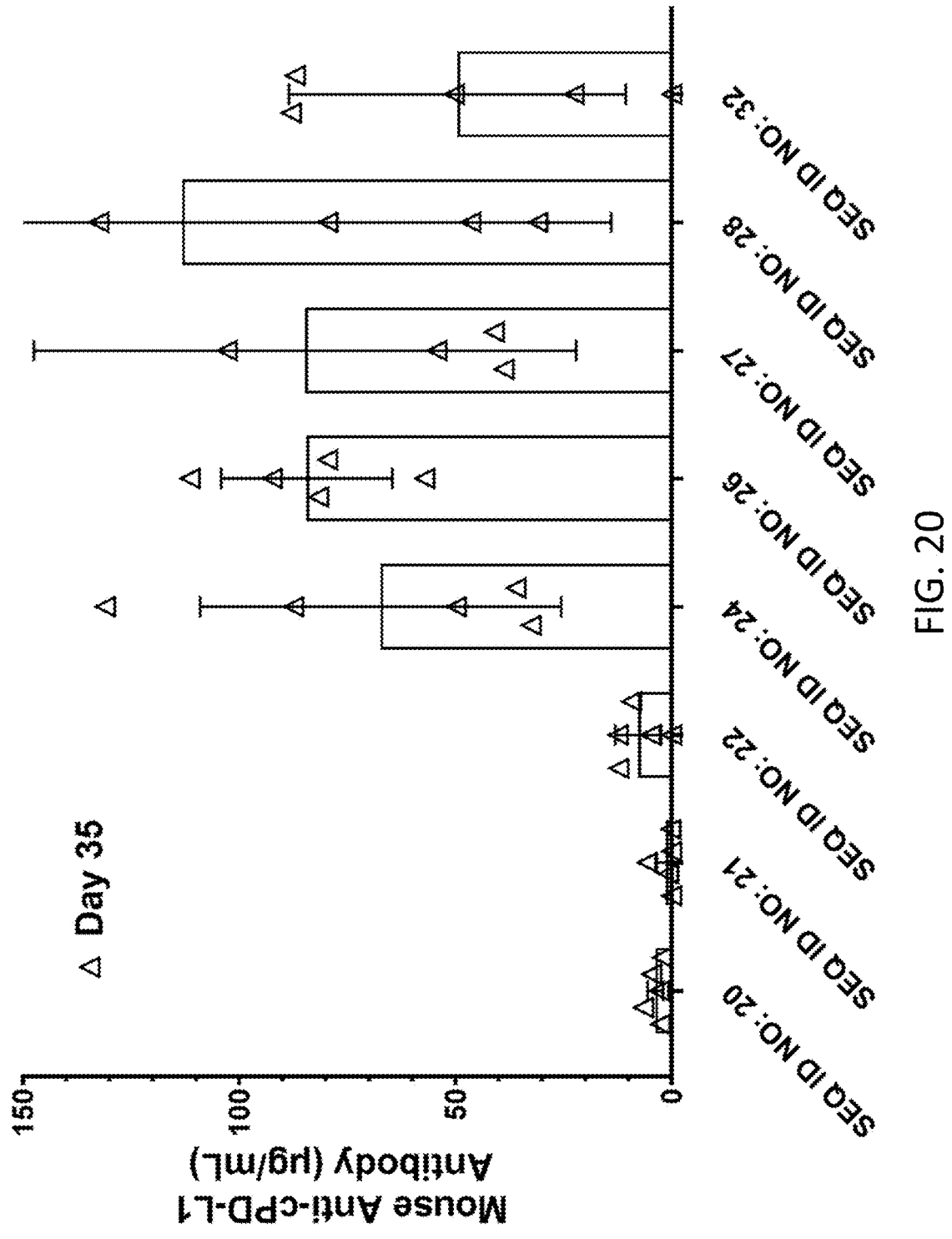
FIG. 20 is a graph showing mean mouse anti-cPD-L1 antibody titer values detected (μg/mL) on Day 35 when the PD-L1 fusion proteins of SEQ ID NO: 20, SEQ ID NO: 21, SEQ ID NO: 22, SEQ ID NO: 24, SEQ ID NO: 26, SEQ ID NO: 27, SEQ ID NO: 28 and SEQ ID NO: 32 were administered to mice on Day 0 and Day 21 according to Example 12.

The PD-L1 analog-Fc fusion protein of SEQ ID NO: 20 was manufactured in CHO cells according to Example 1 and was purified according to Example 3. The Fc fusion protein structure of the PD-L1 analog-Fc fusion protein of SEQ ID NO: 20 was confirmed according to Example 5, and sequence identification is performed according to Example 6. The resultant yield of the fusion protein produced was 150 mg/L, which is above both the design goal of 50 mg/L and the preferred design goal of 100 mg/L. As this sequence met the design goal of an acceptable manufacturing yield, the immunogenicity of the PD-L1 analog fusion protein was assessed. A pharmaceutical composition of SEQ ID NO: 20 was administered to mice according to the method of Example 12, and anti-canine-PD-L1 (anti-cPD-L1) IgG antibody titers were measured according to Example 9. The mean mouse anti-cPD-L1 antibody titer on Day 35 was calculated as 3.8 µg/mL, and the mean mouse anti-cPD-L1 antibody titer on Day 107 was calculated as 46.1 µg/mL. This data is shown on FIG. 15, FIG. 20 and FIG. 21. The levels of immunogenicity were not significant and therefore did not meet the design goal.

In a seventh attempt to create a PD-L1 analog-Fc fusion protein, the canine PD-L1 protein of SEQ ID NO: 3 was truncated further to cover a smaller section of the extracellular region of the canine PD-L1. The fragment did not include any part of the TM-domain or the section with the cysteine-cysteine (CC) motif, so the fragment was not mutated. The resulting canine PD-L1 analog is SEQ ID NO: 14, is shown below:

```
                                        (SEQ ID NO: 14)
LIGYGGADYKRITLKVHAPYRNISQRISVDPVTS
```

The canine PD-L1 analog of SEQ ID NO: 14 was linked using the peptide linker GGGGQGGGSGGQGGGGG (SEQ ID NO: 6) to the canine IgGB Fc fragment of SEQ ID NO: 1. The resultant PD-L1 analog-Fc fusion protein is given below as SEQ ID NO: 21.

```
                                        (SEQ ID NO: 21)
LIGYGGADYKRITLKVHAPYRNISQRISVDPVTSGGGGQGGGSGGQGGG

GGDCPKCPAPEMLGGPSVFIFPPKPKDTLLIARTPEVTCVVVDLDPEDP

EVQISWFVDGKQMQTAKTQPREEQFNGTYRVVSVLPIGHQDWLKGKQFT

CKVNNKALPSPIERTISKARGQAHQPSVYVLPPSREELSKNTVSLTCLI

KDFFPPDIDVEWQSNGQQEPESKYRTTPPQLDEDGSYFLYSKLSVDKSR

WQRGDTFICAVMHEALHNHYTQESLSHSPG.
```

The PD-L1 analog-Fc fusion protein of SEQ ID NO: 21 was manufactured in CHO cells according to Example 1 and was purified according to Example 3. The Fc fusion protein structure of the PD-L1 analog-Fc fusion protein of SEQ ID NO: 21 was confirmed according to Example 5, and sequence identification is performed according to Example 6. The resultant yield of the fusion protein produced was 148 mg/L, which is above both the design goal of 50 mg/L and the preferred design goal of 100 mg/L. As this sequence met the design goal of an acceptable manufacturing yield, the immunogenicity of the PD-L1 analog fusion protein was assessed. A pharmaceutical composition of SEQ ID NO: 21 was administered to mice according to the method of Example 12, and anti-cPD-L1 IgG antibody titers were measured according to Example 9. The mean mouse anti-cPD-L1 antibody titer on Day 35 was calculated as 1.3 µg/mL, and the mean mouse anti-cPD-L1 antibody titer on Day 107 was calculated as 5.5 µg/mL. This data is shown on FIG. 15, FIG. 20 and FIG. 21. The levels of immunogenicity were not significant and therefore did not meet the design goal.

In an eighth attempt to create a PD-L1 analog-Fc fusion protein, the PD-L1 analog of SEQ ID NO: 13 which was previously utilized in the PD-L1 analog fusion protein of SEQ ID NO: 20 which demonstrated acceptable manufacturing yield but had a low immunogenicity was utilized in combination with a shorter linker. The shorter linker was utilized in an attempt to increase the manufacturing yield. The canine PD-L1 analog of SEQ ID NO: 13 is shown below, with the cysteine (C) to arginine (R) substitution (C95R, shown in bold) introduced to eliminate the cysteine-cysteine (CC) motif and remove a potential unpaired cysteine moiety at positions 95 and 96:

(SEQ ID NO: 13)

FTITVSKDLYVVEYGGNVTMECKFPVEKQLNLFALIVYWEMEDKKIIQFV

NGKEDLKVQHSSYSQRAQLLKDQLFLGKAALQITDVRLQDAGVYRCLIGY

GGADYKRITLKVHAPYRNISQRISVDPVTS

The canine PD-L1 analog of SEQ ID NO: 13 was linked using the short peptide linker QGGGSGGQ (SEQ ID NO: 7) to the canine IgGB Fc fragment of SEQ ID NO: 1. The resultant PD-L1 analog-Fc fusion protein is given below as SEQ ID NO: 22.

(SEQ ID NO: 22)

FTITVSKDLYVVEYGGNVTMECKFPVEKQLNLFALIVYWEMEDKKIIQFV

NGKEDLKVQHSSYSQRAQLLKDQLFLGKAALQITDVRLQDAGVYRCLIGY

GGADYKRITLKVHAPYRNISQRISVDPVTSQGGGSGGQDCPKCPAPEMLG

GPSVFIFPPKPKDTLLIARTPEVTCVVVDLDPEDPEVQISWFVDGKQMQT

AKTQPREEQFNGTYRVVSVLPIGHQDWLKGKQFTCKVNNKALPSPIERTI

SKARGQAHQPSVYVLPPSREELSKNTVSLTCLIKDFFPPDIDVEWQSNGQ

QEPESKYRTTPPQLDEDGSYFLYSKLSVDKSRWQRGDTFICAVMHEALHN

HYTQESLSHSPG.

The PD-L1 analog-Fc fusion protein of SEQ ID NO: 22 was manufactured in CHO cells according to Example 1 and was purified according to Example 3. The Fc fusion protein structure of the PD-L1 analog-Fc fusion protein of SEQ ID NO: 22 was confirmed according to Example 5, and sequence identification is performed according to Example 6. The resultant yield of the fusion protein produced was 220 mg/L, which is above both the design goal of 50 mg/L and the preferred design goal of 100 mg/L. As this sequence met the design goal of an acceptable manufacturing yield, the immunogenicity of the PD-L1 analog fusion protein was assessed. A pharmaceutical composition of SEQ ID NO: 22 was administered to mice according to the method of Example 12, and anti-cPD-L1 IgG antibody titers were measured according to Example 9. The mean mouse anti-cPD-L1 antibody titer on Day 35 was calculated as 7.8 µg/mL, and the mean mouse anti-cPD-L1 antibody titer on Day 107 was calculated as 66.8 µg/mL. This data is shown on FIG. 15, FIG. 20 and FIG. 21. The levels of immunogenicity were not significant and therefore did not meet the design goal.

In a further attempt to create a PD-L1 analog-Fc fusion protein, a different fragment of the canine PD-L1 protein of SEQ ID NO: 3 was used. This PD-L1 fragment was a truncated section of the extracellular region of the canine PD-L1 and included part of the TM-domain. The fragment did not include the section with the cysteine-cysteine (CC) motif, so the fragment was not mutated. The resulting PD-L1 analog is SEQ ID NO: 23 is shown below:

(SEQ ID NO: 23)

LIGYGGADYKRITLKVHAPYRNISQRISVDPVTSEHELMCQAEGYPEAEV

IWTSSDHRVLSGKTTITNSNREEKLFNVTSTLNINATANEIFYCTFQRSG

PEENNTAELVIPERLPVPASERTHFMILGPF

A comparison of the PD-L1 analogs of SEQ ID NO: 12, SEQ ID NO: 13, SEQ ID NO: 14 and SEQ ID NO: 23 is shown in FIG. 6A and FIG. 6B.

The PD-L1 analog of SEQ ID NO: 23 was linked using the peptide linker GGGGQGGGSGGQGGGGG (SEQ ID NO: 6) to the canine IgGB Fc fragment of SEQ ID NO: 1. The resultant PD-L1 analog-Fc fusion protein is given below as SEQ ID NO: 24.

(SEQ ID NO: 24)

LIGYGGADYKRITLKVHAPYRNISQRISVDPVTSEHELMCQAEGYPEAEV

IWTSSDHRVLSGKTTITNSNREEKLFNVTSTLNINATANEIFYCTFQRSG

PEENNTAELVIPERLPVPASERTHFMILGPFGGGGQGGGSGGQGGGGGDC

PKCPAPEMLGGPSVFIFPPKPKDTLLIARTPEVTCVVVDLDPEDPEVQIS

WFVDGKQMQTAKTQPREEQFNGTYRVVSVLPIGHQDWLKGKQFTCKVNNK

ALPSPIERTISKARGQAHQPSVYVLPPSREELSKNTVSLTCLIKDFFPPD

IDVEWQSNGQQEPESKYRTTPPQLDEDGSYFLYSKLSVDKSRWQRGDTFI

CAVMHEALHNHYTQESLSHSPG.

A comparison of the PD-L1 analog-Fc fusion proteins of SEQ ID NO: 19, SEQ ID NO: 20, SEQ ID NO: 21, SEQ ID NO: 22 and SEQ ID NO: 24 is shown in FIG. 7A, FIG. 7B and FIG. 7C.

The PD-L1 analog-Fc fusion protein of SEQ ID NO: 24 was manufactured in CHO cells according to Example 1 and was purified according to Example 3. The Fc fusion protein structure of the PD-L1 analog-Fc fusion protein of SEQ ID NO: 24 was confirmed according to Example 5, and sequence identification is performed according to Example 6. The resultant yield of the fusion protein produced was 197 mg/L, which is above both the design goal of 50 mg/L and the preferred design goal of 100 mg/L. As this sequence met the design goal of an acceptable manufacturing yield, the immunogenicity of the PD-L1 analog fusion protein was assessed. A pharmaceutical composition of SEQ ID NO: 24 was administered to mice according to the method of Example 12, and anti-cPD-L1 IgG antibody titers were measured according to Example 9. Unexpectedly the mean mouse anti-cPD-L1 antibody titer on Day 35 was calculated as 67.3 µg/mL, and the mean mouse anti-dPD-L1 antibody titer on Day 107 was calculated as 614.7 µg/mL. This data is shown on FIG. 15, FIG. 20 and FIG. 21. This level of immunogenicity was higher than previously tested sequences and showed a significant immunogenic response. The immunogenicity of the PD-L1 analog fusion protein in canines was also assessed. A pharmaceutical composition of SEQ ID NO: 24 was administered to canines according to the method of Example 13, and anti-cPD-L1 IgG antibody titers were measured according to Example 10. Unexpectedly the canine anti-cPD-L1 antibody titer on Day 28 was calculated as 8.2 µg/mL, on Day 56 as 11.0 µg/mL, and on Day 70 as 17.2 µg/mL. This data is shown on FIG. 22. This level of immunogenicity showed a significant immunogenic response. This sequence met the preferred design goal of a PD-L1 analog-Fc fusion protein with a manufacturing titer of over 100 mg/L and which is capable of inducing an immunogenic response.

In a further attempt to create a PD-L1 analog-Fc fusion protein, a different larger fragment of the canine PD-L1 protein of SEQ ID NO: 3 was used. This PD-L1 fragment was a truncated section of the extracellular region of the canine PD-L1 and included part of the TM-domain. In addition, the canine PD-L1 analog was mutated at position 95 with a cysteine (C) to arginine (R) substitution (C95R) to eliminate the cysteine-cysteine (CC) motif at position 95 and 96, so as to remove a potential unpaired cysteine moiety. The resulting PD-L1 analog is SEQ ID NO: 25 with the C95R mutation shown in bold below:

```
                                    (SEQ ID NO: 25)
FTITVSKDLYVVEYGGNVTMECKFPVEKQLNLFALIVYWEMEDKKIIQFV

NGKEDLKVQHSSYSQRAQLLKDQLFLGKAALQITDVRLQDAGVYRCLIGY

GGADYKRITLKVHAPYRNISQRISVDPVTSEHELMCQAEGYPEAEVIWTS

SDHRVLSGKTTITNSNREEKLFNVTSTLNINATANEIFYCTFQRSGPEEN

NTAELVIPERLPVPASERTHFMILGPF
```

A comparison of the PD-L1 analogs of SEQ ID NO: 12, SEQ ID NO: 13, SEQ ID NO: 14 and SEQ ID NO: 25 is shown in FIG. 8A and FIG. 8B.

The PD-L1 analog of SEQ ID NO: 25 was linked using the peptide linker QGGGSGGQ (SEQ ID NO: 7) to the canine IgGB Fc fragment of SEQ ID NO: 1. The resultant PD-L1 analog-Fc fusion protein is given below as SEQ ID NO: 26.

```
                                    (SEQ ID NO: 26)
FTITVSKDLYVVEYGGNVTMECKFPVEKQLNLFALIVYWEMEDKKIIQFV

NGKEDLKVQHSSYSQRAQLLKDQLFLGKAALQITDVRLQDAGVYRCLIGY

GGADYKRITLKVHAPYRNISQRISVDPVTSEHELMCQAEGYPEAEVIWTS

SDHRVLSGKTTITNSNREEKLFNVTSTLNINATANEIFYCTFQRSGPEEN

NTAELVIPERLPVPASERTHFMILGPFQGGGSGGQDCPKCPAPEMLGGPS

VFIFPPKPKDTLLIARTPEVTCVVVDLDPEDPEVQISWFVDGKQMQTAKT

QPREEQFNGTYRVVSVLPIGHQDWLKGKQFTCKVNNKALPSPIERTISKA

RGQAHQPSVYVLPPSREELSKNTVSLTCLIKDFFPPDIDVEWQSNGQQEP

ESKYRTTPPQLDEDGSYFLYSKLSVDKSRWQRGDTFICAVMHEALHNHYT

QESLSHSPG.
```

A comparison of the PD-L1 analog-Fc fusion proteins of SEQ ID NO: 19, SEQ ID NO: 20, SEQ ID NO: 21, SEQ ID NO: 22 and SEQ ID NO: 26 is shown in FIG. 9A, FIG. 9B and FIG. 9C.

Figure 16:
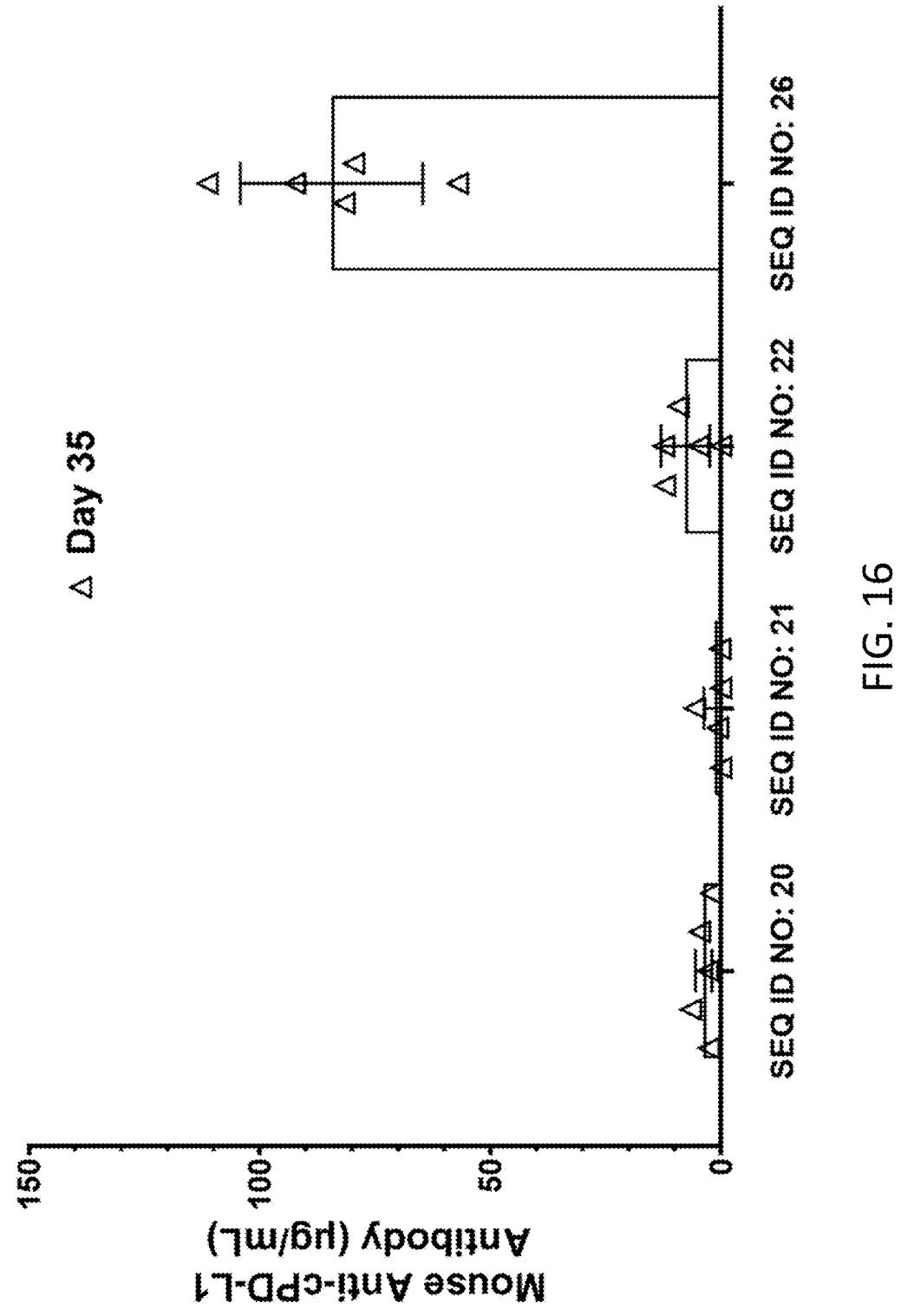
FIG. 16 is a graph showing mean mouse anti-cPD-L1 antibody titer values detected (μg/mL) on Day 35 when the PD-L1 fusion proteins of SEQ ID NO: 20, SEQ ID NO: 21, SEQ ID NO: 22 and SEQ ID NO: 26 were administered to mice on Day 0 and Day 21 according to Example 12.

The PD-L1 analog-Fc fusion protein of SEQ ID NO: 26 was manufactured in CHO cells according to Example 1 and was purified according to Example 3. The Fc fusion protein structure of the PD-L1 analog-Fc fusion protein of SEQ ID NO: 26 was confirmed according to Example 5, and sequence identification is performed according to Example 6. The resultant yield of the fusion protein produced was 407 mg/L, which is above both the design goal of 50 mg/L and the preferred design goal of 100 mg/L. As this sequence met the design goal of an acceptable manufacturing yield, the immunogenicity of the PD-L1 analog fusion protein was assessed. A pharmaceutical composition of SEQ ID NO: 26 was administered to mice according to the method of Example 12, and anti-cPD-L1 IgG antibody titers were measured according to Example 9. Unexpectedly the mean mouse anti-cPD-L1 antibody titer on Day 35 was calculated as 84.4 μg/mL, and the mean mouse anti-cPD-L1 antibody titer on Day 107 was calculated as 723.2 μg/mL. This data is shown on FIG. 16, FIG. 20 and FIG. 21. This level of immunogenicity was high and showed a significant immunogenic response. The immunogenicity of the PD-L1 analog fusion protein in canines was also assessed. A pharmaceutical composition of SEQ ID NO: 26 was administered to canines according to the method of Example 13, and anti-cPD-L1 IgG antibody titers were measured according to Example 10. Unexpectedly the canine anti-cPD-L1 antibody titer on Day 28 was calculated as 2.1 μg/mL, on Day 56 as 2.8 μg/mL, and on Day 70 as 3.7 μg/mL. This data is shown on FIG. 22. This level of immunogenicity showed a significant immunogenic response. This sequence met the preferred design goal of a PD-L1 analog-Fc fusion protein with a manufacturing titer of over 100 mg/L and which is capable of inducing an immunogenic response.

In a further attempt to create a PD-L1 analog-Fc fusion protein, the PD-L1 analog of SEQ ID NO: 25 was linked using the peptide linker GGGGQGGGSGGQGGGGG (SEQ ID NO: 6) to the canine IgGB Fc fragment of SEQ ID NO: 1. The resultant PD-L1 analog-Fc fusion protein is given below as SEQ ID NO: 27.

```
                                    (SEQ ID NO: 27)
FTITVSKDLYVVEYGGNVTMECKFPVEKQLNLFALIVYWEMEDKKIIQFV

NGKEDLKVQHSSYSQRAQLLKDQLFLGKAALQITDVRLQDAGVYRCLIGY

GGADYKRITLKVHAPYRNISQRISVDPVTSEHELMCQAEGYPEAEVIWTS

SDHRVLSGKTTITNSNREEKLFNVTSTLNINATANEIFYCTFQRSGPEEN

NTAELVIPERLPVPASERTHFMILGPFGGGGQGGGSGGQGGGGGDCPKCP

APEMLGGPSVFIFPPKPKDTLLIARTPEVTCVVVDLDPEDPEVQISWFVD

GKQMQTAKTQPREEQFNGTYRVVSVLPIGHQDWLKGKQFTCKVNNKALPS

PIERTISKARGQAHQPSVYVLPPSREELSKNTVSLTCLIKDFFPPDIDVE

WQSNGQQEPESKYRTTPPQLDEDGSYFLYSKLSVDKSRWQRGDTFICAVM

HEALHNHYTQESLSHSPG.
```

A comparison of the PD-L1 analog-Fc fusion proteins of SEQ ID NO: 19, SEQ ID NO: 20, SEQ ID NO: 21, SEQ ID NO: 22 and SEQ ID NO: 27 is shown in FIG. 10A, FIG. 10B and FIG. 10C.

Figure 17:
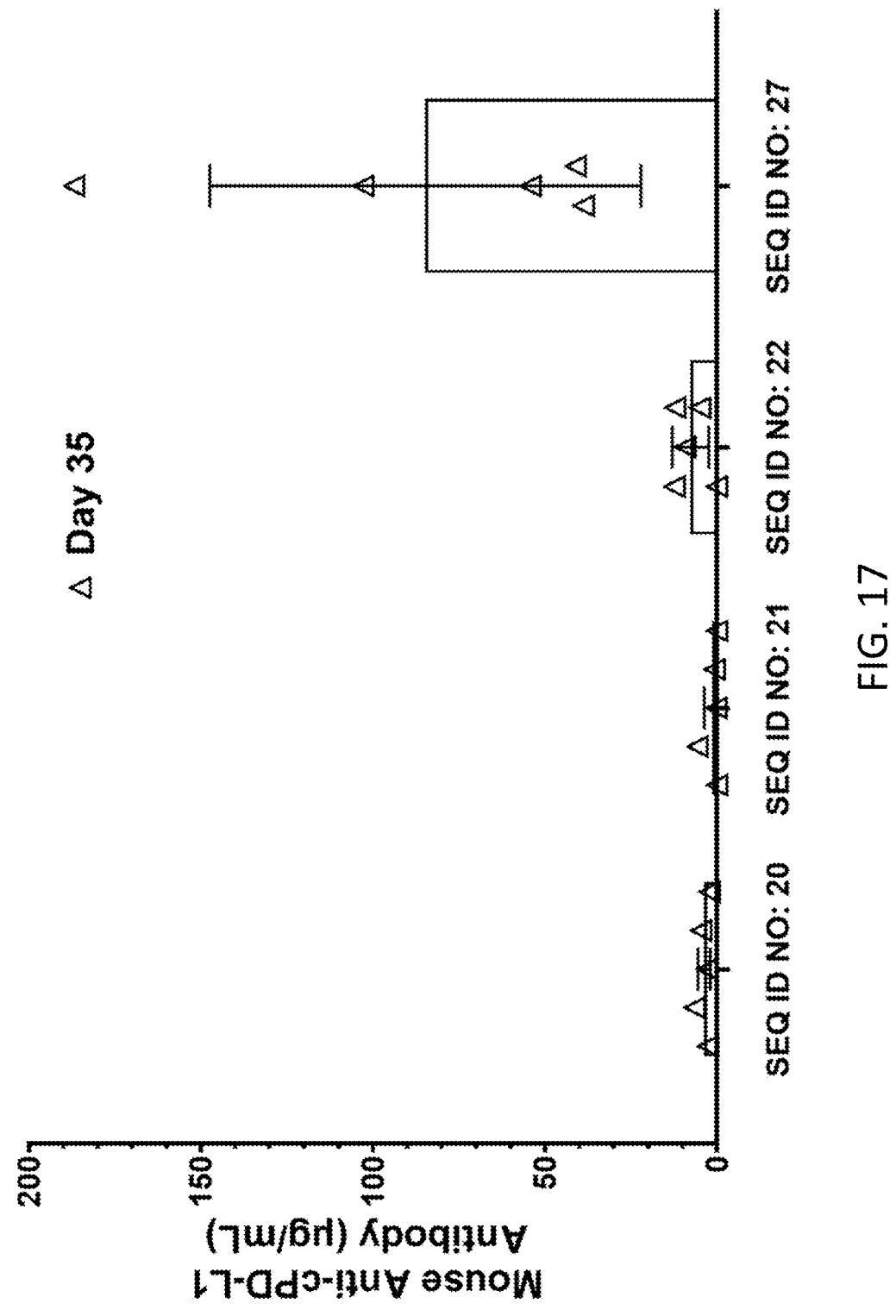
FIG. 17 is a graph showing mean mouse anti-cPD-L1 antibody titer values detected (μg/mL) on Day 35 when the PD-L1 fusion proteins of SEQ ID NO: 20, SEQ ID NO: 21, SEQ ID NO: 22 and SEQ ID NO: 27 were administered to mice on Day 0 and Day 21 according to Example 12.

The PD-L1 analog-Fc fusion protein of SEQ ID NO: 27 was manufactured in CHO cells according to Example 1 and was purified according to Example 3. The Fc fusion protein structure of the PD-L1 analog-Fc fusion protein of SEQ ID NO: 27 was confirmed according to Example 5, and sequence identification is performed according to Example 6. The resultant yield of the fusion protein produced was 379 mg/L, which is above both the design goal of 50 mg/L and the preferred design goal of 100 mg/L. As this sequence met the design goal of an acceptable manufacturing yield, the immunogenicity of the PD-L1 analog fusion protein was assessed. A pharmaceutical composition of SEQ ID NO: 27 was administered to mice according to the method of Example 12, and anti-cPD-L1 IgG antibody titers were measured according to Example 9. Unexpectedly the mean mouse anti-cPD-L1 antibody titer on Day 35 was calculated as 84.8 μg/mL, and the mean mouse anti-cPD-L1 antibody titer on Day 107 was calculated as 581.6 μg/mL. This data is shown on FIG. 17, FIG. 20 and FIG. 21. This level of immunogenicity was high and showed a significant immunogenic response. The immunogenicity of the PD-L1 analog fusion protein in canines was also assessed. A pharmaceutical composition of SEQ ID NO: 27 was administered to canines according to the method of Example 13, and anti-cPD-L1 IgG antibody titers were measured according to Example 10. Unexpectedly the canine anti-cPD-L1 antibody titer on Day 28 was calculated as 2.9 μg/mL, on Day 56 as 8.9 µg/mL, and on Day 70 as 16.7 µg/mL. This data is shown on FIG. 22. This level of immunogenicity showed a significant immunogenic response. This sequence met the preferred design goal of a PD-L1 analog-Fc fusion protein with a manufacturing titer of over 100 mg/L and which is capable of inducing an immunogenic response.

In a further attempt to create a PD-L1 analog-Fc fusion protein, the PD-L1 analog of SEQ ID NO: 25 was linked using the peptide linker GGQGGGSGGQGGGGG (SEQ ID NO: 30) to the human IgG1 Fc fragment of SEQ ID NO: 29. The shorter linker was utilized in an attempt to increase the manufacturing yield. It was expected that using a human IgG would cause the PD-L1 analog-Fc fusion protein to potentially be more immunogenic in animals (e.g., mice or dogs) than using a canine IgG. Human IgG1 was chosen as it is known to have greater immunogenicity than the other human IgG form (IgG2, IgG3 and IgG4). In the human IgG1 of SEQ ID NO: 29, the C-terminus lysine on the native human IgG1 was eliminated. The C-terminal lysine that is found in native IgG isotype Fc fragment amino acid sequences (i.e., the lysine that represents the last amino acid of the Fc fragment sequence) is known to result in the accidental production of unwanted amino acid sequence variants during manufacturing (e.g., Fc fragments containing the C-terminal lysine becoming mixed with Fc fragments where the C-terminal lysine is omitted) which can occur during production of the desired protein within cells (Dick, L W., (2008) *Biotechnol Bioeng.* August 15;100(6) pp1132-43). Therefore, it was expected that removing the C-terminal lysine would improve manufacturing yield and purity. The human IgG1 Fc fragment sequence lacking a C-terminal lysine is given in SEQ ID NO: 29 below:

```
                                  (SEQ ID NO: 29)
DKTHTCPPCPAPELLGGPSVFLFPPKPKDTLMISRTPEVTCVVVDVSHED

PEVKFNWYVDGVEVHNAKTKPREEQYNSTYRVVSVLTVLHQDWLNGKEYK

CKVSNKALPAPIEKTISKAKGQPREPQVYTLPPSRDELTKNQVSLTCLVK

GFYPSDIAVEWESNGQPENNYKTTPPVLDSDGSFFLYSKLTVDKSRWQQG

NVFSCSVMHEALHNHYTQKSLSLSPG.
```

The resultant PD-L1 analog-Fc fusion protein is given below as SEQ ID NO: 28.

```
                                  (SEQ ID NO: 28)
FTITVSKDLYVVEYGGNVTMECKFPVEKQLNLFALIVYWEMEDKKIIQFV

NGKEDLKVQHSSYSQRAQLLKDQLFLGKAALQITDVRLQDAGVYRCLIGY

GGADYKRITLKVHAPYRNISQRISVDPVTSEHELMCQAEGYPEAEVIWTS

SDHRVLSGKTTITNSNREEKLFNVTSTLNINATANEIFYCTFQRSGPEEN

NTAELVIPERLPVPASERTHFMILGPFGGQGGGSGGQGGGGGDKTHTCPP

CPAPELLGGPSVFLFPPKPKDTLMISRTPEVTCVVVDVSHEDPEVKFNWY

VDGVEVHNAKTKPREEQYNSTYRVVSVLTVLHQDWLNGKEYKCKVSNKAL

PAPIEKTISKAKGQPREPQVYTLPPSRDELTKNQVSLTCLVKGFYPSDIA

VEWESNGQPENNYKTTPPVLDSDGSFFLYSKLTVDKSRWQQGNVFSCSVM

HEALHNHYTQKSLSLSPG.
```

A comparison of the PD-L1 analog-Fc fusion proteins of SEQ ID NO: 19, SEQ ID NO: 20, SEQ ID NO: 21, SEQ ID NO: 22 and SEQ ID NO: 28 is shown in FIG. 11A, FIG. 11B and FIG. 11C.

Figure 18:
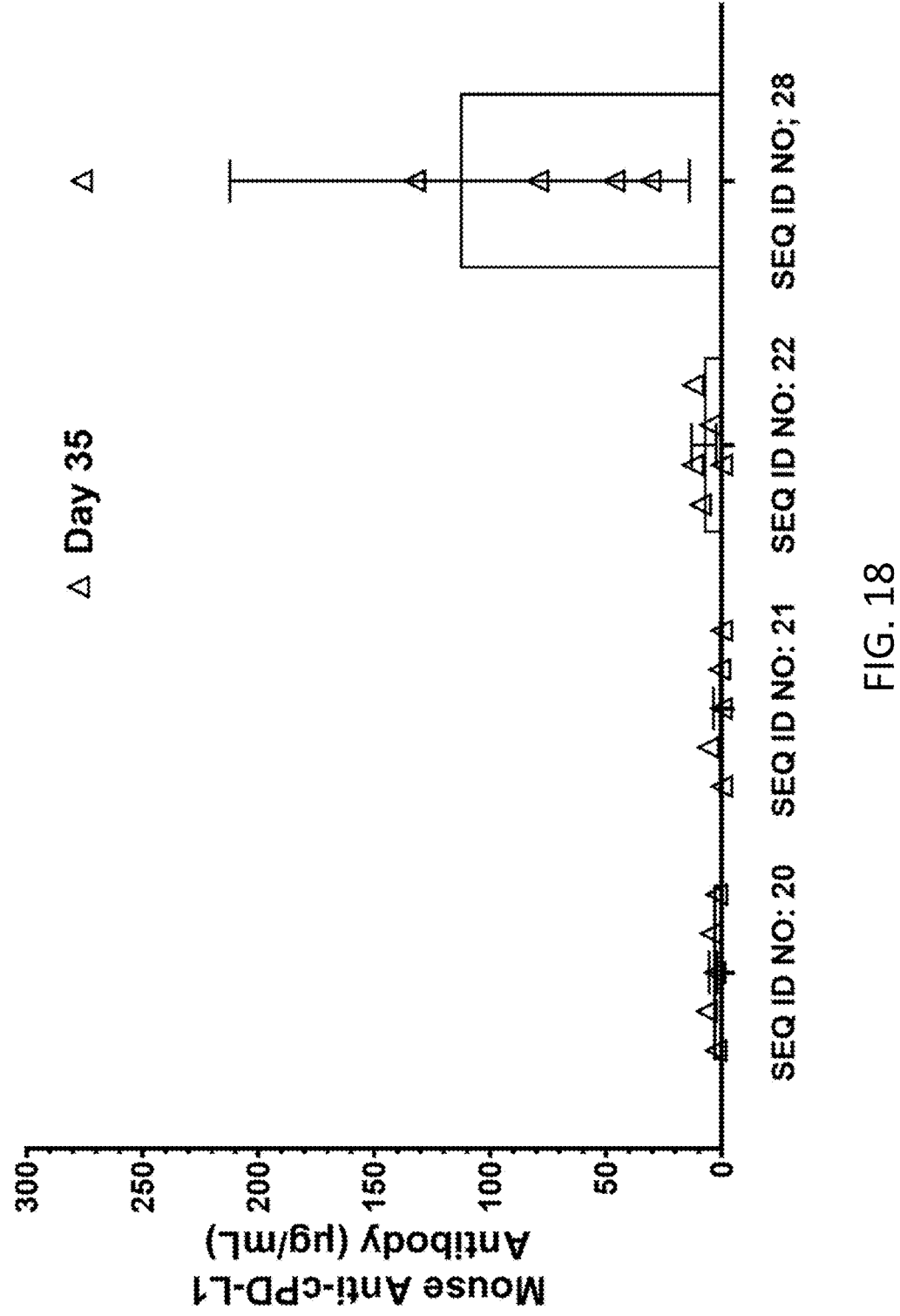
FIG. 18 is a graph showing mean mouse anti-cPD-L1 antibody titer values detected (μg/mL) on Day 35 when the PD-L1 fusion proteins of SEQ ID NO: 20, SEQ ID NO: 21, SEQ ID NO: 22 and SEQ ID NO: 28 were administered to mice on Day 0 and Day 21 according to Example 12.

The PD-L1 analog-Fc fusion protein of SEQ ID NO: 28 was manufactured in CHO cells according to Example 1 and was purified according to Example 3. The Fc fusion protein structure of the PD-L1 analog-Fc fusion protein of SEQ ID NO: 28 was confirmed according to Example 5, and sequence identification is performed according to Example 6. The resultant yield of the fusion protein produced was 70 mg/L, which is above the design goal of 50 mg/L. As this sequence met the design goal of an acceptable manufacturing yield, the immunogenicity of the PD-L1 analog fusion protein was assessed. A pharmaceutical composition of SEQ ID NO: 28 was administered to mice according to the method of Example 12, and anti-cPD-L1 IgG antibody titers were measured according to Example 9. Unexpectedly the mean mouse anti-cPD-L1 antibody titer on Day 35 was calculated as 113.1 µg/mL, and the mean mouse anti-cPD-L1 antibody titer on Day 107 was calculated as 514.8 µg/mL. This data is shown on FIG. 18, FIG. 20 and FIG. 21. This level of immunogenicity was high and showed a significant immunogenic response. This sequence met the design goal of a PD-L1 analog-Fc fusion protein with a manufacturing titer of over 50 mg/L and which is capable of inducing an immunogenic response.

In a further attempt to create a PD-L1 analog-Fc fusion protein, a different larger fragment of the canine PD-L1 protein of SEQ ID NO: 3 was used. This PD-L1 fragment was a truncated section of the extracellular region of the canine PD-L1 and included part of the TM-domain. The resulting PD-L1 analog is SEQ ID NO: 31 is shown below:

```
                                  (SEQ ID NO: 31)
FTITVSKDLYVVEYGGNVTMECKFPVEKQLNLFALIVYWEMEDKKIIQFV

NGKEDLKVQHSSYSQRAQLLKDQLFLGKAALQITDVRLQDAGVYCCLIGY

GGADYKRITLKVHAPYRNISQRISVDPVTSEHELMCQAEGYPEAEVIWTS

SDHRVLSGKTTITNSNREEKLFNVTSTLNINATANEIFYCTFQRSGPEEN

NTAELVIPERLPVPASERTHFMILGPF
```

A comparison of the PD-L1 analogs of SEQ ID NO: 12, SEQ ID NO: 13, SEQ ID NO: 14 and SEQ ID NO: 31 is shown in FIG. 12A and FIG. 12B.

The PD-L1 analog of SEQ ID NO: 31 was linked using the peptide linker GGGGQGGGSGGQGGGGG (SEQ ID NO: 6) to the canine IgGB Fc fragment of SEQ ID NO: 1. The resultant PD-L1 analog-Fc fusion protein is given below as SEQ ID NO: 32.

```
                                  (SEQ ID NO: 32)
FTITVSKDLYVVEYGGNVTMECKFPVEKQLNLFALIVYWEMEDKKIIQFV

NGKEDLKVQHSSYSQRAQLLKDQLFLGKAALQITDVRLQDAGVYCCLIGY

GGADYKRITLKVHAPYRNISQRISVDPVTSEHELMCQAEGYPEAEVIWTS

SDHRVLSGKTTITNSNREEKLFNVTSTLNINATANEIFYCTFQRSGPEEN

NTAELVIPERLPVPASERTHFMILGPFGGGGQGGGSGGQGGGGGDCPKCP

APEMLGGPSVFIFPPKPKDTLLIARTPEVTCVVVDLDPEDPEVQISWFVD

GKQMQTAKTQPREEQFNGTYRVVSVLPIGHQDWLKGKQFTCKVNNKALPS

PIERTISKARGQAHQPSVYVLPPSREELSKNTVSLTCLIKDFFPPDIDVE

WQSNGQQPESKYRTTPPQLDEDGSYFLYSKLSVDKSRWQRGDTFICAVM

HEALHNHYTQESLSHSPG.
```

A comparison of the PD-L1 analog-Fc fusion proteins of SEQ ID NO: 19, SEQ ID NO: 20, SEQ ID NO: 21, SEQ ID NO: 22 and SEQ ID NO: 32 is shown in FIG. 13A, FIG. 13B and FIG. 13C.

Figure 19:
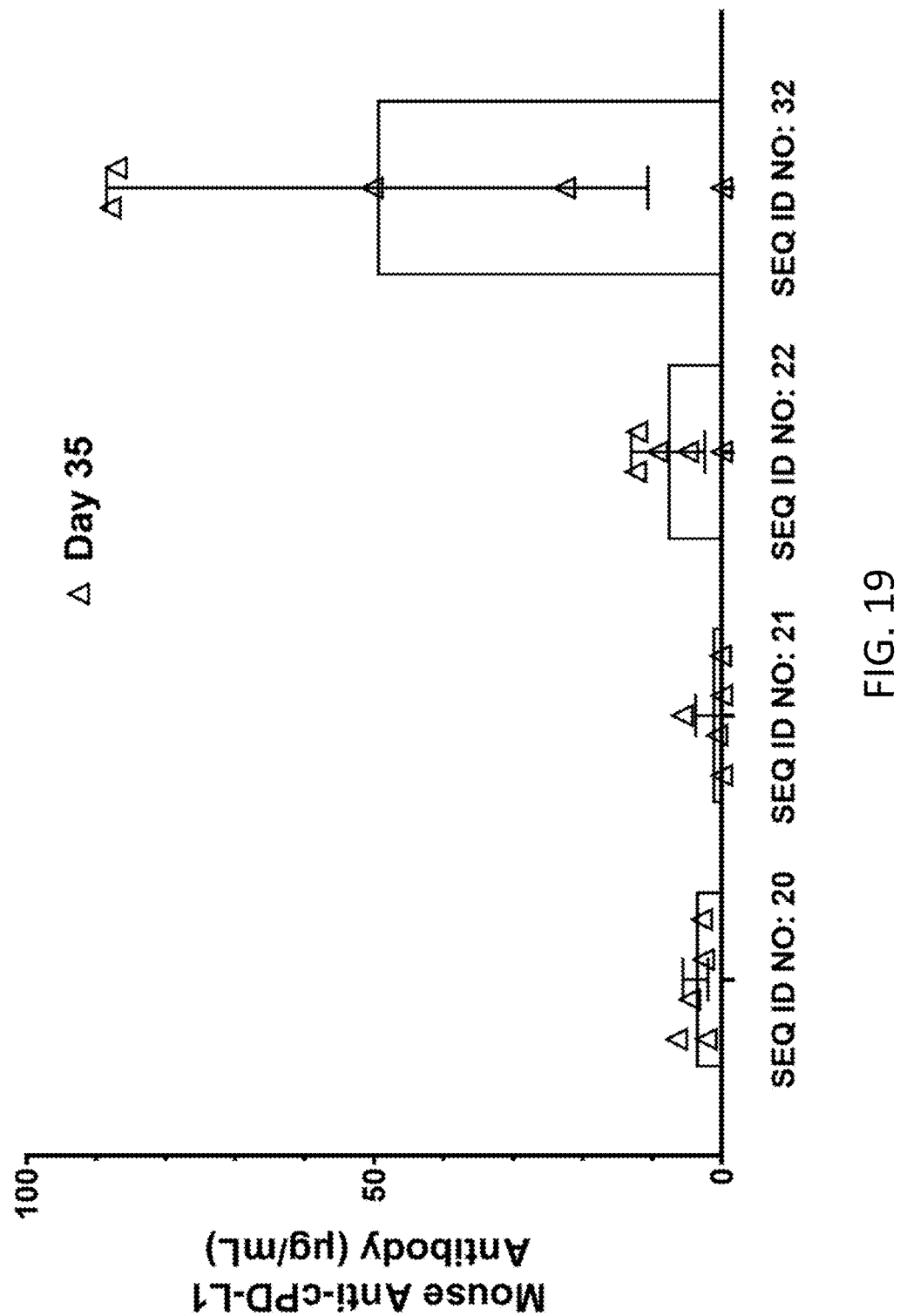
FIG. 19 is a graph showing mean mouse anti-cPD-L1 antibody titer values detected (μg/mL) on Day 35 when the PD-L1 fusion proteins of SEQ ID NO: 20, SEQ ID NO: 21, SEQ ID NO: 22 and SEQ ID NO: 32 were administered to mice on Day 0 and Day 21 according to Example 12.

The PD-L1 analog-Fc fusion protein of SEQ ID NO: 32 was manufactured in CHO cells according to Example 1 and was purified according to Example 3. The Fc fusion protein structure of the PD-L1 analog-Fc fusion protein of SEQ ID NO: 32 was confirmed according to Example 5, and sequence identification is performed according to Example 6. The resultant yield of the fusion protein produced was 173 mg/L, which is above both the design goal of 50 mg/L and the preferred design goal of 100 mg/L. As this sequence met the design goal of an acceptable manufacturing yield, the immunogenicity of the PD-L1 analog fusion protein was assessed. A pharmaceutical composition of SEQ ID NO: 32 was administered to mice according to the method of Example 12, and anti-cPD-L1 IgG antibody titers were measured according to Example 9. Unexpectedly the mean mouse anti-cPD-L1 antibody titer on Day 35 was calculated as 49.6 μg/mL, and the mean mouse anti-cPD-L1 antibody titer on Day 107 was calculated as 326 μg/mL. This data is shown on FIG. 19, FIG. 20 and FIG. 21. This level of immunogenicity was higher than previously tested sequences and showed a significant immunogenic response. This sequence met the preferred design goal of a PD-L1 analog-Fc fusion protein with a manufacturing titer of over 100 mg/L and which is capable of inducing an immunogenic response.

Figure 21:
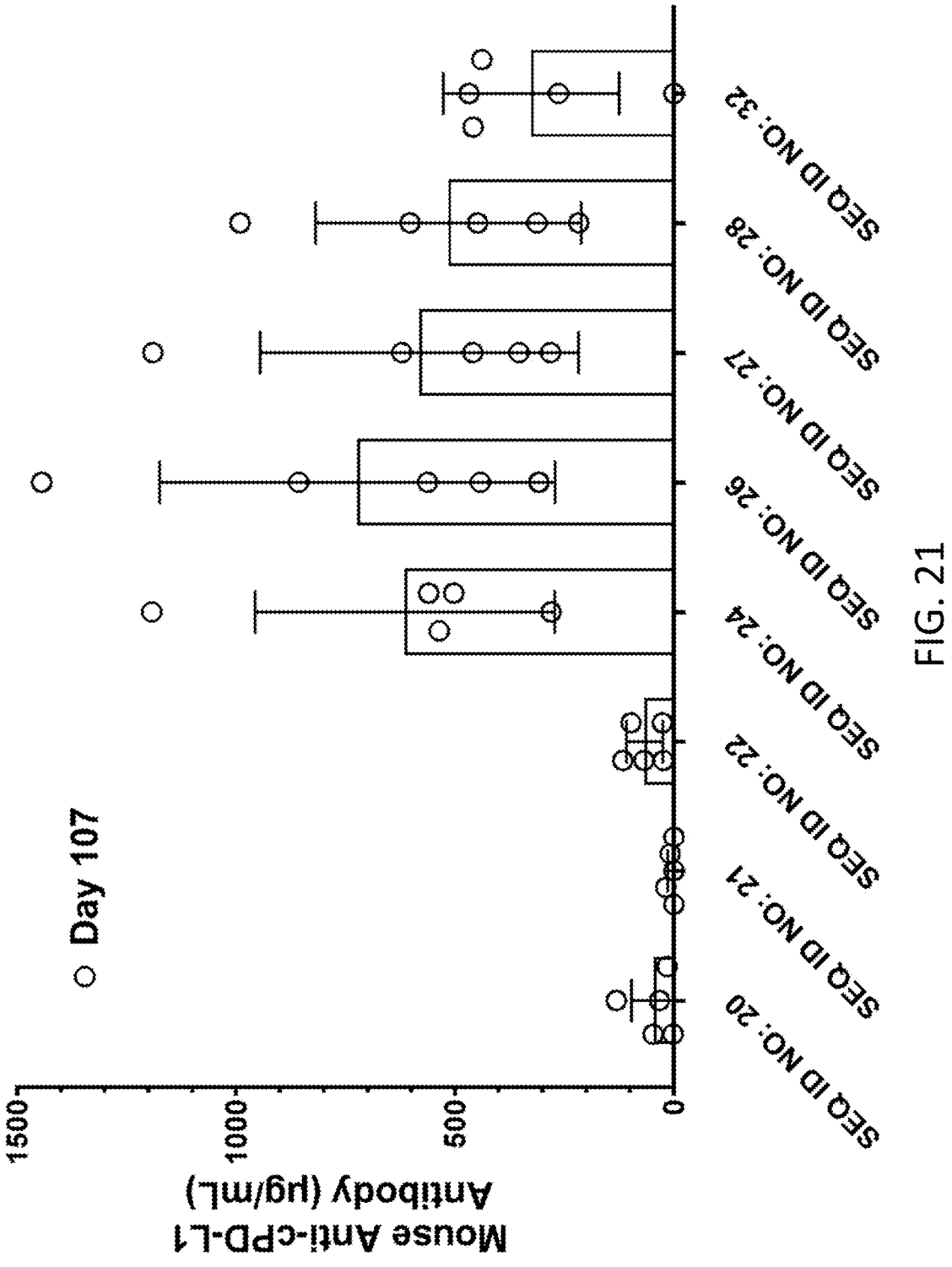
FIG. 21 is a graph showing mean mouse anti-cPD-L1 antibody titer values detected (μg/mL) on Day 107 when the PD-L1 fusion proteins of SEQ ID NO: 20, SEQ ID NO: 21, SEQ ID NO: 22, SEQ ID NO: 24, SEQ ID NO: 26, SEQ ID NO: 27, SEQ ID NO: 28 and SEQ ID NO: 32 were administered to mice on Day 0, Day 21 and Day 42 according to Example 12.

The protein yields of the PD-L1 analog-Fc fusion proteins of SEQ ID NO: 15, SEQ ID NO: 16, SEQ ID NO: 17, SEQ ID NO: 18, SEQ ID NO: 19, SEQ ID NO: 20, SEQ ID NO: 21, SEQ ID NO: 22, SEQ ID NO: 24, SEQ ID NO: 26, SEQ ID NO: 27, SEQ ID NO: 28 and SEQ ID NO: 32 are shown below in Table 1. A sequence comparison of the PD-L1 analog-Fc fusion proteins of SEQ ID NO: 15, SEQ ID NO: 16, SEQ ID NO: 17, and SEQ ID NO: 18 is shown in FIG. 5A, FIG. 5B, and FIG. 5C. A sequence comparison of the PD-L1 analog-Fc fusion proteins of SEQ ID NO: 19, SEQ ID NO: 20, SEQ ID NO: 21, SEQ ID NO: 22, and SEQ ID NO: 24 is shown in FIG. 7A, FIG. 7B, and FIG. 7C. A sequence comparison of the PD-L1 analog-Fc fusion proteins of SEQ ID NO: 19, SEQ ID NO: 20, SEQ ID NO: 21, SEQ ID NO: 22, and SEQ ID NO: 26 is shown in FIG. 9A, FIG. 9B, and FIG. 9C. A sequence comparison of the PD-L1 analog-Fc fusion proteins of SEQ ID NO: 19, SEQ ID NO: 20, SEQ ID NO: 21, SEQ ID NO: 22, and SEQ ID NO: 27 is shown in FIG. 10A, FIG. 10B, and FIG. 10C. A sequence comparison of the PD-L1 analog-Fc fusion proteins of SEQ ID NO: 19, SEQ ID NO: 20, SEQ ID NO: 21, SEQ ID NO: 22, and SEQ ID NO: 28 is shown in FIG. 11A, FIG. 11B, and FIG. 11C. A sequence comparison of the PD-L1 analog-Fc fusion proteins of SEQ ID NO: 19, SEQ ID NO: 20, SEQ ID NO: 21, SEQ ID NO: 22, and SEQ ID NO: 32 is shown in FIG. 13A, FIG. 13B, and FIG. 13C. A comparison of the immunogenicity in mice of SEQ ID NO: 20, SEQ ID NO: 21, SEQ ID NO: 22, SEQ ID NO: 24, SEQ ID NO: 26, SEQ ID NO: 27, SEQ ID NO: 28 and SEQ ID NO: 32 is shown in FIG. 15, FIG. 16, FIG. 17, FIG. 18, FIG. 19 and FIG. 20 and given in Table 4 for Day 35 and is shown in FIG. 21 and given in Table 5 for Day 107.

Figure 22:
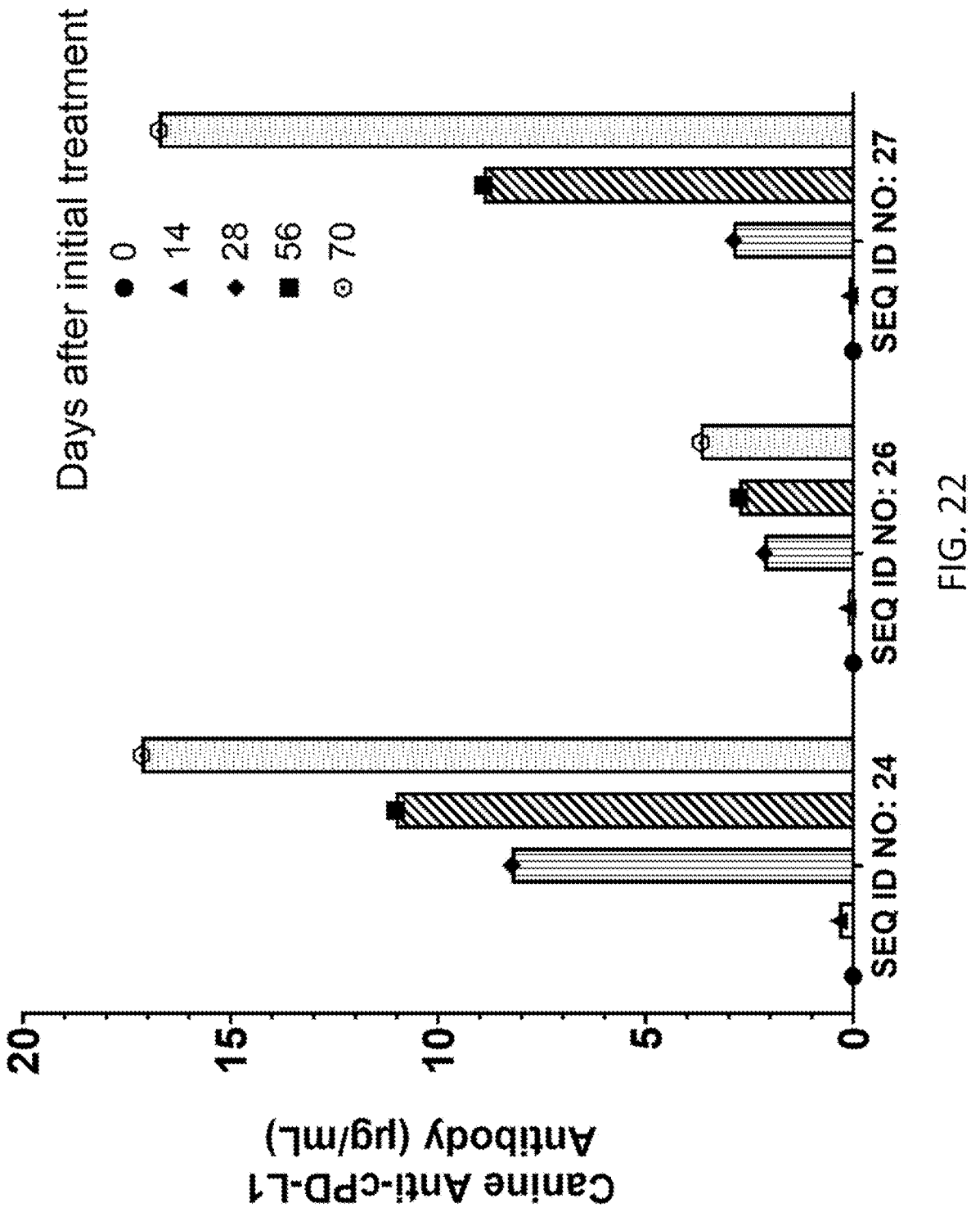
FIG. 22 is a graph showing canine anti-cPD-L1 antibody titer values detected (μg/mL) when the PD-L1 fusion proteins of SEQ ID NO: 24, SEQ ID NO: 26 and SEQ ID NO: 27 were administered to dogs on Days 0, 14, 28 and 56 according to Example 13.

FIG. 22 shows canine anti-cPD-L1 antibody titer values detected (μg/mL) when the PD-L1 fusion proteins of SEQ ID NO: 24, SEQ ID NO: 26 and SEQ ID NO: 27 were administered to dogs on Days 1, 14, 28 and 56 according to Example 13.

Figure 23:
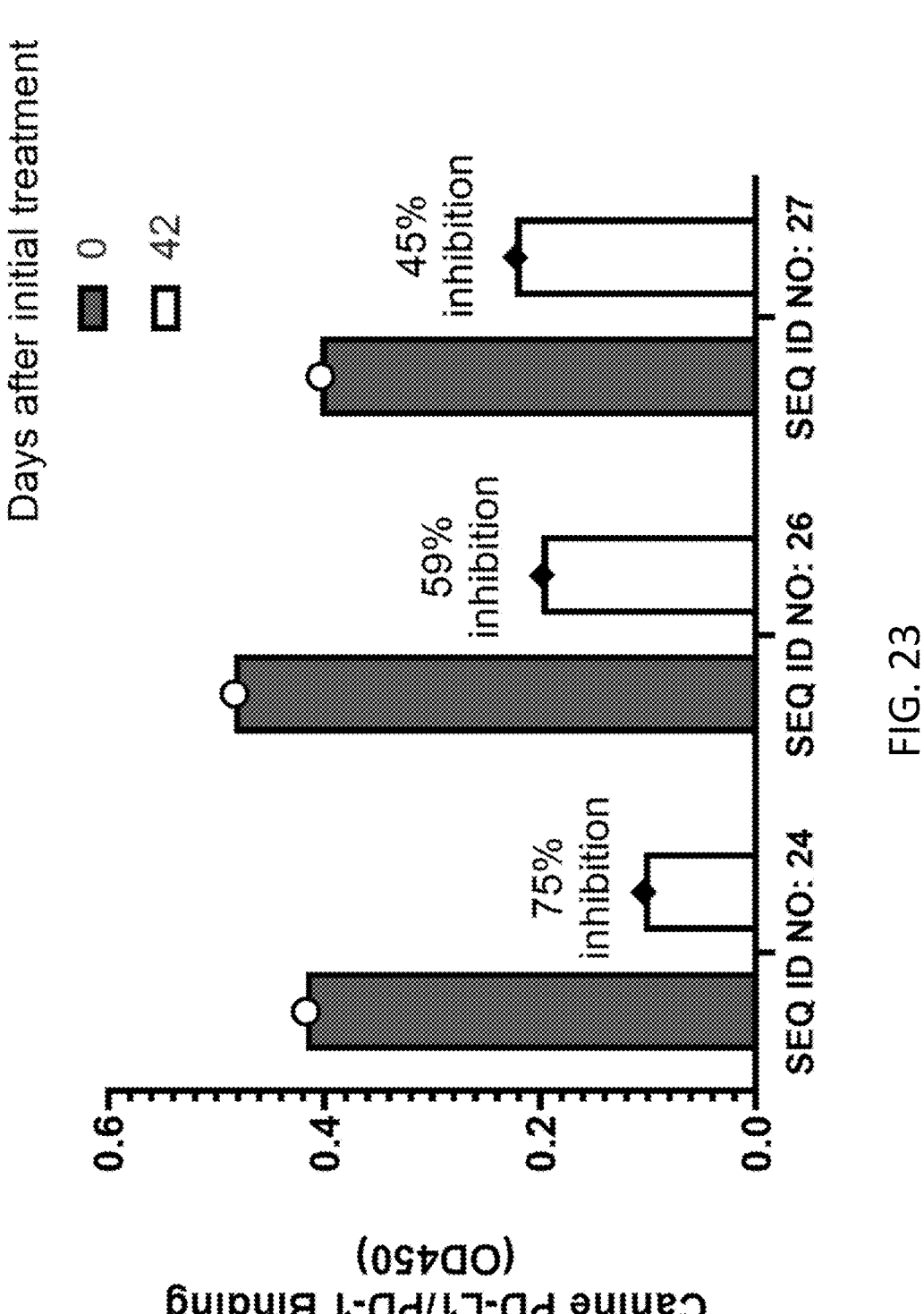
FIG. 23 is a graph showing canine PD-L1/PD-1 binding detected 0 and 42 days after the initial treatment, according to Example 15, when the PD-L1 fusion proteins of SEQ ID NO: 24, SEQ ID NO: 26 and SEQ ID NO: 27 were administered to dogs on Days 0, 14 and 28.

FIG. 23 shows canine PD-L1/PD-1 binding detected 0 and 42 days after the initial treatment, according to Example 15, when the PD-L1 fusion proteins of SEQ ID NO: 24, SEQ ID NO: 26 and SEQ ID NO: 27 were administered to dogs on Days 1, 14 and 28.

TABLE 1

Manufacturing Titers of PD-L1-analog Fc Fusion Proteins

| SEQ ID NO: | Calc. MW, Without Glycan (Da) | Volume Scale (L) | Yield (mg) | Titer (mg/L) |
|---|---|---|---|---|
| SEQ ID NO: 15 | 100988.2 | 0.10 | 0.25 | 3 |
| SEQ ID NO: 16 | 82959.5 | 0.10 | 1.80 | 18 |
| SEQ ID NO: 17 | 82827.9 | 0.10 | 3.46 | 35 |
| SEQ ID NO: 18 | 60710.5 | 0.10 | 0.95 | 10 |
| SEQ ID NO: 19 | 100547.7 | 0.10 | 1.52 | 15 |
| SEQ ID NO: 20 | 82617.8 | 0.10 | 14.96 | 150 |
| SEQ ID NO: 21 | 60440.1 | 0.10 | 14.76 | 148 |
| SEQ ID NO: 22 | 81590.9 | 0.10 | 22.02 | 220 |
| SEQ ID NO: 24 | 82342.5 | 0.10 | 19.7 | 197 |
| SEQ ID NO: 26 | 103493.3 | 0.10 | 40.72 | 407 |
| SEQ ID NO: 27 | 104520.2 | 0.10 | 37.87 | 379 |
| SEQ ID NO: 28 | 104508.3 | 0.10 | 6.95 | 70 |
| SEQ ID NO: 32 | 104412.1 | 0.10 | 17.31 | 173 |

PD-L1 Analog-Fc Fusion Proteins for Use as a Therapeutic Vaccine

Figure 14:
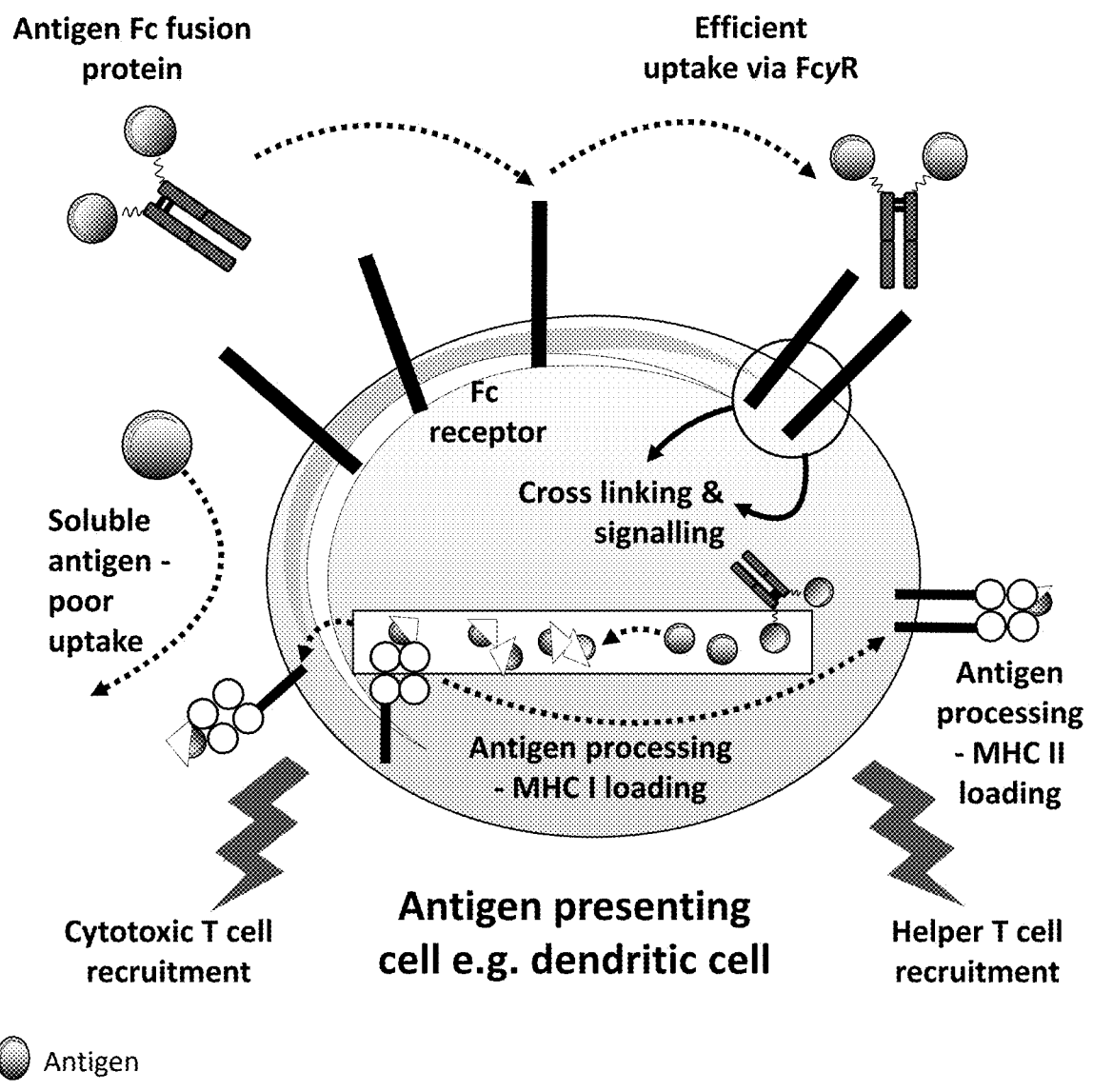
FIG. 14 is a schematic diagram depicting example modes in which an antigen or an antigen-Fc fusion protein may interact with an antigen presenting cell, e.g., a dendritic cell.

A PD-L1 analog-Fc fusion protein may be used as a vaccine. In one or more embodiments, the PD-L1 analog-Fc fusion protein is provided in a pharmaceutical composition. Injection of any protein into a patient (e.g., a dog) may induce an immune response, the magnitude and type of which is highly dependent on the "status" of the respective immune system. For example, injection of an antigen (Ag) that is foreign relative to a self Ag may induce a greater immune response in an immune system that maintains central and peripheral tolerance mechanisms. Moreover, foreign Ag administration to an immune system that has been primed to previous exposure to the respective Ag (e.g., a viral infection) will lodge a more rapid and elevated immune response relative to that of an Ag-naïve system. The immunological basis of this priming is two-fold: 1) an Ag-naïve immune system has naïve B and T lymphocytes that have a much higher threshold of activation than do the Ag-primed "memory" cells of a Ag-primed immune system, such that the antigen-presenting cells (APCs) that present Ag require much less Ag to activate primed memory T cells, and 2) due to expansion of memory T cells during the Ag priming exposure, there are inherently greater numbers of such cells upon re-exposure to an injected Ag. Note that dominant APCs are dendritic cells (DCs) and macrophages that present Ag in complex with Major Histocompatibility Complex (MHC) molecules on their surface to T cell Ag receptors. FIG. 14 is a schematic diagram depicting example modes in which an antigen may interact with an antigen presenting cell, e.g., a dendritic cell.

In another example, injection of a self Ag (or self Ag-Fc fusion protein) is designed to induce an immune response against a self Ag (e.g., a patient's endogenously-produced antigen or endogenously-produced protein, e.g., endogenously-produced PD-L1), but needs to overcome immune system central and peripheral tolerance mechanisms. To do so, the antigen is exposed to the immune system to cause an immune response (e.g., generate antibodies against the self Ag) in a manner that overcomes these tolerance mechanisms. In one embodiment, this is done through the use of a carrier (e.g., an adjuvant). In another embodiment, this can be done through linking of the self Ag or a self Ag analog to an Fc fragment in order to increase the antigen presentation of the self Ag via Fc fragment-Fc (gamma) R binding as depicted in FIG. 8. In another embodiment, this is done through linking of the self Ag or self Ag analog to an Fc fragment and using a carrier (e.g., an adjuvant).

Generation of an immune response against a self Ag may be done through a priming approach. The immunological basis of this priming is two-fold: 1) an Ag-naïve immune system has naïve B and T lymphocytes that have a much higher threshold of activation than do the Ag-primed "memory" cells of a Ag-primed immune system, such that the antigen-presenting cells (APCs) that present Ag require much less Ag to activate primed memory T cells, and 2) due to expansion of memory T cells during the Ag priming exposure, there are inherently greater numbers of such cells upon re-exposure to an injected self Ag or self Ag analog. Note that dominant APCs are dendritic cells (DCs) and macrophages that present Ag in complex with Major Histocompatibility Complex (MHC) molecules on their surface to T cell Ag receptors. FIG. 14 is a schematic diagram depicting example modes in which an antigen may interact with a presenting cell, e.g., a dendritic cell.

Further enhancement of an immune response against a self Ag may be done through a boosting approach. The immunological basis of this boosting is to allow for an expansion of memory T cells during the Ag priming exposure, so as to enhance the numbers of such cells upon re-exposure to an injected self Ag or self Ag analog. Boosting can be done through one or more follow-on injections after a priming injection. Boosting (e.g., booster injections) may contain a carrier (e.g., an adjuvant) or no carrier (no adjuvant). Boosting may increase the level of antibodies against a self Ag, create higher affinity antibodies against a self Ag, or both increase the level and the affinity of antibodies against a self Ag.

Antigen presenting cells (APCs) can influence both the "magnitude" and "type" of response to an Ag. B cells participate in the immune response directly by humoral immunity (antibody production) and also participate in the T cell immune response as specific APCs that selectively capture and present antigens to T cells. Both of these B cell functions are achieved through activation of the surface B cell receptor (BCR), which is essentially a membrane bound antibody that binds specifically to a particular antigen. Multivalent soluble antigens such as the Fc-fusion homodimer containing the specific antigen can be recognized by BCRs and activate them. Thus, the PD-L1 analog-Fc fusion protein homodimers can i) activate B cells through antigen-specific BCR activation leading to an increase in antibody production, and ii) through B cell mediated APC activity, increase T cell recognition and reactivity directed specifically against the PD-L1 epitopes. Thus, these fusion proteins can activate either humoral immunity, cellular immunity, or a combination of humoral and cellular immunity after administration.

Adjuvants

In some examples, APC activation is the conceptual basis of many immune enhancing substances called adjuvants. Dominant APCs are dendritic cells (DCs) and macrophages that present Ag in complex with Major Histocompatibility Complex (MHC) molecules on their surface to T cell Ag receptors. Some adjuvants are designed to trick the immune system into reacting to the injected Ag as if it were part of an ongoing infection (i.e., infectious agents provide such natural viral or bacterial adjuvant substances). Therefore, adjuvants activate APCs for greater Ag-presentation capabilities necessary to overcome the high activation threshold of naïve T cells, in addition to shaping their development into the Th1 immune system response, Th2 immune system response or a mixture of Th1 and Th2 immune system responses. Some T cells provide critical help to B cells that specifically bind the respective Ag to produce Ag-specific antibody (Ab) titers.

The novel PD-L1 analog-Fc fusion protein used as a vaccine may be co-administered with an adjuvant to enhance or otherwise alter the immune response in the target patient. In examples, known adjuvants may be used in a pharmaceutical composition of the PD-L1 analog-Fc fusion protein to enhance the induction of anti-PD-L1 antibodies.

Examples of adjuvants that may be employed in the pharmaceutical compositions disclosed herein include but are not limited to oil-in-water, amorphous aluminum hydroxyphosphate sulfate (AAHS), aluminum hydroxide, aluminum phosphate, potassium aluminum sulfate (Alum), Freund's adjuvant (complete and/or incomplete), squalene, AS02, AS03, AS04, MF59, AS01B, QS-21, CpG 1018, ISCOMS, Montanide™ ISA-51, Montanide™ ISA-720, Montanide™ GEL 01 PR, Montanide™ GEL 02 PR, Sepivac SWE, Quil-A™, polylactide co-glycolide (PLG), monophosphoryl lipid A (MPL), Detox, AGP [RC-529],DC_Chol, OM-174 (lipid A derivative), CpG motifs (synthetic oligonucleotides containing immunostimulatory CpG motifs), modified LT and CT, hGM-CSF, hIL-12, Immudaptin, inert vehicles, such as gold particles as well as various experimental adjuvants from sources such as Advax (Australia) such as AddaVax (Invivogen) or other Advax-based vaccine adjuvants.

In some examples, the selected adjuvant may be MF59 (Novartis) and AS-03 (GlaxoSmithKline). A custom formulation of MF59 (Novartis) or an equivalent such as AddaVax (Invivogen) or other Advax-based vaccine adjuvants from Vaxine Pvt Ltd. (Australia) may be used in a pharmaceutical composition of the PD-L1 analog-Fc fusion protein. In examples, the PD-L1 analog-Fc fusion protein is co-administered with the Montanide™ ISA-720 adjuvant to enhance or otherwise alter the immune response in the target patient. In examples, the PD-L1 analog-Fc fusion protein is co-administered with the Quil-™ adjuvant to enhance or otherwise alter the immune response in the target patient.

In one or more embodiments, the PD-L1 analog-Fc fusion protein formulation is prepared onsite for administration. In one aspect, the PD-L1 analog-Fc fusion protein is mixed with an adjuvant onsite under sterile mixing conditions. In one aspect, the PD-L1 analog-Fc fusion protein and adjuvant are thoroughly mixed and/or emulsified to prepare a homogenous emulsion for administration to the patient. In one or more embodiments, the prepared emulsification is refrigerated (4° C.) or room temperature stable for at least 8 hours, preferably up to 24 hours, preferably up to 48 hours or more. The adjuvanted formulation of the PD-L1 analog-Fc fusion protein or a pharmaceutical composition thereof is administered to a patient by subcutaneous (s.c.) injection or intramuscular (i.m.) injection, as the s.c. or i.m. injection sites are more likely to induce a strong antibody response due to there being more dendritic cells (DCs) in the subcutaneous and intramuscular spaces. In examples, the composition is adapted for therapeutic vaccination.

As described above, in some cases, it may be advantageous to use an adjuvant in the pharmaceutical composition in order to increase the quantity of anti-PD-L1 antibody titers as measured according to Example 9. The use of an adjuvant may be especially advantageous in older patients who experience altered immune competence with increasing age, so-called immunosenescence, which is the result of changes at multiple levels of the immune system over time. Once a patient has measurable antibodies, upon re-challenge with PD-L1 or a PD-L1 analog-Fc fusion protein, the patient will exhibit rapid development of anti-PD-L1 antibodies.

Primary PD-L1 Analog-Fc Fusion Protein Vaccines Evaluated in Mice

The efficacy of an exemplary PD-L1 analog-Fc fusion proteins of this disclosure or pharmaceutical compositions thereof may be initially evaluated in mice immunization studies for their capacity to induce anti-PD-L1 protein IgG titers when administered according to the procedure in Example 10. BALB/c mice are a relevant animal model that has been extensively used for preclinical immunogenicity assessment of vaccines. This strain generates robust antibody (Ab) responses when immunized with adjuvanted and non-adjuvanted vaccine candidates. Moreover, mouse-specific reagents are widely available for evaluating the kinetics and characteristics of a variety of immune responses to vaccination, including relevant Ab isotypes and T cell responses (e.g., Th1 vs. Th2 responses). Therefore, the BALB/c mouse model is selected to evaluate the immunogenicity of PD-L1 analog-Fc fusion protein vaccines with respect to dose, potentiation by adjuvants, routes of administration, and dosing frequency required to achieve optimal Ab responses.

Briefly, target mice (e.g., BALB/c mice) were injected three times at predetermined intervals (e.g., on Day 0, Day 21, and Day 42) with an exemplary PD-L1 analog-Fc fusion protein (with or without Montanide™ ISA 720 adjuvant) or pharmaceutical composition thereof, and serum is collected at regular intervals (e.g., every 7-14 days beginning at Day 14). After administering one or more than one treatment of the PD-L1 analog-Fc fusion protein of SEQ ID NO: 24, SEQ ID NO: 26, SEQ ID NO: 27, SEQ ID NO: 28 or SEQ ID NO: 32 to N=5 BALB/c mice according to Example 10, anti-PD-L1 IgG antibody titers were measured according to Example 9.

As previously discussed, adjuvants activate APCs for greater Ag-processing and Ag-presentation capabilities which are necessary to overcome the high activation threshold of naïve T cells. It is expected that when the PD-L1 analog-Fc fusion protein of SEQ ID NO: 24, SEQ ID NO: 26, SEQ ID NO: 27, SEQ ID NO: 28 or SEQ ID NO: 32 is combined with Montanide™ ISA 720 adjuvant (30%/70% v/v), Sepivac SWE™ adjuvant (50%/50% v/v) or Quil-A™ adjuvant (15 µg per dose), the anti-PD-L1 protein antibody titers at approximately 35 days after the first injection on Day 0 will be greater compared to the PD-L1 analog-Fc fusion protein without adjuvant.

The kinetic response, which is the duration of response, to dose levels varying from 1 µg to 100 µg after 1, 2, and 3 doses is expected to demonstrate increasing anti-PD-L1 protein antibody titers at all dose levels up to at least 56 days post vaccination.

PD-L1 Analog-Fc Fusion Proteins for Use as a Booster Vaccine

In examples, an exemplary PD-L1 analog-Fc fusion protein of this disclosure, for example the PD-L1 analog-Fc fusion protein of SEQ ID NO: 24, SEQ ID NO: 26, SEQ ID NO: 27, SEQ ID NO: 28 or SEQ ID NO: 32, may be used as a booster vaccine. Administration of the PD-L1 analog-Fc fusion protein to patients that already have low but measurable antibody levels to the PD-L1 self-antigen (e.g., after a primary vaccination with a PD-L1-analog Fc fusion protein) to amplify their antibody titers and increase their neutralization against the endogenously produced PD-L1. PD-L1 analogs are synthesized to maximize antigenicity and overall manufacturability, while the Fc region prolongs antigen residence time and/or binding to Fc (gamma) R receptors present on APCs. Without wishing to be bound to any particular theory of mechanism, it is believed that during the longer in vivo residence time, the naturally glycosylated Fc fragment will help bind Fc (gamma) receptors on antigen-presenting cells (APCs), which will in turn cause greater presentation of the PD-L1 analog antigen to T-cells and/or B-cells, which is expected to produce a strong immune response (e.g., antibody titers) to the PD-L1 antigen present on the PD-L1 analog-Fc fusion protein, and that these antibody titers will be able to bind and neutralize the endogenously produced target protein (e.g., PD-L1). Specifically, the APCs internalize the PD-L1 antigen via Fc (gamma) receptors, and then process and present PD-L1 fragments to CD4+ Th cells that in turn promote ("help") B cell activation and anti-PD-L1 IgG (i.e., Ab) production.

Antigen-presenting cells may be, for example, dendritic cells (DCs), monocytes or macrophages that can internalize the molecules of the PD-L1 analog-Fc fusion protein of SEQ ID NO: 24, SEQ ID NO: 26, SEQ ID NO: 27, SEQ ID NO: 28 or SEQ ID NO: 32 via Fc-receptor mediated phagocytosis (e.g., through the Fc region of the PD-L1 analog-Fc fusion protein binding to the Fc (gamma) receptors in immune cells). Fc-mediated uptake of the PD-L1 analog-Fc fusion protein by, for example, a subset of DCs (e.g., $cDC_{2S}$) promotes the development of anti-PD-L1 T helper 2 (Th2) cells through secretion of IL-10 and IL-33. Anti-PD-L1 Th2 cells activate anti-PD-L1 B-cells, for example by cross linking their antigen receptors to allow the B-cells to attract the Th2 cells. B-cell antigen receptor (BCR) mediated uptake binds the PD-L1 of the PD-L1 analog-Fc fusion protein molecules, then delivers the PD-L1 antigen to intracellular sites where it is degraded and returned to the B-cell surface as peptides bound to MHC class II molecules. The peptide MCH class II complex can be recognized by the PD-L1-specific helper T cells simulating them to make proteins that in turn cause the B-cell to proliferate and its progeny to differentiate into B cells that secrete anti-PD-L1 antibodies. The PD-L1 analog-Fc fusion protein of SEQ ID NO: 24, SEQ ID NO: 26, SEQ ID NO: 27, SEQ ID NO: 28 or SEQ ID NO: 32 may increase exposure of the PD-L1 analog fragment to antigen producing cells over a protracted period of time due to the presence of the Fc fragment and the Fc-FcRn receptor interactions that enable the PD-L1 analog-Fc fusion protein to have a prolonged in vivo pharmacokinetic half-life as compared to the PD-L1 analog alone without the linker or Fc sequence. Furthermore, and as previously described, the glycosylated Fc fragment in the PD-L1 analog-Fc fusion protein of SEQ ID NO: 24, SEQ ID NO: 26, SEQ ID NO: 27, SEQ ID NO: 28 or SEQ ID NO: 32 is expected to help induce a strong immune response directed to the therapeutic or antigen portion of the fusion protein through binding of the Fc to Fc (gamma) R receptors on immune cells, thereby increasing PD-L1-analog uptake and processing in a manner described in FIG. 8. These properties in combination are expected to significantly increase the amount of anti-PD-L1 antibodies while also decreasing the amount of antigen necessary to produce the required immune response.

In examples, a therapy comprising treatment of a patient with the PD-L analog-Fc fusion protein of SEQ ID NO: 24, SEQ ID NO: 26, SEQ ID NO: 27, SEQ ID NO: 28, SEQ ID NO: 32, or a pharmaceutical composition thereof, may consist of a booster vaccine administered to patients that are already antibody-positive to PD-L1 (e.g., patients that may already have received an initial dose of PD-L1 analog-Fc fusion protein vaccine), as a means to amplify their antibody titers and affinity. Furthermore, a therapy comprising a treatment of a patient with the PD-L1 analog-Fc fusion protein of SEQ ID NO: 24, SEQ ID NO: 26, SEQ ID NO: 27, SEQ ID NO: 28, SEQ ID NO: 32, or a pharmaceutical composition thereof, may be administered as a booster vaccine to patients that have been previously immunized with a vaccine against PD-L1 as a means to amplify their antibody titers and affinity specifically against PD-L1. Such a therapy is important in cases where priming vaccines are not 100% effective and/or where the induced antibody titers wane over time. In examples, the PD-L1 analog-Fc fusion protein of SEQ ID NO: 24, SEQ ID NO: 26, SEQ ID NO: 27, SEQ ID NO: 28, SEQ ID NO: 32, or a pharmaceutical composition thereof may be administered to a patient by subcutaneous injection (s.c.) or intramuscularly (i.m.), as the s.c. or i.m. injection sites are more likely to induce a strong antibody response due to there being more dendritic cells (DCs) in the subcutaneous and intramuscular spaces.

Fc Fusion Protein Production

In embodiments, a fusion protein can be expressed by a cell as described in more detail in the Examples section.

Expression and Purification

A PD-L1 analog-Fc fusion protein can be expressed recombinantly, e.g., in a eukaryotic cell, e.g., mammalian cell or non-mammalian cell. Exemplary mammalian cells used for expression include CHO cells or HEK293 cells. CHO cells can be subdivided into various strains or subclasses, (e.g., CHO DG44, CHO-M, CHO-SE™ and CHO-K1), and some of these cell strains may be genetically engineered for optimal use with a particular type of nucleic acid molecule (e.g., a vector comprising DNA) or a particular cell growth media composition as described in the Examples section. Cells may be transfected with a nucleic acid molecule (e.g., vector) encoding the PD-L1 analog-Fc fusion protein (e.g., where the entire PD-L1 analog-Fc fusion protein is encoded by a single nucleic acid molecule). CHO cells may be transfected with a vector that encodes for the PD-L1 analog-Fc fusion protein, but this process only results in temporary expression of the PD-L1 analog-Fc fusion protein for a period of time (e.g., 3 days, 4 days, 5, days, 7 days, 10 days, 12 days, 14 days, or more) before the host cell stops expressing appreciable levels of the PD-L1 analog-Fc fusion protein (i.e., transient transfection). CHO cells that are transiently transfected with nucleic acid sequences encoding for PD-L1 analog-Fc fusion proteins often allow for more rapid production of recombinant proteins which facilitates making and screening multiple PD-L1 analog-Fc fusion protein candidates. CHO cells may be transfected with a vector that is permanently incorporated into the host cell DNA and leads to consistent and permanent expression (i.e., stable transfection) of the PD-L1 analog-Fc fusion protein as long as the cells are cultured appropriately. CHO cells and CHO cell lines that are stably transfected with nucleic acids encoding for PD-L1 analog-Fc fusion proteins often take longer to develop, but they often produce higher protein yields and are more amenable to manufacturing low-cost products (e.g., products for use in the veterinary pharmaceutical market). Cells and cell lines can be cultured using standard methods known in the art. Synthesis and methods of making a PD-L1 analog-Fc fusion protein in transiently transfected CHO cells is described in Example 1, and synthesis and methods of making a PD-L1 analog-Fc fusion protein in stably transfected CHO cells is described in Example 2.

In examples, the PD-L1 analog-Fc fusion protein may be purified or isolated from the cells (e.g., by lysis of the cells). The PD-L1 analog-Fc fusion protein is secreted by the cells and may be purified or isolated from the cell culture media in which the cells were grown. Purification of the PD-L1 analog-Fc fusion protein can include using column chromatography (e.g., affinity chromatography) or using other separation methods based on differences in size, charge, and/or affinity for certain molecules. Purification of the PD-L1 analog-Fc fusion protein involves selecting or enriching for proteins containing an Fc fragment, e.g., by using Protein A beads or a Protein A column that cause proteins containing an Fc fragment to become bound with affinity at neutral solution pH to the Protein A covalently conjugated to the Protein A beads. The bound PD-L1 analog-Fc fusion protein may then be eluted from the Protein A beads by a change in a solution variable (e.g., a decrease in the solution pH). Other separation methods such as ion exchange chromatography and/or gel filtration chromatography can also be employed alternatively or additionally. Purification of the PD-L1 analog-Fc fusion protein may further comprise filtering or centrifuging the protein preparation, diafiltration, ultrafiltration, and filtration through porous membranes of various sizes, as well as final formulation with excipients. Purification of a PD-L1 analog-Fc fusion protein is described in Example 3.

The purified PD-L1 analog-Fc fusion protein can be characterized, e.g., for purity, protein yield, structure, and/or activity, using a variety of methods, e.g., absorbance at 280 nm (e.g., to determine protein yield), size exclusion or capillary electrophoresis (e.g., to determine the molecular weight, percent aggregation, and/or purity), mass spectrometry (MS) and/or liquid chromatography (LC-MS) (e.g., to determine purity and/or glycosylation), and/or ELISA (e.g., to determine extent of binding, e.g., affinity, to a PD-L1 antibody or a PD-1 cell receptor). Exemplary methods of characterization are also described in Example 6 and Example 7.

The protein yield of a PD-L1 analog-Fc fusion protein after production in transiently transfected CHO cells and protein A purification may be greater than 50 mg/L (e.g., greater than 60 mg/L, greater than 70 mg/L, greater than 80 mg/L, greater than 90 mg/L, preferably greater than 100 mg/L).

Pharmaceutical Compositions and Routes of Administration

The amount and concentration of the PD-L1 analog-Fc fusion protein in the pharmaceutical compositions, as well as the quantity of the pharmaceutical composition administered to a patient, can be selected based on clinically relevant factors, such as medically relevant characteristics of the patient (e.g., age, weight, gender, other medical conditions, and the like), the solubility of compounds in the pharmaceutical compositions, the potency and activity of the compounds, and the manner of administration of the pharmaceutical compositions.

Formulations of the present disclosure include those suitable for parenteral administration. The phrases "parenteral administration" and "administered parenterally" as used herein means modes of administration other than enteral and topical administration, usually by intravenous, intramuscular, or subcutaneous injection.

Examples of suitable aqueous and non-aqueous carriers that may be employed in the pharmaceutical compositions of the disclosure include water, saline, ethanol, salts, polyols (such as glycerol, propylene glycol, polyethylene glycol, and the like), and suitable mixtures thereof, vegetable oils, such as olive oil, and injectable organic esters, such as ethyl oleate, buffering agents, such as potassium and/or sodium phosphates, pH buffers, such as hydrochloric acid and/or sodium hydroxide, and the like. Proper fluidity can be maintained, for example, by the use of coating or emulsifier materials, such as lecithin, by the maintenance of the required particle size in the case of dispersions, and by the use of surfactants, e.g., Tween-like surfactants. In some examples, the pharmaceutical composition (e.g., as described herein) comprises a Tween-like surfactant, e.g., polysorbate-20, Tween-20, or Tween-80. In some examples, the pharmaceutical composition (e.g., as described herein) comprises a Tween-like surfactant, e.g., Tween-80, at a concentration between about 0.001% and about 2%, or between about 0.005% and about 0.1%, or between about 0.01% and about 0.5%. Other examples of suitable carriers that may be employed in the pharmaceutical compositions of the disclosure include adjuvants such as Montanide™ ISA 720, Quil-A™ and Sepivac SWE™.

Further examples of suitable carriers may include carriers that act as preservatives (e.g., carrier additives added to prevent the growth of adventitious agents that may be present or introduced into a pharmaceutical composition). Non-limiting exemplary preservatives include meta-cresol, methyl paraben, propyl paraben, benzyl alcohol, sodium benzoate, phenoxyethanol, and potassium sorbate.

The PD-L1 analog-Fc fusion protein may be administered as a bolus, infusion, or an intravenous push, or administered through syringe injection, pump, pen, needle, or indwelling catheter. The PD-L1 analog-Fc fusion protein may be administered by a subcutaneous bolus injection. In examples, the PD-L1 analog-Fc fusion protein or a pharmaceutical composition thereof is administered to a patient by subcutaneous injection (s.c.) or intramuscularly (i.m.), as the s.c. or i.m. injection sites are more likely to induce a strong antibody response due to there being more dendritic cells (DCs) in the subcutaneous and intramuscular spaces. Methods of introduction may also be provided by rechargeable or biodegradable devices. Various slow-release polymeric devices have been developed and tested in vivo in recent years for the controlled delivery of drugs, including proteinaceous biopharmaceuticals. A variety of biocompatible polymers (including hydrogels), including both biodegradable and non-degradable polymers, can be used to form an implant for the sustained release of a compound at a particular target site. Additional pharmaceutically acceptable ingredients for use in the compositions include buffering agents, salts, stabilizing agents, diluents, preservatives, antibiotics, isotonic agents, and the like.

Dosages

In use, a therapeutically effective amount of the PD-L1 analog-Fc fusion protein is administered to a patient in need thereof. Administration of the PD-L1 analog-Fc fusion protein elicits an immune response in the patient, and more specifically an immune response against PD-L1, resulting in the treatment of cancers, tumors or other diseases associated with expression of the PD-L1 protein in dogs. The immune response is demonstrated by a lack of observable clinical symptoms, or reduction of clinical symptoms normally displayed by an afflicted patient. In another embodiment, a method of activating an immune cell at a site of infection or disease is provided comprising administering a therapeutically effective amount of the PD-L1 analog-Fc fusion protein to a patient. In another aspect, a method of increasing antibody production in a patient is provided comprising administering a therapeutically effective amount of the PD-L1 analog-Fc fusion protein to a patient.

Actual dosage levels of the PD-L1 analog-Fc fusion protein can be varied so as to obtain an amount of the active ingredient that is effective to achieve the desired therapeutic response for a particular patient. The selected dosage level will depend upon a variety of factors including the activity of the particular fusion protein employed, or the ester, salt or amide thereof, the route of administration, the time of administration, the rate of excretion of the particular compound being employed, the duration of the treatment, other drugs, compounds and/or materials used in combination with the particular fusion protein employed, the age, sex, weight, condition, general health and prior medical history of the patient being treated, and like factors well known in the medical arts. In general, a suitable dose of a PD-L1 analog-Fc fusion protein will be the amount that is the lowest dose effective to produce a therapeutic effect. Such an effective dose will generally depend upon the factors described above.

The immunogenic formulation is provided, in various aspects, in unit dosage form for case of administration and uniformity of dosage. "Unit dosage form" as used herein refers to physically discrete units suited as unitary dosages for the patient to be treated, each unit containing a predetermined quantity of the PD-L1 analog-Fc fusion protein calculated to produce the desired therapeutic effect in association with the required pharmaceutical carrier. The specification for the dosage unit forms is dictated by and are directly dependent on the unique characteristics of the excipient(s) and therapeutic agent(s) and the particular biological effect to be achieved. In one or more embodiments, the formulation is provided in a kit of components for administration of the PD-L1 analog-Fc fusion protein to the patient. In one or more embodiments, a pharmaceutical composition comprising the PD-L1 analog-Fc fusion protein dispersed in a suitable carrier is provided in a unit dosage form (e.g., vial). In one or more embodiments, the kit further comprises a discrete unit dosage form (e.g., vial) containing an adjuvant and/or other carrier system for onsite mixing of the PD-L1 analog-Fc fusion protein for administration. In one or more embodiments, the kit comprises one or more emulsifying needles and syringes for onsite mixing of the immunogenic formulation for administration. In one or more embodiments, the kit comprises one or more dosing syringes for administering the prepared immunological composition to the patient. In one or more embodiments, the kit further comprises instructions for preparing the immunogenic composition and/or administering the immunogenic composition.

The present disclosure contemplates formulation of a PD-L1 analog-Fc fusion protein in any of the aforementioned pharmaceutical compositions and preparations. Furthermore, the present disclosure contemplates administration via any of the foregoing routes of administration. One of skill in the art can select the appropriate formulation, dose level and route of administration based on the condition being treated and the overall health, age, and size of the patient being treated.

EXAMPLES

The present technology is further illustrated by the following Examples. It is to be understood, however, that these examples are provided by way of illustration, and nothing therein should be taken as a limitation upon the overall scope of the technology.

General Examples for Synthesis, Purification and Validation of PD-L1 Analog-Fc Fusion Proteins

Example 1: Synthesis and Methods of Making a PD-L1 Analog-Fc Fusion Protein in Transiently Transfected CHO Cells PD-L1 analog-Fc fusion proteins were synthesized as follows. A gene sequence of interest was constructed using proprietary software (Curia, Belmont, CA) and was cloned into a high expression mammalian vector. CHO cells were seeded in a shake flask 24 hours before transfection and were grown using serum-free chemically defined media. A DNA expression construct that encodes the PD-L1 analog-Fc fusion protein of interest was transiently transfected into a suspension of CHO cells using the (Curia, Belmont, CA) standard operating procedure for transient transfection. After 20 hours, the cells were counted to determine the viability and viable cell count, and the titer was measured by FortéBio® Octet® (Pall FortéBio LLC, Fremont, CA). Additional readings were taken throughout the transient transfection production run. The culture was harvested on or after Day 14.

Example 2: Synthesis and Methods of Making a PD-L1 Analog-Fc Fusion Protein in CHO Cells A CHO cell line is originally derived from CHO-K1 (Curia, Belmont, CA), and the endogenous glutamine synthetase (GS) genes are knocked out by recombinant technology using methods known in the art. Stable expression DNA vectors are designed and optimized for CHO expression and GS selection and incorporated into a high expression mammalian vector (Curia, Belmont, CA). The sequence of each completed construct is confirmed prior to initiating scale up experiments. The suspension-adapted CHO cells are cultured in a humidified 5% CO2 incubator at 37° C. in a chemically defined media (CD OptiCHO; Invitrogen, Carlsbad, CA). No serum or other animal-derived products are used in culturing the CHO cells.

Approximately 80 million suspension-adapted CHO cells, growing in CD OptiCHO media during the exponential growth phase, are transfected by electroporation using MaxCyte® STX® system (MaxCyte, Inc., Gaithersburg, MD) with 80 µg DNA to create a stable CHO cell line for each PD-L1 analog-Fc fusion protein (DNA construct contains the full-length sequence of the PD-L1 analog-Fc fusion protein). After twenty-four hours, the transfected cells are counted and placed under selection for stable integration of the PD-L1 analog-Fc fusion genes. The transfected cells are seeded into CD OptiCHO selection media containing between 0-100 µM methionine sulfoximine (MSX) at a cell density of $0.5\times10^6$ cells/mL in a shaker flask and incubated at 37° C. with 5% CO2. During a selection process, the cells are spun down and resuspended in fresh selection media every 2-3 days until the CHO stable pool recovered its growth rate and viability. The cell culture is monitored for growth and titer.

The cells are grown to $2.5\times10^6$ cells per mL. At the time of harvest for cell banking, the viability is expected to be above 95%. The cells are then centrifuged, and the cell pellet is resuspended in the CD OptiCHO media with 7.5% dimethyl sulfoxide (DMSO) to a cell count of $15\times10^6$ cells per mL per vial. Vials are cryopreserved for storage in liquid nitrogen.

A small-scale-up production is performed using the CHO cells as follows. The cells are scaled up for production in CD OptiCHO growth medium containing up to 100 µM MSX at 37° C. and fed every 2-4 days as needed, with CD OptiCHO growth medium supplemented with glucose and additional amino acids as necessary for approximately 14-21 days. The MSX concentration is optionally increased over time to exert additional selectivity for clones capable of yielding higher product titers.

The conditioned media supernatant harvested from the stable pool production run is clarified by centrifuge spinning. The protein is run over a Protein A (MabSelect, Cytiva, Marlborough, MA) column pre-equilibrated with binding buffer. Washing buffer is then passed through the column until the OD280 value (NanoDrop, Thermo Scientific) is measured to be at or near background levels. The PD-L1 analog-Fc fusion protein is eluted using a low pH buffer, elution fractions are collected, and the OD280 value of each fraction is recorded. Fractions containing the target PD-L1 analog-Fc fusion protein are pooled and optionally further filtered using a 0.2 µm membrane filter.

The cell line is optionally further subcloned to monoclonality and optionally further selected for high titer PD-L1 analog-Fc-fusion protein-expressing clones using the method of limiting dilution, a method known to those skilled in the art. After obtaining a high titer, monoclonal PD-L1 analog-Fc fusion protein-expressing cell line, production of the PD-L1 analog-Fc fusion protein is accomplished as described above in growth medium without MSX, or optionally in growth medium containing MSX, to obtain a cell culture supernatant containing the recombinant, CHO-made, PD-L1 analog-Fc fusion protein.

Example 3: Purification of a PD-L1 Analog-Fc Fusion Protein Manufactured in CHO Cells Purification of a PD-L1 analog-Fc fusion protein was performed as follows. Conditioned media supernatants containing the secreted PD-L1 analog-Fc fusion protein were harvested from the CHO production runs and were clarified by centrifugation. The supernatant containing the desired PD-L1 analog-Fc fusion protein was run over a Protein A column, washed, and eluted using a low pH gradient. Afterwards, the eluted fractions containing the desired protein were pooled and buffer exchanged into 100 mM HEPES, 100 mM NaCl, 50 mM NaOAc, pH 6.0 buffer. A final filtration step was performed using a 0.2 µm membrane filter. The final protein concentration was calculated from the solution optical density at 280 nm. Further optional purification by ion-exchange chromatography (e.g., using an anion exchange bead resin or a cation exchange bead resin), gel filtration chromatography, or other methods were performed, as necessary.

Example 4: PD-L1 Analog-Fc Fusion Protein Structure Confirmation by Non-Reducing and Reducing SDS-PAGE A PD-L1 analog-Fc fusion protein sample for analysis is prepared in loading buffer (± reductant; e.g., beta-mercaptoethanol) and denatured at 70° C. for 10 min before being loaded into the NuPAGE™ Gel system (ThermoFisher Scientific). After electrophoresis, the gel is stained with SimplyBlue™ SafeStain. Under non-reducing conditions, the sample is run against known molecular weight (MW) protein standards, and the eluting peak represents the 'apparent' MW of the fusion protein homodimer.

Under reducing conditions (e.g., using beta-mercaptoethanol to break disulfide bonds of the PD-L1 analog-Fc fusion protein homodimer), the apparent MW of the resulting PD-L1 analog-Fc fusion protein monomer is compared against half the molecular weight of the PD-L1 analog-Fc fusion protein homodimer as a way of determining that the structural purity of the PD-L1 analog-Fc fusion protein is likely to be correct.

Example 5: PD-L1 Analog-Fc Fusion Protein Structure Confirmation by Non-Reducing and Reducing CE-SDS CE-SDS analysis was performed in a LabChip® GXII (Perkin Elmer, Waltham, MA) on a solution of a purified PD-L1-analog-Fc fusion protein dissolved in 200 mM HEPES, 100 mM NaCl, 50 mM NaOAc, pH 6.0 buffer, and the electropherogram was plotted. Under non-reducing conditions, the sample was run against known molecular weight (MW) protein standards, and the eluting peak represented the 'apparent' MW of the PD-L1-analog-Fc fusion protein homodimer.

Under reducing conditions (e.g., using beta-mercaptoethanol to break disulfide bonds of the PD-L1-analog-Fc fusion homodimer), the apparent MW of the resulting PD-L1-analog-Fc fusion protein monomer as defined by the peak with the largest peak area (e.g., meaning integrating the area under all peaks of the resulting chromatogram, but considering only the MW of the peak with the largest amount of area under the chromatogram trace for that peak) was compared against half the molecular weight of the PD-L1-analog-Fc fusion protein homodimer as a way of determining that the structural purity of the PD-L1-analog-Fc fusion protein was likely to be correct.

The non-reducing and reducing main peaks, as defined by the largest peak areas in their respective chromatograms, found via CE-SDS analysis for PD-L1-analog-Fc fusion proteins synthesized in CHO cells are shown in Table 2, and 2× the apparent MW of the resulting PD-L1-analog-Fc fusion protein monomer was compared to the molecular weight of the PD-L1-analog-Fc fusion protein homodimer. The results in Table 2 illustrate that the structural conformations of the PD-L1-analog-Fc fusion proteins are likely to be correct

TABLE 2

| | | Non-reducing Peak | Reducing Peak | |
| | Compound | | | |
| Sequence ID | Target MW (kDa)* | "Homodimer" MW (kDa) | "Monomer" MW (kDa) | $\dfrac{MW_{homodimer}}{2 \times MW_{monomer}}$ |
|---|---|---|---|---|
| SEQ ID NO: 20 | 82.62 | 141.28 | 80.60 | 0.88 |
| SEQ ID NO: 21 | 60.44 | 93.37 | 54.38 | 0.86 |
| SEQ ID NO: 22 | 81.59 | 137.34 | 79.43 | 0.86 |
| SEQ ID NO: 24 | 82.34 | 177.29 | 107.07 | 1.10 |
| SEQ ID NO: 26 | 103.49 | 189.27 | 113.62 | 0.83 |
| SEQ ID NO: 27 | 104.52 | 189.57 | 116.01 | 0.82 |
| SEQ ID NO: 28 | 104.51 | 181.93 | 112.32 | 0.81 |
| SEQ ID NO: 32 | 104.41 | 186.86 | 114.95 | 0.81 |

*Target MW is the predicted molecular weight assuming no glycosylation. As known to those experienced in the art, the actual observed MW of the homodimer and the monomer can differ due to post-translational modifications to the protein (e.g., such as addition of glycosylation at one or more sites on the protein during recombinant synthesis).

Example 6: PD-L1 Analog-Fc Fusion Protein Sequence Identification by LC-MS with Glycan Removal To obtain an accurate estimate of the PD-L1 analog-Fc fusion protein mass via mass spectroscopy (MS), the sample is first treated to remove naturally occurring glycan that might interfere with the MS analysis. 100 μL of a PD-L1 analog-Fc fusion protein dissolved in 100 mM HEPES, 100 mM NaCl, 50 mM NaOAc, pH 6.0 buffer solution is first buffer exchanged into 0.1 M Tris, pH 8.0 buffer containing 5 mM EDTA using a Zeba desalting column (Pierce, ThermoFisher Scientific, Waltham, MA). 3.33 μL of PNGase F enzyme (New England Biolabs Remove-iT® PNGase F) is added to this solution to remove N-linked glycan present in the fusion protein (e.g., glycan linked to the side chain of the asparagine located at the cNg-N site), and the mixture is incubated at 37° C. overnight in an incubator. The overnight incubated mixture is then buffer exchanged into Phosphate Buffered Saline. The sample is then analyzed via LC-MS (Novatia LLC, Newtown, PA) resulting in a molecular mass of the molecule which corresponds to the desired homodimer without the glycan. This mass is then further corrected since the enzymatic process used to cleave the glycan from the cNg-asparagine also deaminates the asparagine side chain to form an aspartic acid, and in doing so the enzymatically treated homodimer gains 2 Da overall, corresponding to a mass of 1 Da for each chain present in the homodimer. Therefore, the actual molecular mass is the measured mass minus 2 Da to correct for each of the enzymatic modifications of the PD-L1 analog-Fc fusion protein structure in the analytical sample.

Example 7: % Homodimer by Size-Exclusion Chromatography for a PD-L1 Analog-Fc Fusion Protein Size-exclusion chromatography (SEC-HPLC) of PD-L1 analog-Fc fusion proteins is carried out using a Waters 2795HT HPLC (Waters Corporation, Milford, MA) connected to a 2998 Photodiode array at a wavelength of 280 nm. 100 μL or less of a sample containing a PD-L1 analog-Fc fusion protein of interest is injected into an AdvanceBio SEC 300Å, 4.6×300 mm, 2.7 μm, LC column (Agilent Technologies, Santa Clara, CA) operating at a flow rate of 0.2 mL/min and with a mobile phase comprising 50 mM sodium phosphate, 300 mM NaCl, and 0.05% w/v sodium azide, pH 6.2. The AdvanceBio SEC column operates on the principle of molecular size separation. Therefore, larger soluble PD-L1 analog-Fc aggregates (e.g., multimers of PD-L1 analog-Fc fusion protein homodimers) elute at earlier retention times, and the non-aggregated homodimers elute at later retention times. In separating the mixture of homodimers from aggregated multimeric homodimers via analytical SEC-HPLC, the purity of the PD-L1 analog-Fc fusion protein solution in terms of the percentage of non-aggregated homodimer is ascertained.

Example 8: In vitro Fc (Gamma) and FcRn Receptor Binding Affinity for a PD-L1 Analog-Fc Fusion Protein The binding of PD-L1-Fc fusion proteins to the Fc (gamma) receptor I was conducted using an ELISA assay as follows. Human Fc(gamma) receptor I (i.e., rhFc (gamma) receptor I) was used as a surrogate mammalian receptor for canine Fc(gamma) receptor I which was unavailable at the time of testing. PD-L1-Fc fusion proteins were diluted to 10 μg/mL in sodium bicarbonate buffer at pH 9.6 and coated on Maxisorp (Nunc) microtiter plates overnight at 4° C., after which the microplate strips were washed 5 times with wash buffer (PBS/0.05% Tween-20) buffer and blocked with Superblock blocking reagent (ThermoFisher). Serial dilutions of His-Tagged rhFc(gamma) receptor I (recombinant human Fc(gamma)R-I; Acro Biosystems, catalog #FCA-H52H1) were prepared in PBST/SB (PBS/0.1% Tween-20/10% Superblock) buffer from 6000 ng/mL to 8.2 ng/mL, and optionally 0 ng/mL, and loaded at 100 μL/well onto the microplate strips coated with PD-L1-Fc fusion proteins. The microtiter plate was incubated for 1 hour at room temperature, after which the microplate strips were washed 5 times with wash buffer and then loaded with 100 μL/well of HRP anti-His Tag Antibody (BioLegend, Catalog #652504) diluted 1:40,000 in PBST/SB buffer. After incubating for 1 hour, the microplate strips were washed again 5 times with PBST and 1 time with distilled water. TMB was added to reveal the bound Fc(gamma) receptor I proteins and stopped with ELISA stop reagent (Boston Bioproducts). The plate was read in an ELISA plate reader at 450 nm, and the OD values (proportional to the binding of rhFc(gamma) receptor I to PD-L1-Fc fusion protein) are shown in Table 3 and were plotted against log concentrations of rhFc(gamma) receptor I added to each well to generate binding curves using GraphPad Prism software.

TABLE 3

| Fc(gamma)RI Binding to Various SEQ ID NOs as Measured by OD450 | |
| --- | --- |
| Compound | OD450 at 222 ng/ml Fc(gamma) RI |
| SEQ ID NO: 20 | 1.974 |
| SEQ ID NO: 21 | 2.047 |
| SEQ ID NO: 22 | 1.911 |
| SEQ ID NO: 24 | 1.494 |
| SEQ ID NO: 26 | 1.794 |

TABLE 3-continued

| Fc(gamma)RI Binding to Various SEQ ID NOs as Measured by OD450 | |
| --- | --- |
| Compound | OD450 at 222 ng/ml Fc(gamma) RI |
| SEQ ID NO: 27 | 1.779 |
| SEQ ID NO: 28 | 2.150 |
| SEQ ID NO: 32 | 1.698 |
| Dog IgG, Control Rockland-Inc, Cat# 004-0102-005 | 0.686 |

Example 9: In vivo ELISA Assay for Evaluating Anti-PD-L1 Antibody Levels in Mouse Serum Serum anti-PD-L1 antibody titers were determined by enzyme-linked immunosorbent assay (ELISA). Serum samples were diluted in Sample Dilution Buffer (SDB; containing a mixture of 10% Superblock (Thermo), 1% horse serum, 2 mM EDTA, and 0.05% Sodium Azide in PBS/0.1% Tween 20) at 1:100 and then added to microtiter plate wells that were coated with canine PD-L1 (ACRO Biosystems, Catalog #PDL-C52H4-100 ug) protein in carbonate buffer, blocked with SuperBlock™ (ThermoFisher) and then incubated with diluted serum test samples for one hour. It should be noted that canine PD-L1 has a known sequence and structure that is similar but not identical to that from other species (e.g., human). Mouse IgG, whole molecule (non-specific, Jackson Immunoresearch, Catalog #015-000-003) in carbonate buffer was directly coated to microplate wells with the mouse IgG antibody pre-diluted via serial dilutions to create a standard curve that allowed for quantitation of antibody (Ab) titers in the serum test samples. After washing the plate with wash buffer (PBS/0.05% Tween 20; PBST) to remove all unbound serum proteins, the bound PD-L1 specific mouse IgG Abs bound to the plate (precoated mouse IgG standards or mouse anti-PD-L1 Abs bound to the PD-L1-coated microplate) were detected by incubating microplate wells with goat anti-mouse-specific IgG Fc conjugated to HRP enzyme diluted between 1:4000 and 1:30000 (SouthernBiotech, Catalog #1013-05) in PBS/0.1% Tween 20+10% Superblock buffer for 1 hour. Following washes with PBST buffer, trimethyl-benzidine (TMB) reagent was added to each well that was catalyzed by the HRP enzyme and incubated for 5-30 minutes. This caused a colorimetric change that was proportional to the amount of bound HRP-antibody conjugate. The enzyme substrate reaction was then stopped by the addition of Stop Reagent (1% H2SO4) and the color intensity (optical density, OD) of each well was measured using a spectrophotometric microplate reader at 450 nm wavelength. The OD450 values were further converted to antibody titers (e.g., levels) using the mouse IgG standards, using a 4-parameter regression curve fit algorithm in SoftMax Pro software (Molecular Devices). Responders to the administered therapy in each test article group were defined as animals having an antibody titer on a given day that was more than twice the level of that measured on Day 0 for each individual animal.

Example 10: In vivo ELISA Assay for Evaluating Anti-PD-L1 Antibody Levels in Canine Serum Serum anti-PD-L1 antibody titers were determined by enzyme-linked immunosorbent assay (ELISA). Serum samples were diluted in Sample Dilution Buffer (SDB; containing a mixture of 10% Superblock (Thermo) in PBS/ 0.1% Tween 20, 20% Horse Scrum, 2 mM EDTA, and 0.05% Sodium Azide) at 1:100-10000 and then added to microtiter plate wells previously coated with Canine-PD-L1 (Acro Biosystems, Catalog #PDL-C52H4) protein in carbonate buffer, blocked with SuperBlock™ (ThermoFisher) and then incubated with diluted serum test samples for one hour. Dog IgG antibody (non-specific, Rockland Immunochemicals) in carbonate buffer was directly coated to microplate wells with the dog IgG antibody pre-diluted via serial dilutions to create a standard curve that allowed for quantitation of antibody (Ab) titers in the serum test samples. After washing the plate with wash buffer (PBS/0.05% Tween 20; PBST) to remove all unbound serum proteins, the bound PD-L1 specific dog IgG Abs bound to the plate (including precoated dog IgG standards or dog serum containing anti-PD-L1 Abs bound to the Canine PD-L1-coated microplate) were detected by incubating microplate wells with goat anti-cat-IgG F (ab')2 conjugated to HRP enzyme diluted between 1:4000 and 1:30000 (Jackson Immunoresearch, Catalog #102-035-006; anti-cat reagent was expected to cross react with dog antibodies) in PBS/0.1% Tween-20/10% SuperBlock™ buffer for 1 hour. Following washes with PBST buffer and purified water, trimethylbenzidine (TMB) reagent was added to each well which was catalyzed by the HRP enzyme and incubated for 5-20 minutes. This caused a colorimetric change that was proportional to the amount of bound HRP-antibody conjugate. The enzyme substrate reaction was then stopped by the addition of Stop Reagent (1% H2SO4) and the color intensity (optical density, OD) of each well was measured using a spectrophotometric microplate reader at 450 nm wavelength. The OD450 values were further converted to antibody titers (e.g., levels) using the mouse IgG standards, using a 4-parameter regression curve fit algorithm in SoftMax Pro software (Molecular Devices).

Example 11: In vivo ELISA Assay for Evaluating Anti-PD-L1 Antibody Levels in Canine Serum Scrum anti-PD-L1 antibody titers are determined by enzyme-linked immunosorbent assay (ELISA). Serum samples are diluted in Sample Dilution Buffer (SDB; containing a mixture of 10% Superblock (Thermo) in PBS/0.1% Tween 20, 20% Horse Serum, 2 mM EDTA, and 0.05% Sodium Azide) at 1:100-10000 and then added to microtiter plate wells previously coated with Canine-PD-L1 (Acro Biosystems, Catalog #PDL-C52H4) protein in carbonate buffer, blocked with SuperBlock™ (ThermoFisher) and then incubated with diluted serum test samples for one hour. Dog IgG antibody (non-specific, Rockland Immunochemicals) in carbonate buffer is directly coated to microplate wells with the dog IgG antibody pre-diluted via serial dilutions to create a standard curve that allows for quantitation of antibody (Ab) titers in the serum test samples. After washing the plate with wash buffer (PBS/0.05% Tween 20; PBST) to remove all unbound serum proteins, the bound PD-L1 specific dog IgG Abs bound to the plate (including precoated dog IgG standards or dog serum containing anti-PD-L1 Abs bound to the Canine PD-L1-coated microplate) are detected by incubating microplate wells with goat anti-cat-IgG F (ab')2 conjugated to HRP enzyme diluted between 1:4000 and 1:30000 (Jackson Immunoresearch, Catalog #102-035-006; anti-cat reagent is expected to cross react with dog antibodies) in PBS/0.1% Tween-20/10% SuperBlock™ buffer for 1 hour. Following washes with PBST buffer and purified water, trimethylbenzidine (TMB) reagent is added to each well which is catalyzed by the HRP enzyme and incubated for 5-20 minutes. This causes a colorimetric change that is proportional to the amount of bound HRP-antibody conjugate. The enzyme substrate reaction is then stopped by the addition of Stop Reagent (1% H2SO4) and the color intensity (optical density, OD) of each well is measured using a spectrophotometric microplate reader at 450 nm wavelength. The OD450 values are further converted to antibody titers (e.g., levels) using the mouse IgG standards, using a 4-parameter regression curve fit algorithm in SoftMax Pro software (Molecular Devices).

Example 12: In vivo General Preclinical Evaluation of the Effectiveness of PD-L1 Analog-Fc Formulations in Inducing an Anti-PD-L1 IgG Ab Titer in Mice Groups of female BALB/c mice (N=5; (Jackson Laboratories, Bar Harbor, ME)) at 6-8 weeks of age were injected subcutaneously (s.c.) on Days 0, 21, and 42 with the respective dose levels of test compounds made via Example 1 and purified via Example 3. Mice were administered three subcutaneous doses of 27 µg of the PD-L1 analog-Fc fusion protein of SEQ ID NO: 20, SEQ ID NO: 21, SEQ ID NO: 22, SEQ ID NO: 24, SEQ ID NO: 26, SEQ ID NO: 27, SEQ ID NO: 28, and SEQ ID NO: 32 with Montanide™ ISA 720 (30% test article/70% adjuvant v/v).

All mice were non-terminally bled via submandibular venipuncture before dosing and 14 days after each injection. Additional blood collection was done on Day 107. Blood samples were allowed to clot and were centrifuged to obtain serum samples for anti-PD-L1 antibody titer assessment by ELISA according to the methods described in Example 9.

The anti-PD-L1 antibody titer values of the novel PD-L1 analog-Fc fusion proteins of SEQ ID NO: 20, SEQ ID NO: 21, SEQ ID NO: 22, SEQ ID NO: 24, SEQ ID NO: 26, SEQ ID NO: 27, SEQ ID NO: 28, and SEQ ID NO: 32 in mice are shown in Table 4 and Table 5. A comparison of the immunogenicity of SEQ ID NO: 20, SEQ ID NO: 21, SEQ ID NO: 22, SEQ ID NO: 24, SEQ ID NO: 26, SEQ ID NO: 27, SEQ ID NO: 28, and SEQ ID NO: 32 is shown in FIG. 15, FIG. 16, FIG. 17, FIG. 18, FIG. 19, and FIG. 20 for Day 35 and in FIG. 21 for Day 107.

TABLE 4

| | | | Mean Anti-PD-L1 Antibody Titer (µg/mL) | | Fraction of Responders at Day 35 (Out of N = 5 |
|---|---|---|---|---|---|

Mean (N = 5) Anti-PD-L1 Antibody Titer Values
of Novel PD-L1 Analog-Fc Fusion Proteins in Mice

| SEQ ID NO: | Adjuvant/ Type | Dose (µg) per Injection | Day 0 | Day 35 | Per Group) |
|---|---|---|---|---|---|
| SEQ ID NO: 20 | ISA-720 | 27 | <LLOQ* | 3.8 | 5/5 |
| SEQ ID NO: 21 | ISA-720 | 27 | <LLOQ* | 1.3 | 3/5 |
| SEQ ID NO: 22 | ISA-720 | 27 | <LLOQ* | 7.8 | 4/5 |
| SEQ ID NO: 24 | ISA-720 | 27 | <LLOQ* | 67.3 | 5/5 |
| SEQ ID NO: 26 | ISA-720 | 27 | <LLOQ* | 84.4 | 5/5 |
| SEQ ID NO: 27 | ISA-720 | 27 | <LLOQ* | 84.8 | 5/5 |
| SEQ ID NO: 28 | ISA-720 | 27 | <LLOQ* | 113.1 | 5/5 |
| SEQ ID NO: 32 | ISA-720 | 27 | <LLOQ* | 49.6 | 4/5 |

*LLOQ: Lower Limit of Quantification.

TABLE 5

Mean (N = 5) Anti-PD-L1 Antibody Titer Values
of Novel PD-L1 Analog-Fc Fusion Proteins in Mice

| SEQ ID NO: | Adjuvant/ Type | Dose (µg) per Injection | Day 0 | Day 35 | Day 107 | Fraction of Responders at Day 107 (Out of N = 5 Per Group) |
|---|---|---|---|---|---|---|
| SEQ ID NO: 20 | ISA-720 | 27 | <LLOQ* | 3.8 | 46.1 | 5/5 |
| SEQ ID NO: 21 | ISA-720 | 27 | <LLOQ* | 1.3 | 5.5 | 3/5 |
| SEQ ID NO: 22 | ISA-720 | 27 | <LLOQ* | 7.8 | 66.8 | 4/5 |
| SEQ ID NO: 24 | ISA-720 | 27 | <LLOQ* | 67.3 | 614.7 | 5/5 |
| SEQ ID NO: 26 | ISA-720 | 27 | <LLOQ* | 84.4 | 723.2 | 5/5 |
| SEQ ID NO: 27 | ISA-720 | 27 | <LLOQ* | 84.8 | 581.6 | 5/5 |
| SEQ ID NO: 28 | ISA-720 | 27 | <LLOQ* | 113.1 | 514.8 | 5/5 |
| SEQ ID NO: 32 | ISA-720 | 27 | <LLOQ* | 49.6 | 326.0 | 4/5 |

*LLOQ: Lower Limit of Quantification.

Example 13: In vivo General Preclinical Evaluation of the Effectiveness of PD-L1 Analog-Fc Formulations in Inducing an Anti-PD-L1 IgG Ab Titer in Dogs Groups of dogs (N=1; (Transpharmation, Fergus, Ontario, CANADA)) of mixed ages (10 months to 12 years of age) were injected intramuscularly (i.m.) on Days 0, 14, 28 and an additional booster on Day 56 with respective adjuvant and dose level of test compounds made via Example 1 and purified via Example 3. Dogs were administered four i.m. doses of 90 µg of the PD-L1 analog-Fc fusion protein of SEQ ID NO: 24, SEQ ID NO: 26 and SEQ ID NO: 27 with either adjuvant (Sepivac SWE™ (50%/50% v/v) or Quil-A™ (600 µg per dose)).

All dogs were non-terminally bled via jugular venipuncture before dosing (Day 0) and 14 days after each injection (Days 14, 28, 42, and 70). Additional blood collection was performed on Day 56. Blood samples were allowed to clot and were centrifuged to obtain serum samples for anti-PD-L1 antibody titer assessment by ELISA according to the methods described in Example 10. As shown in FIG. 22, the anti-cPD-L1 antibody titers in each dog (N=1) increased from the initial treatment with the PD-L1 analog-Fc fusion protein of SEQ ID NO: 24, SEQ ID NO: 26 or SEQ ID NO:

27, showing increased titers in particular on Day 28, Day 56, and Day 70 after the initial treatment.

Example 14: In vivo General Preclinical Evaluation of the Effectiveness of PD-L1 Analog-Fc Formulations in Inducing an Anti-PD-L1 IgG Ab Titer in Dogs Groups of dogs (N=1; (Transpharmation, Fergus, Ontario, CANADA)) of mixed ages (10 months to 12 years of age) are injected intramuscularly (i.m.) on Days 0, 14, 28 and an additional booster on Day 56 with respective adjuvant and dose level of test compounds made via Example 1 and purified via Example 3. Dogs are administered four i.m. doses of 90 µg of the PD-L1 analog-Fc fusion protein of SEQ ID NO: 20, SEQ ID NO: 21, SEQ ID NO: 22, SEQ ID NO: 28 or SEQ ID NO: 32 with either adjuvant (Sepivac SWE™ (50%/50% v/v) or Quil-A™ (600 µg/dose)).

All dogs are non-terminally bled via jugular venipuncture before dosing (Day 0) and 14 days after each injection (Days 14, 28, 42, and 70). Additional blood collection is performed on Day 56. Blood samples are allowed to clot and are centrifuged to obtain serum samples for anti-PD-L1 antibody titer assessment by ELISA according to the methods described in Example 11. It is expected that the anti-cPD-L1 antibody titers in each dog (N=1) treated with the PD-L1 analog-Fc fusion protein of SEQ ID NO: 28 or SEQ ID NO: 32 will increase following the initial treatment, and will show increased titers in particular on Day 28, Day 56, and Day 70 after the initial treatment. It is expected that the anti-cPD-L1 antibody titers in each dog (N=1) treated with the PD-L1 analog-Fc fusion protein of SEQ ID NO: 20, SEQ ID NO: 21, or SEQ ID NO: 22 will not significantly increase following the initial treatment or will increase significantly less (e.g., at least three times less) than for each dog treated with the PD-L1 analog-Fc fusion protein of SEQ ID NO: 24, SEQ ID NO: 26 or SEQ ID NO: 27.

Example 15: In vitro Neutralization ELISA Assay of Canine PD-L1 by Anti-PD-L1 Antibody Levels in Canine Serum Canine PD-L1 binding to canine PD-1 protein was determined by enzyme-linked immunosorbent assay (ELISA) and as such, potential neutralization of this binding arising from antibodies present in canine serum was measured using this technique. Serum samples were diluted in Sample Dilution Buffer (SDB; containing a mixture of 10% Superblock™ (Thermo) in PBS/0.1% Tween 20, 10% Horse Serum, 2 mM EDTA, and 0.05% Sodium Azide) at 1:100-1000, spiked with canine PD-L1-human Fc tag (AcroBiosystems, Catalog #PD1-C52H3) at different concentrations, incubated for 45 minutes at room temperature, and then added to the plate wells previously coated with canine PD-1 (AcroBiosystems, Catalog #PD1-C52H9) protein in carbonate buffer, blocked with SuperBlock™ (ThermoFisher) and then incubated with diluted serum test samples spiked with canine PD-L1 for one hour. Canine PD-L1 was also separately spiked with SDB (containing no Canine serum) at different concentrations, incubated for 45 mins at room temperature, and then added to the plate wells to create a standard curve that allowed for quantitation of canine PD-L1 binding to canine PD-1 protein in the presence of anti-PD-L1 antibodies. After washing the plate with wash buffer (PBS/0.05% Tween 20; PBST) to remove all unbound proteins, the bound canine PD-L1 proteins were detected by incubating the microplate wells with goat anti-Human IgG-Fc (Southern Biotech, Catalog #2048-05) conjugated to HRP enzyme diluted between 1:2000 and 1:20000 in PBS/0.1% Tween 20/10% SuperBlock™ buffer for 1 hour. Following washes with PBST buffer and purified water, trimethylbenzidine (TMB) reagent was added to each well which was catalyzed by the HRP enzyme and incubated for 5-30 minutes. This caused a colorimetric change that was proportional to the amount of bound HRP-antibody conjugate. The enzyme substrate reaction was then stopped by the addition of Stop Reagent (1% H2SO4) and the color intensity (optical density, OD) of each well was measured using a spectrophotometric microplate reader at 450 nm wavelength.

As shown in FIG. 23, the PD-L1 binding to canine PD-1 protein in the presence of the anti-PD-L1 antibodies in dogs treated with the PD-L1 analog-Fc fusion protein of SEQ ID NO: 24, SEQ ID NO: 26 or SEQ ID NO: 27 was inhibited by between 45% and 75% 42 days after the initial treatment.

Example 16: In vitro Neutralization ELISA Assay of Canine PD-L1 by Anti-PD-L1 Antibody Levels in Canine Serum Canine PD-L1 binding to canine PD-1 protein is determined by enzyme-linked immunosorbent assay (ELISA) and as such, potential neutralization of this binding arising from antibodies present in canine serum can be measured using this technique. Serum samples are diluted in Sample Dilution Buffer (SDB; containing a mixture of 10% Superblock™ (Thermo) in PBS/0.1% Tween 20, 10% Horse Serum, 2 mM EDTA, and 0.05% Sodium Azide) at 1:100-1000, spiked with canine PD-L1-Fc tag (AcroBiosystems, Catalog #PD1-C52H3) at different concentrations, incubated for 45 minutes at room temperature, and then added to the plate wells previously coated with canine PD-1 (AcroBiosystems, Catalog #PD1-C52H9) protein in carbonate buffer, blocked with SuperBlock™ (ThermoFisher) and then incubated with diluted serum test samples spiked with canine PD-L1 for one hour. Canine PD-L1 is also separately spiked with SDB (containing no Canine serum) at different concentrations, incubated for 45 mins at room temperature, and then added to the plate wells to create a standard curve that allows for quantitation of canine PD-L1 binding to canine PD-1 protein in the presence of anti-PD-L1 antibodies. After washing the plate with wash buffer (PBS/0.05% Tween 20; PBST) to remove all unbound proteins, the bound canine PD-L1 proteins are detected by incubating the microplate wells with goat anti-Human IgG-Fc (Southern Biotech, Catalog #2048-05) conjugated to HRP enzyme diluted between 1:2000 and 1:20000 in PBS/0.1% Tween 20/10% SuperBlock™ buffer for 1 hour. Following washes with PBST buffer and purified water, trimethylbenzidine (TMB) reagent is added to each well which is catalyzed by the HRP enzyme and incubated for 5-30 minutes. This causes a colorimetric change that is proportional to the amount of bound HRP-antibody conjugate. The enzyme substrate reaction is then stopped by the addition of Stop Reagent (1% H2SO4) and the color intensity (optical density, OD) of each well is measured using a spectrophotometric microplate reader at 450 nm wavelength.

It is expected that the PD-L1 binding to canine PD-1 protein in the presence of the anti-PD-L1 antibodies in dogs treated with the PD-L1 analog-Fc fusion protein of SEQ ID NO: 28 and SEQ ID NO: 32 will be inhibited, by at least 20%, measured using serum collected at 42 days after the initial treatment for animals dosed per Example 14. It is expected that the PD-L1 binding to canine PD-1 protein in the presence of the anti-PD-L1 antibodies in dogs treated with the PD-L1 analog-Fc fusion protein of SEQ ID NO: 20, SEQ ID NO: 21, and SEQ ID NO: 22 will exhibit minimal inhibition 42 days after the initial treatment.

EQUIVALENTS

In the claims, articles such as "a," "an," and "the" may mean one or more than one unless indicated to the contrary or otherwise evident from the context. Claims or descriptions that include "or" between one or more members of a group are considered satisfied if one, more than one, or all of the group members are present in, employed in, or otherwise relevant to a given product or process unless indicated to the contrary or otherwise evident from the context. The disclosure includes embodiments in which exactly one member of the group is present in, employed in, or otherwise relevant to a given product or process. The disclosure includes embodiments in which more than one, or all of the group members are present in, employed in, or otherwise relevant to a given product or process.

Furthermore, the disclosure encompasses all variations, combinations, and permutations in which one or more limitations, elements, clauses, and descriptive terms from one or more of the listed claims are introduced into another claim. For example, any claim that is dependent on another claim can be modified to include one or more limitations found in any other claim that is dependent on the same base claim. Where elements are presented as lists, e.g., in Markush group format, each subgroup of the elements is also disclosed, and any element(s) can be removed from the group. It should be understood that, in general, where the disclosure, or aspects of the disclosure, is/are referred to as comprising particular elements and/or features, certain embodiments of the disclosure or aspects of the disclosure consist, or consist essentially of, such elements and/or features. For purposes of simplicity, those embodiments have not been specifically set forth in haec verba herein. It is also noted that the terms "comprise(s)," "comprising," "contain(s)," and "containing" are intended to be open and the use thereof permits the inclusion of additional elements or steps. Where ranges are given, endpoints are included. Furthermore, unless otherwise indicated or otherwise evident from the context and understanding of one of ordinary skill in the art, values that are expressed as ranges can assume any specific value or subrange within the stated ranges in different embodiments of the disclosure, to the tenth of the unit of the lower limit of the range, unless the context clearly dictates otherwise.

Additional advantages of the various embodiments of the technology will be apparent to those skilled in the art upon review of the disclosure herein and the working examples below. It will be appreciated that the various embodiments described herein are not necessarily mutually exclusive unless otherwise indicated herein. For example, a feature described or depicted in one embodiment may also be included in other embodiments but is not necessarily included. Thus, the present invention encompasses a variety of combinations and/or integrations of the specific embodiments described herein.

The present description also uses numerical ranges to quantify certain parameters relating to various embodiments of the invention. It should be understood that when numerical ranges are provided, such ranges are to be construed as providing literal support for claim limitations that only recite the lower value of the range as well as claim limitations that only recite the upper value of the range. For example, a disclosed numerical range of about 10 to about 100 provides literal support for a claim reciting "greater than about 10" (with no upper bounds) and a claim reciting "less than about 100" (with no lower bounds).

---

SEQUENCE LISTING

```
Sequence total quantity: 32
SEQ ID NO: 1              moltype = AA  length = 224
FEATURE                   Location/Qualifiers
source                    1..224
                          mol_type = protein
                          organism = Canis sp.
SEQUENCE: 1
DCPKCPAPEM LGGPSVFIFP PKPKDTLLIA RTPEVTCVVV DLDPEDPEVQ ISWFVDGKQM   60
QTAKTQPREE QFNGTYRVVS VLPIGHQDWL KGKQFTCKVN NKALPSPIER TISKARGQAH  120
QPSVYVLPPS REELSKNTVS LTCLIKDFFP PDIDVEWQSN GQQEPESKYR TTPPQLDEDG  180
SYFLYSKLSV DKSRWQRGDT FICAVMHEAL HNHYTQESLS HSPG                   224

SEQ ID NO: 2              moltype = AA  length = 290
FEATURE                   Location/Qualifiers
source                    1..290
                          mol_type = protein
                          organism = Homo sapiens
SEQUENCE: 2
MRIFAVFIFM TYWHLLNAFT VTVPKDLYVV EYGSNMTIEC KFPVEKQLDL AALIVYWEME   60
DKNIIQFVHG EEDLKVQHSS YRQRARLLKD QLSLGNAALQ ITDVKLQDAG VYRCMISYGG  120
ADYKRITVKV NAPYNKINQR ILVVDPVTSE HELTCQAEGY PKAEVIWTSS DHQVLSGKTT  180
TTNSKREEKL FNVTSTLRIN TTTNEIFYCT FRRLDPEENH TAELVIPELP LAHPPNERTH  240
LVILGAILLC LGVALTFIFR LRKGRMMDVK KCGIQDTNSK KQSDTHLEET            290

SEQ ID NO: 3              moltype = AA  length = 289
FEATURE                   Location/Qualifiers
source                    1..289
                          mol_type = protein
                          organism = Canis sp.
SEQUENCE: 3
MRMFSVFTFM AYCHLLKAFT ITVSKDLYVV EYGGNVTMEC KFPVEKQLNL FALIVYWEME   60
DKKIIQFVNG KEDLKVQHSS YSQRAQLLKD QLFLGKAALQ ITDVRLQDAG VYCCLIGYGG  120
ADYKRITLKV HAPYRNISQR ISVDPVTSEH ELMCQAEGYP EAEVIWTSSD HRVLSGKTTI  180
TNSNREEKLF NVTSTLNINA TANEIFYCTF QRSGPEENNT AELVIPERLP VPASERTHFM  240
ILGPFLLLLG VVLAVTFCLK KHGRMMDVEK CCTRDRNSKK RNDIQFEET             289

SEQ ID NO: 4              moltype = AA  length = 288
FEATURE                   Location/Qualifiers
source                    1..288
                          mol_type = protein
                          organism = Homo sapiens
SEQUENCE: 4
MQIPQAPWPV VWAVLQLGWR PGWFLDSPDR PWNPPTFSPA LLVVTEGDNA TFTCSFSNTS   60
ESFVLNWYRM SPSNQTDKLA AFPEDRSQPG QDCRFRVTQL PNGRDFHMSV VRARRNDSGT  120
YLCGAISLAP KAQIKESLRA ELRVTERRAE VPTAHPSPSP RPAGQFQTLV VGVVGGLLGS  180
LVLLVWVLAV ICSRAARGTI GARRTGQPLK EDPSAVPVFS VDYGELDFQW REKTPEPPVP  240
CVPEQTEYAT IVFPSGMGTS SPARRGSADG PRSAQPLRPE DGHCSWPL              288

SEQ ID NO: 5              moltype = AA  length = 288
```

-continued

```
FEATURE                 Location/Qualifiers
source                  1..288
                        mol_type = protein
                        organism = Canis sp.
SEQUENCE: 5
MGSRRGPWPL VWAVLQLGWW PGWLLDSPDR PWSPLTFSPA QLTVQEGENA TFTCSLADIP    60
DSFVLNWYRL SPRNQTDKLA AFQEDRIEPG RDRRFRVTRL PNGRDFHMSI VAARLNDSGI   120
YLCGAIYLPP NTQINESPRA ELSVTERTLE PPTQSPSPPP RLSGQLQGLV IGVTSVLVGV   180
LLLLLLTWVL AAVFPRATRG ACVCGSEDEP LKEGPDAAPV FTLDYGELDF QWREKTPEPP   240
APCAPEQTEY ATIVFPGRPA SPGRRASASS LQGAQPPSPE DGPGLWPL                288

SEQ ID NO: 6            moltype = AA  length = 17
FEATURE                 Location/Qualifiers
source                  1..17
                        mol_type = protein
                        organism = synthetic construct
SEQUENCE: 6
GGGGQGGGSG GQGGGGG                                                   17

SEQ ID NO: 7            moltype = AA  length = 8
FEATURE                 Location/Qualifiers
source                  1..8
                        mol_type = protein
                        organism = synthetic construct
SEQUENCE: 7
QGGGSGGQ                                                              8

SEQ ID NO: 8            moltype = AA  length = 211
FEATURE                 Location/Qualifiers
source                  1..211
                        mol_type = protein
                        organism = synthetic construct
SEQUENCE: 8
TIECKFPVEK QLDLAALIVY WEMEDKNIIQ FVHGEEDLKV QHSSYRQRAR LLKDQLSLGN    60
AALQITDVKL QDAGVYRCMI SYGGADYKRI TVKVNAPYNK INQRILVVDP VTSEHELTCQ   120
AEGYPKAEVI WTSSDHQVLS GKTTTTNSKR EEKLFNVTST LRINTTTNEI FYCTFRRLDP   180
EENHTAELVI PELPLAHPPN ERTHLVILGA I                                  211

SEQ ID NO: 9            moltype = AA  length = 133
FEATURE                 Location/Qualifiers
source                  1..133
                        mol_type = protein
                        organism = synthetic construct
SEQUENCE: 9
MISYGGADYK RITVKVNAPY NKINQRILVV DPVTSEHELT CQAEGYPKAE VIWTSSDHQV    60
LSGKTTTTNS KREEKLFNVT STLRINTTTN EIFYCTFRRL DPEENHTAEL VIPELPLAHP   120
PNERTHLVIL GAI                                                      133

SEQ ID NO: 10           moltype = AA  length = 131
FEATURE                 Location/Qualifiers
source                  1..131
                        mol_type = protein
                        organism = synthetic construct
SEQUENCE: 10
FTVTVPKDLY VVEYGSNMTI ECKFPVEKQL DLAALIVYWE MEDKNIIQFV HGEEDLKVQH    60
SSYRQRARLL KDQLSLGNAA LQITDVKLQD AGVYRCMISY GGADYKRITV KVNAPYNKIN   120
QRILVVDPVT S                                                        131

SEQ ID NO: 11           moltype = AA  length = 35
FEATURE                 Location/Qualifiers
source                  1..35
                        mol_type = protein
                        organism = synthetic construct
SEQUENCE: 11
MISYGGADYK RITVKVNAPY NKINQRILVV DPVTS                               35

SEQ ID NO: 12           moltype = AA  length = 209
FEATURE                 Location/Qualifiers
source                  1..209
                        mol_type = protein
                        organism = synthetic construct
SEQUENCE: 12
TMECKFPVEK QLNLFALIVY WEMEDKKIIQ FVNGKEDLKV QHSSYSQRAQ LLKDQLFLGK    60
AALQITDVRL QDAGVYRCLI GYGGADYKRI TLKVHAPYRN ISQRISVDVP TSEHELMCQA   120
EGYPEAEVIW TSSDHRVLSG KTTITNSNRE EKLFNVTSTL NINATANEIF YCTFQRSGPE   180
ENNTAELVIP ERLPVPASER THFMILGPF                                     209

SEQ ID NO: 13           moltype = AA  length = 130
FEATURE                 Location/Qualifiers
```

```
source                    1..130
                          mol_type = protein
                          organism = synthetic construct
SEQUENCE: 13
FTITVSKDLY VVEYGGNVTM ECKFPVEKQL NLFALIVYWE MEDKKIIQFV NGKEDLKVQH    60
SSYSQRAQLL KDQLFLGKAA LQITDVRLQD AGVYRCLIGY GGADYKRITL KVHAPYRNIS   120
QRISVDPVTS                                                          130

SEQ ID NO: 14             moltype = AA   length = 34
FEATURE                   Location/Qualifiers
source                    1..34
                          mol_type = protein
                          organism = synthetic construct
SEQUENCE: 14
LIGYGGADYK RITLKVHAPY RNISQRISVD PVTS                                34

SEQ ID NO: 15             moltype = AA   length = 452
FEATURE                   Location/Qualifiers
source                    1..452
                          mol_type = protein
                          organism = synthetic construct
SEQUENCE: 15
TIECKFPVEK QLDLAALIVY WEMEDKNIIQ FVHGEEDLKV QHSSYRQRAR LLKDQLSLGN    60
AALQITDVKL QDAGVYRCMI SYGGADYKRI TVKVNAPYNK INQRILVVDP VTSEHELTCQ   120
AEGYPKAEVI WTSSDHQVLS GKTTTTNSKR EEKLFNVTST LRINTTTNEI FYCTFRRLDP   180
EENHTAELVI PELPLAHPPN ERTHLVILGA IGGGGQGGGS GGQGGGGGDC PKCPAPEMLG   240
GPSVFIFPPK PKDTLLIART PEVTCVVVDL DPEDPEVQIS WFVDGKQMQT AKTQPREEQF   300
NGTYRVVSVL PIGHQDWLKG KQFTCKVNNK ALPSPIERTI SKARGQAHQP SVYVLPPSRE   360
ELSKNTVSLT CLIKDFFPPD IDVEWQSNGQ QEPESKYRTT PPQLDEDGSY FLYSKLSVDK   420
SRWQRGDTFI CAVMHEALHN HYTQESLSHS PG                                 452

SEQ ID NO: 16             moltype = AA   length = 374
FEATURE                   Location/Qualifiers
source                    1..374
                          mol_type = protein
                          organism = synthetic construct
SEQUENCE: 16
MISYGGADYK RITVKVNAPY NKINQRILVV DPVTSEHELT CQAEGYPKAE VIWTSSDHQV    60
LSGKTTTTNS KREEKLFNVT STLRINTTTN EIFYCTFRRL DPEENHTAEL VIPELPLAHP   120
PNERTHLVIL GAIGGGGQGG GSGGQGGGGG DCPKCPAPEM LGGPSVFIFP PKPKDTLLIA   180
RTPEVTCVVV DLDPEDPEVQ ISWFVDGKQM QTAKTQPREE QFNGTYRVVS VLPIGHQDWL   240
KGKQFTCKVN NKALPSPIER TISKARGQAH QPSVYVLPPS REELSKNTVS LTCLIKDFFP   300
PDIDVEWQSN GQQEPESKYR TTPPQLDEDG SYFLYSKLSV DKSRWQRGDT FICAVMHEAL   360
HNHYTQESLS HSPG                                                     374

SEQ ID NO: 17             moltype = AA   length = 372
FEATURE                   Location/Qualifiers
source                    1..372
                          mol_type = protein
                          organism = synthetic construct
SEQUENCE: 17
FTVTVPKDLY VVEYGSNMTI ECKFPVEKQL DLAALIVYWE MEDKNIIQFV HGEEDLKVQH    60
SSYRQRARLL KDQLSLGNAA LQITDVKLQD AGVYRCMISY GGADYKRITV KVNAPYNKIN   120
QRILVVDPVT SGGGGQGGGS GGQGGGGGDC PKCPAPEMLG GPSVFIFPPK PKDTLLIART   180
PEVTCVVVDL DPEDPEVQIS WFVDGKQMQT AKTQPREEQF NGTYRVVSVL PIGHQDWLKG   240
KQFTCKVNNK ALPSPIERTI SKARGQAHQP SVYVLPPSRE ELSKNTVSLT CLIKDFFPPD   300
IDVEWQSNGQ QEPESKYRTT PPQLDEDGSY FLYSKLSVDK SRWQRGDTFI CAVMHEALHN   360
HYTQESLSHS PG                                                       372

SEQ ID NO: 18             moltype = AA   length = 276
FEATURE                   Location/Qualifiers
source                    1..276
                          mol_type = protein
                          organism = synthetic construct
SEQUENCE: 18
MISYGGADYK RITVKVNAPY NKINQRILVV DPVTSGGGGQ GGGSGGQGGG GGDCPKCPAP    60
EMLGGPSVFI FPPKPKDTLL IARTPEVTCV VVDLDPEDPE VQISWFVDGK QMQTAKTQPR   120
EEQFNGTYRV VSVLPIGHQD WLKGKQFTCK VNNKALPSPI ERTISKARGQ AHQPSVYVLP   180
PSREELSKNT VSLTCLIKDF FPPDIDVEWQ SNGQQEPESK YRTTPPQLDE DGSYFLYSKL   240
SVDKSRWQRG DTFICAVMHE ALHNHYTQES LSHSPG                             276

SEQ ID NO: 19             moltype = AA   length = 450
FEATURE                   Location/Qualifiers
source                    1..450
                          mol_type = protein
                          organism = synthetic construct
SEQUENCE: 19
TMECKFPVEK QLNLFALIVY WEMEDKKIIQ FVNGKEDLKV QHSSYSQRAQ LLKDQLFLGK    60
AALQITDVRL QDAGVYRCLI GYGGADYKRI TLKVHAPYRN ISQRISVDPV TSEHELMCQA   120
```

```
EGYPEAEVIW TSSDHRVLSG KTTITNSNRE EKLFNVTSTL NINATANEIF YCTFQRSGPE  180
ENNTAELVIP ERLPVPASER THFMILGPFG GGGQGGGSGG QGGGGGDCPK CPAPEMLGGP  240
SVFIFPPKPK DTLLIARTPE VTCVVVDLDP EDPEVQISWF VDGKQMQTAK TQPREEQFNG  300
TYRVVSVLPI GHQDWLKGKQ FTCKVNNKAL PSPIERTISK ARGQAHQPSV YVLPPSREEL  360
SKNTVSLTCL IKDFFPPDID VEWQSNGQQE PESKYRTTPP QLDEDGSYFL YSKLSVDKSR  420
WQRGDTFICA VMHEALHNHY TQESLSHSPG                                   450

SEQ ID NO: 20             moltype = AA  length = 371
FEATURE                   Location/Qualifiers
source                    1..371
                          mol_type = protein
                          organism = synthetic construct
SEQUENCE: 20
FTITVSKDLY VVEYGGNVTM ECKFPVEKQL NLFALIVYWE MEDKKIIQFV NGKEDLKVQH  60
SSYSQRAQLL KDQLFLGKAA LQITDVRLQD AGVYRCLIGY GGADYKRITL KVHAPYRNIS  120
QRISVDPVTS GGGGQGGGSG GQGGGGGDCP KCPAPEMLGG PSVFIFPPKP KDTLLIARTP  180
EVTCVVVDLD PEDPEVQISW FVDGKQMQTA KTQPREEQFN GTYRVVSVLP IGHQDWLKGK  240
QFTCKVNNKA LPSPIERTIS KARGQAHQPS VYVLPPSREE LSKNTVSLTC LIKDFFPPDI  300
DVEWQSNGQQ EPESKYRTTP PQLDEDGSYF LYSKLSVDKS RWQRGDTFIC AVMHEALHNH  360
YTQESLSHSP G                                                      371

SEQ ID NO: 21             moltype = AA  length = 275
FEATURE                   Location/Qualifiers
source                    1..275
                          mol_type = protein
                          organism = synthetic construct
SEQUENCE: 21
LIGYGGADYK RITLKVHAPY RNISQRISVD PVTSGGGGQG GGSGGQGGGG GDCPKCPAPE  60
MLGGPSVFIF PPKPKDTLLI ARTPEVTCVV VDLDPEDPEV QISWFVDGKQ MQTAKTQPRE  120
EQFNGTYRVV SVLPIGHQDW LKGKQFTCKV NNKALPSPIE RTISKARGQA HQPSVYVLPP  180
SREELSKNTV SLTCLIKDFF PPDIDVEWQS NGQQEPESKY RTTPPQLDED GSYFLYSKLS  240
VDKSRWQRGD TFICAVMHEA LHNHYTQESL SHSPG                             275

SEQ ID NO: 22             moltype = AA  length = 362
FEATURE                   Location/Qualifiers
source                    1..362
                          mol_type = protein
                          organism = synthetic construct
SEQUENCE: 22
FTITVSKDLY VVEYGGNVTM ECKFPVEKQL NLFALIVYWE MEDKKIIQFV NGKEDLKVQH  60
SSYSQRAQLL KDQLFLGKAA LQITDVRLQD AGVYRCLIGY GGADYKRITL KVHAPYRNIS  120
QRISVDPVTS QGGGSGGQDC PKCPAPEMLG GPSVFIFPPK PKDTLLIART PEVTCVVVDL  180
DPEDPEVQIS WFVDGKQMQT AKTQPREEQF NGTYRVVSVL PIGHQDWLKG KQFTCKVNNK  240
ALPSPIERTI SKARGQAHQP SVYVLPPSRE ELSKNTVSLT CLIKDFFPPD IDVEWQSNGQ  300
QEPESKYRTT PPQLDEDGSY FLYSKLSVDK SRWQRGDTFI CAVMHEALHN HYTQESLSHS  360
PG                                                                362

SEQ ID NO: 23             moltype = AA  length = 131
FEATURE                   Location/Qualifiers
source                    1..131
                          mol_type = protein
                          organism = synthetic construct
SEQUENCE: 23
LIGYGGADYK RITLKVHAPY RNISQRISVD PVTSEHELMC QAEGYPEAEV IWTSSDHRVL  60
SGKTTITNSN REEKLFNVTS TLNINATANE IFYCTFQRSG PEENNTAELV IPERLPVPAS  120
ERTHFMILGP F                                                      131

SEQ ID NO: 24             moltype = AA  length = 372
FEATURE                   Location/Qualifiers
source                    1..372
                          mol_type = protein
                          organism = synthetic construct
SEQUENCE: 24
LIGYGGADYK RITLKVHAPY RNISQRISVD PVTSEHELMC QAEGYPEAEV IWTSSDHRVL  60
SGKTTITNSN REEKLFNVTS TLNINATANE IFYCTFQRSG PEENNTAELV IPERLPVPAS  120
ERTHFMILGP FGGGGQGGGS GGQGGGGGDC PKCPAPEMLG GPSVFIFPPK PKDTLLIART  180
PEVTCVVVDL DPEDPEVQIS WFVDGKQMQT AKTQPREEQF NGTYRVVSVL PIGHQDWLKG  240
KQFTCKVNNK ALPSPIERTI SKARGQAHQP SVYVLPPSRE ELSKNTVSLT CLIKDFFPPD  300
IDVEWQSNGQ QEPESKYRTT PPQLDEDGSY FLYSKLSVDK SRWQRGDTFI CAVMHEALHN  360
HYTQESLSHS PG                                                     372

SEQ ID NO: 25             moltype = AA  length = 227
FEATURE                   Location/Qualifiers
source                    1..227
                          mol_type = protein
                          organism = synthetic construct
SEQUENCE: 25
FTITVSKDLY VVEYGGNVTM ECKFPVEKQL NLFALIVYWE MEDKKIIQFV NGKEDLKVQH  60
SSYSQRAQLL KDQLFLGKAA LQITDVRLQD AGVYRCLIGY GGADYKRITL KVHAPYRNIS  120
```

-continued

```
QRISVDPVTS EHELMCQAEG YPEAEVIWTS SDHRVLSGKT TITNSNREEK LFNVTSTLNI   180
NATANEIFYC TFQRSGPEEN NTAELVIPER LPVPASERTH FMILGPF                 227

SEQ ID NO: 26                moltype = AA  length = 459
FEATURE                      Location/Qualifiers
source                       1..459
                             mol_type = protein
                             organism = synthetic construct
SEQUENCE: 26
FTITVSKDLY VVEYGGNVTM ECKFPVEKQL NLFALIVYWE MEDKKIIQFV NGKEDLKVQH   60
SSYSQRAQLL KDQLFLGKAA LQITDVRLQD AGVYRCLIGY GGADYKRITL KVHAPYRNIS   120
QRISVDPVTS EHELMCQAEG YPEAEVIWTS SDHRVLSGKT TITNSNREEK LFNVTSTLNI   180
NATANEIFYC TFQRSGPEEN NTAELVIPER LPVPASERTH FMILGPFQGG GSGGGQDCPKC   240
PAPEMLGGPS VFIFPPKPKD TLLIARTPEV TCVVVDLDPE DPEVQISWFV DGKQMQTAKT   300
QPREEQFNGT YRVVSVLPIG HQDWLKGKQF TCKVNNKALP SPIERTISKA RGQAHQPSVY   360
VLPPSREELS KNTVSLTCLI KDFFPPDIDV EWQSNGQQEP ESKYRTTPPQ LDEDGSYFLY   420
SKLSVDKSRW QRGDTFICAV MHEALHNHYT QESLSHSPG                          459

SEQ ID NO: 27                moltype = AA  length = 468
FEATURE                      Location/Qualifiers
source                       1..468
                             mol_type = protein
                             organism = synthetic construct
SEQUENCE: 27
FTITVSKDLY VVEYGGNVTM ECKFPVEKQL NLFALIVYWE MEDKKIIQFV NGKEDLKVQH   60
SSYSQRAQLL KDQLFLGKAA LQITDVRLQD AGVYRCLIGY GGADYKRITL KVHAPYRNIS   120
QRISVDPVTS EHELMCQAEG YPEAEVIWTS SDHRVLSGKT TITNSNREEK LFNVTSTLNI   180
NATANEIFYC TFQRSGPEEN NTAELVIPER LPVPASERTH FMILGPFGGG GQGGGSGGQG   240
GGGGDCPKCP APEMLGGPSV FIFPPKPKDT LLIARTPEVT CVVVDLDPED PEVQISWFVD   300
GKQMQTAKTQ PREEQFNGTY RVVSVLPIGH QDWLKGKQFT CKVNNKALPS PIERTISKAR   360
GQAHQPSVYV LPPSREELSK NTVSLTCLIK DFFPPDIDVE WQSNGQQEPE SKYRTTPPQL   420
DEDGSYFLYS KLSVDKSRWQ RGDTFICAVM HEALHNHYTQ ESLSHSPG                468

SEQ ID NO: 28                moltype = AA  length = 468
FEATURE                      Location/Qualifiers
source                       1..468
                             mol_type = protein
                             organism = synthetic construct
SEQUENCE: 28
FTITVSKDLY VVEYGGNVTM ECKFPVEKQL NLFALIVYWE MEDKKIIQFV NGKEDLKVQH   60
SSYSQRAQLL KDQLFLGKAA LQITDVRLQD AGVYRCLIGY GGADYKRITL KVHAPYRNIS   120
QRISVDPVTS EHELMCQAEG YPEAEVIWTS SDHRVLSGKT TITNSNREEK LFNVTSTLNI   180
NATANEIFYC TFQRSGPEEN NTAELVIPER LPVPASERTH FMILGPFGGQ GGGSGGQGGG   240
GGDKTHTCPP CPAPELLGGP SVFLFPPKPK DTLMISRTPE VTCVVVDVSH EDPEVKFNWY   300
VDGVEVHNAK TKPREEQYNS TYRVVSVLTV LHQDWLNGKE YKCKVSNKAL PAPIEKTISK   360
AKGQPREPQV YTLPPSRDEL TKNQVSLTCL VKGFYPSDIA VEWESNGQPE NNYKTTPPVL   420
DSDGSFFLYS KLTVDKSRWQ QGNVFSCSVM HEALHNHYTQ KSLSLSPG                468

SEQ ID NO: 29                moltype = AA  length = 226
FEATURE                      Location/Qualifiers
source                       1..226
                             mol_type = protein
                             organism = Homo sapiens
SEQUENCE: 29
DKTHTCPPCP APELLGGPSV FLFPPKPKDT LMISRTPEVT CVVVDVSHED PEVKFNWYVD   60
GVEVHNAKTK PREEQYNSTY RVVSVLTVLH QDWLNGKEYK CKVSNKALPA PIEKTISKAK   120
GQPREPQVYT LPPSRDELTK NQVSLTCLVK GFYPSDIAVE WESNGQPENN YKTTPPVLDS   180
DGSFFLYSKL TVDKSRWQQG NVFSCSVMHE ALHNHYTQKS LSLSPG                  226

SEQ ID NO: 30                moltype = AA  length = 15
FEATURE                      Location/Qualifiers
source                       1..15
                             mol_type = protein
                             organism = synthetic construct
SEQUENCE: 30
GGQGGGSGGQ GGGGG                                                    15

SEQ ID NO: 31                moltype = AA  length = 227
FEATURE                      Location/Qualifiers
source                       1..227
                             mol_type = protein
                             organism = synthetic construct
SEQUENCE: 31
FTITVSKDLY VVEYGGNVTM ECKFPVEKQL NLFALIVYWE MEDKKIIQFV NGKEDLKVQH   60
SSYSQRAQLL KDQLFLGKAA LQITDVRLQD AGVYCCLIGY GGADYKRITL KVHAPYRNIS   120
QRISVDPVTS EHELMCQAEG YPEAEVIWTS SDHRVLSGKT TITNSNREEK LFNVTSTLNI   180
NATANEIFYC TFQRSGPEEN NTAELVIPER LPVPASERTH FMILGPF                 227

SEQ ID NO: 32                moltype = AA  length = 468
```

-continued

```
FEATURE          Location/Qualifiers
source           1..468
                 mol_type = protein
                 organism = synthetic construct
SEQUENCE: 32
FTITVSKDLY VVEYGGNVTM ECKFPVEKQL NLFALIVYWE MEDKKIIQFV NGKEDLKVQH   60
SSYSQRAQLL KDQLFLGKAA LQITDVRLQD AGVYCCLIGY GGADYKRITL KVHAPYRNIS  120
QRISVDPVTS EHELMCQAEG YPEAEVIWTS SDHRVLSGKT TITNSNREEK LFNVTSTLNI  180
NATANEIFYC TFQRSGPEEN NTAELVIPER LPVPASERTH FMILGPFGGG GQGGGSGGQG  240
GGGGDCPKCP APEMLGGPSV FIFPPKPKDT LLIARTPEVT CVVVDLDPED PEVQISWFVD  300
GKQMQTAKTQ PREEQFNGTY RVVSVLPIGH QDWLKGKQFT CKVNNKALPS PIERTISKAR  360
GQAHQPSVYV LPPSREELSK NTVSLTCLIK DFFPPDIDVE WQSNGQQEPE SKYRTTPPQL  420
DEDGSYFLYS KLSVDKSRWQ RGDTFICAVM HEALHNHYTQ ESLSHSPG            468
```

We claim:

1. A fusion protein comprising a PD-L1 analog and an Fc fragment, wherein the PD-L1 analog and the Fc fragment are connected by a peptide linker, wherein the PD-L1 analog consists of the sequence:

```
                                    (SEQ ID NO: 25)
FTITVSKDLYVVEYGGNVTMECKFPVEKQLNLFALIVYWEMEDKKIIQFV

NGKEDLKVQHSSYSQRAQLLKDQLFLGKAALQITDVRLQDAGVYRCLIGY

GGADYKRITLKVHAPYRNISQRISVDPVTSEHELMCQAEGYPEAEVIWTS

SDHRVLSGKTTITNSNREEKLFNVTSTLNINATANEIFYCTFQRSGPEEN

NTAELVIPERLPVPASERTHFMILGPF,
``` and
wherein the Fc fragment comprises the sequence:

```
                                    (SEQ ID NO: 1)
DCPKCPAPEMLGGPSVFIFPPKPKDTLLIARTPEVTCVVVDLDPEDPEVQ

ISWFVDGKQMQTAKTQPREEQFNGTYRVVSVLPIGHQDWLKGKQFTCKVN

NKALPSPIERTISKARGQAHQPSVYVLPPSREELSKNTVSLTCLIKDFFP

PDIDVEWQSNGQQEPESKYRTTPPQLDEDGSYFLYSKLSVDKSRWQRGDT

FICAVMHEALHNHYTQESLSHSPG.
```

2. The fusion protein of claim 1, wherein the PD-L1 analog and the Fc fragment are connected by the peptide linker comprising the sequence:

```
                                    (SEQ ID NO: 7)
        QGGGSGGQ.
```

3. A fusion protein comprising a PD-L1 analog consisting of SEQ ID NO: 25 and an Fc fragment, wherein the PD-L1 analog and the Fc fragment are connected by a peptide linker, wherein the fusion protein comprises the sequence:

```
                                    (SEQ ID NO: 26)
FTITVSKDLYVVEYGGNVTMECKFPVEKQLNLFALIVYWEMEDKKIIQFV

NGKEDLKVQHSSYSQRAQLLKDQLFLGKAALQITDVRLQDAGVYRCLIGY

GGADYKRITLKVHAPYRNISQRISVDPVTSEHELMCQAEGYPEAEVIWTS

SDHRVLSGKTTITNSNREEKLFNVTSTLNINATANEIFYCTFQRSGPEEN

NTAELVIPERLPVPASERTHFMILGPFQGGGSGGQDCPKCPAPEMLGGPS

VFIFPPKPKDTLLIARTPEVTCVVVDLDPEDPEVQISWFVDGKQMQTAKT
```

-continued

```
QPREEQFNGTYRVVSVLPIGHQDWLKGKQFTCKVNNKALPSPIERTISKA

RGQAHQPSVYVLPPSREELSKNTVSLTCLIKDFFPPDIDVEWQSNGQQEP

ESKYRTTPPQLDEDGSYFLYSKLSVDKSRWQRGDTFICAVMHEALHNHYT

QESLSHSPG.
```

4. The fusion protein of claim 1, wherein the fusion protein is a homodimer comprising two identical monomers bound together via one or more disulfide bonds.

5. The fusion protein of claim 1, wherein the Fc fragment is glycosylated.

6. An immunogenic composition comprising a fusion protein according to claim 1 and a pharmaceutically acceptable carrier.

7. The immunogenic composition of claim 6, further comprising an adjuvant.

8. A fusion protein comprising the sequence of SEQ ID NO: 26 or pharmaceutical composition thereof for use in treatment for cancers or tumors in dogs.

9. A method of treating cancers or tumors in a dog, the method comprising administering a fusion protein according to claim 1 or pharmaceutical composition thereof to a dog in need thereof.

10. The method of claim 9, wherein said fusion protein or pharmaceutical composition thereof is administered via injection.

11. The method of claim 10, wherein said fusion protein or pharmaceutical composition thereof is administered subcutaneously or intramuscularly.

12. The method of claim 9, wherein said fusion protein or pharmaceutical composition thereof is administered as a priming vaccine, the method further comprising administering a booster of said fusion protein or pharmaceutical composition thereof 7 to 14 days after administering said priming vaccine.

13. The method of claim 9, wherein said dog is antibody-positive to PD-L1 before said administering step, wherein said fusion protein or pharmaceutical composition thereof is administered as a booster vaccine to said dog.

14. A method of treating cancers or tumors in a dog, the method comprising administering a fusion protein according to claim 3 or pharmaceutical composition thereof to a dog in need thereof.

15. The method of claim 14, wherein said fusion protein or pharmaceutical composition thereof is administered via injection.

16. The method of claim 15, wherein said fusion protein or pharmaceutical composition thereof is administered subcutaneously or intramuscularly.

17. The method of claim 14, wherein said fusion protein or pharmaceutical composition thereof is administered as a priming vaccine, the method further comprising administering a booster of said fusion protein or pharmaceutical composition thereof 7 to 14 days after administering said priming vaccine.

18. The method of claim 14, wherein said dog is antibody-positive to PD-L1 before said administering step, wherein said fusion protein or pharmaceutical composition thereof is administered as a booster vaccine to said dog.

* * * * *